US011162945B2

(12) United States Patent
Jiang et al.

(10) Patent No.: US 11,162,945 B2
(45) Date of Patent: Nov. 2, 2021

(54) METHODS AND COMPOSITIONS FOR DETECTING SINGLE T CELL RECEPTOR AFFINITY AND SEQUENCE

(71) Applicant: Board of Regents, the University of Texas System, Austin, TX (US)

(72) Inventors: Ning Jiang, Austin, TX (US); Shuqi Zhang, Austin, TX (US); Keyue Ma, Austin, TX (US); Chenfeng He, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 233 days.

(21) Appl. No.: 16/092,607

(22) PCT Filed: Apr. 6, 2017

(86) PCT No.: PCT/US2017/026286
§ 371 (c)(1),
(2) Date: Oct. 10, 2018

(87) PCT Pub. No.: WO2017/180420
PCT Pub. Date: Oct. 19, 2017

(65) Prior Publication Data
US 2019/0094224 A1    Mar. 28, 2019

Related U.S. Application Data
(60) Provisional application No. 62/320,801, filed on Apr. 11, 2016.

(51) Int. Cl.
| | | |
|---|---|---|
| *C12N 5/0783* | (2010.01) | |
| *A61K 35/17* | (2015.01) | |
| *A61K 39/00* | (2006.01) | |
| *A61K 38/17* | (2006.01) | |
| *C07H 21/04* | (2006.01) | |
| *G01N 33/569* | (2006.01) | |
| *C07K 14/725* | (2006.01) | |
| *C12Q 1/68* | (2018.01) | |
| *A61K 39/385* | (2006.01) | |
| *G01N 33/555* | (2006.01) | |
| *C12Q 1/6881* | (2018.01) | |
| *C07K 17/02* | (2006.01) | |

(52) U.S. Cl.
CPC ..... *G01N 33/56977* (2013.01); *A61K 39/385* (2013.01); *C07K 14/7051* (2013.01); *C12Q 1/68* (2013.01); *C12Q 1/6881* (2013.01); *G01N 33/555* (2013.01); *G01N 33/56972* (2013.01); *C07K 17/02* (2013.01)

(58) Field of Classification Search
CPC .............. C12N 5/0636; A61P 35/00; A61K 2039/5158; A61K 35/17; A61K 39/0011
See application file for complete search history.

(56) References Cited

U.S. PATENT DOCUMENTS

| | | |
|---|---|---|
| 5,506,121 A | 4/1996 | Sherra et al. |
| 5,635,363 A | 6/1997 | Altman et al. |
| 7,776,562 B2 | 8/2010 | Busch et al. |
| 2002/0115061 A1* | 8/2002 | Chisari ............... C07K 14/005 435/5 |
| 2004/0137642 A1 | 7/2004 | Erfle et al. |
| 2013/0196861 A1 | 8/2013 | Quake et al. |
| 2013/0253842 A1 | 9/2013 | Sherwood et al. |
| 2015/0299656 A1* | 10/2015 | Gattinoni ............... A61K 35/17 424/93.71 |
| 2015/0299784 A1 | 10/2015 | Fan et al. |
| 2015/0337369 A1 | 11/2015 | Davis et al. |

OTHER PUBLICATIONS

Merkenschlager et al., "Stepwise B-cell-dependent expansion of T helper clonotypes diversifies the T-cell response", Nature Communications, 2016:1-13.*
Wang et al., "Streptamer versus tetramer-based selection of functional cytomegalovirus-specific T cell", Journal of the Formosan Medical Association, 2013, 112:338-345.*
Freeman et al., "Peripheral Blood T Lymphocytes and Lymphocytes Infiltrating Human Cancers Express Vascular Endothelial Growth Factor: A Potential Role for T Cells in Angiogenesis", Cancer Research, 1995, 55:4140-4145.*
Huang et al. "The kinetics of two dimensional TCR and pMHC interactions determine T cell responsiveness", Nature, 2010, 464(7290):932-936.*
Dudley et al. "Adoptive Cell transfer therapy following non-myeloablative but lymphodepleting chemotherapy for the treatment of patients with refractory metastatic melanoma", Journal of Clinical Oncology, 2005, 23(10):2346-2357.*
"FAQ for Flow Cytometry", Webpage dated Sep. 7, 2015, retrieved on Aug. 11, 2017, from URL:http://research.uthscsa.edu/facs/faq.asp.
"New to Sanger and Next-Generation Sequence Technology", Webpage dated Oct. 23, 2015, retrieved on Aug. 11, 2017, from URL:https://www.thermofisher.com/us/en/home/life-scince/sequencing/sequencing-education/sanger-next-generation-technology.html.
Blanchfield et al., "Monitoring the Dynamics of T Cell Clonal Diversity Using Recombinant Peptide:MHC Technology," *Front Immunol*, 4(170), 2013.
Dash et al., "Paired analysis of TCRα and TCRβ Chains at the Single-cell Level in Mice," *J Clin Invest*, 121(1):288-295, 2011.

(Continued)

*Primary Examiner* — Barry A Chestnut
(74) *Attorney, Agent, or Firm* — Parker Highlander PLLC

(57) ABSTRACT

Provided herein are methods for determining the T cell receptor affinity and sequence of antigen-specific T cells using a micropipette adhesion assay and single cell paired TCRα/TCRβ sequencing. Further provided are methods for the treatment of viral infections or cancers by adoptive transfer of high affinity functional T cells.

22 Claims, 21 Drawing Sheets
Specification includes a Sequence Listing.

(56) References Cited

OTHER PUBLICATIONS

Dudley et al., "Adoptive Cell Transfer Therapy Following Non-Myeloablative but Lymphodepleting Chemotherapy for the Treatment of Patients with Refractory Metastatic Melanoma," *J Clin Oncol.*, 23(10):2346-2357, 2005.
Extended European Search Report issued in European Application No. 17782871.2, dated Oct. 15, 2019.
Freeman et al., "Peripheral Blood T Lymphocytes and Lymphocytes Infiltrating Human Cancers Express Vascular Endothelial Growth Factor: A Potential Role for T Cells in Angiogenesis," *Cancer Res.*, 55(18):4140-4145, 1995.
Han, Arnold, et al. "Linking T-cell receptor sequence to functional phenotype at the single-cell level," *Nature Biotechnology* 32.7 (2014): 684.
Heiden et al., "pRESTO: a toolkit for processing high-throughput sequencing raw reads of lymphocyte receptor repertoires," *Bioinformatics*, 30(13):1930-1932, 2014.
Huang et al., "The Kinetics of Two-Dimensional TCR and pMHC Interactions Determine T Cell Responsiveness," *Nature*, 464(7290): 932-936, 2010.
International Search Report and Written Opinion issued in International Application No. PCT/US2017/026286, dated Sep. 11, 2017.
International Preliminary Report on Patentability issued in International Application No. PCT/US2017/026286, dated Oct. 25, 2018.
Jiang et al., "Determinism and Stochasticity During Maturation of the Zebrafish Antibody Repertoire," PNAS, 108(13):5348-5353, 2011.
Jiang et al., "Two-Stage Cooperative T cells Receptor-Peptide Major Histocompatibility Complex-CD8 Trimolecular Interactions Amplify Antigen Discrimination," Immunity, 34(1):13-23, 2011.
King, Carolyn G.. et al, "T cell affinity regulates asymmetric division, effector cell differentiation, and tissue pathology." *Immunity* 37.4 (2012): '709-720.
Knabel, Michael, et al. "Reversible MHC multimer staining for functional isolation of T-cell populations and effective adoptive transfer." Nature Medicine 8.6 (2002): 631-637.
Merkenschlager, "Stepwise B-cell-dependent expansion of T helper clonotypes diversifies the T-cell response," *Nature Commmunications*,7:10281, 2016.
Mir et al., "Short Barcodes for Next Generation Sequencing," *Plos One*, 8(12), 2013.
Office Communication issued in European Application No. 17782871. 2, dated Jun. 5, 2020.
Riddell, Stanley R., and Philip D. Greenberg. "The use of anti-CD3 and anti-CD28 monoclonal antibodies to clone and expand human antigen-specific T cells." *Journal immunological methods* 128.2 (1990): 189-201.
Rosenthal et al., "Low 2-Dimensional CD4 T Cell Receptor Affinity for Myelin Sets in Kinetics," *Plos One*, 7(3), 2012.
Vollmers et al., "Genetic Measurement of memory B cell recall using antibody repertoire sequencing," *PNAS*, 110(33):13463-13468, 2013.
Wang et al., "Streptamer Versus Tetramer-based Selection of Functional Cytomegalovirus-specific T-Cells," *J Formos Med Assoc.*, 112(6):338-345, 2012.
Weber et al., "Management of Immune-Related Adverse Events and Kinetics of Response With Ipilimumab," *J Clin Oncol.*, 30(21)2691-2697, 2012.
Weissbrich, "T cell receptor binding avidity of antigen-specific CD8+ cutotxic T cells in chronic infection," Dissertation dated Nov. 18, 2015, retrieved on Oct. 10, 2017, from the Internet: URL:https://mediatum.ub.tum.de/doc/1254464/1254464.pdf.
Zarnitsyna, et al., "Estimating the diversity, completeness, and cross-reactivity of the T cell repertoire," *Front Immunol*, 2013. 4:485, 2013.
Zehn et al., "Complete but curtailed T cell response to very low affinity antigen," *Nature*, 458(7235):211-214, 2009.
Zhang et al., "Direct measurement of T cell receptor affinity and sequence from naive antiviral T cells," *Nature*, 8(341), 2016.
Zhong et al., "T receptor cell affinity and avidity defines antitumor response and autoimmunity in T cell immunotherapy," *PNAS*, 110(17):6973-6978, 2013.
Zvyagin et al., "Distinctive properties of identical twins' TCR repertoires revealed by high-throughput sequencing," *PNAS*, 111(16):5980-5985, 2014.

\* cited by examiner

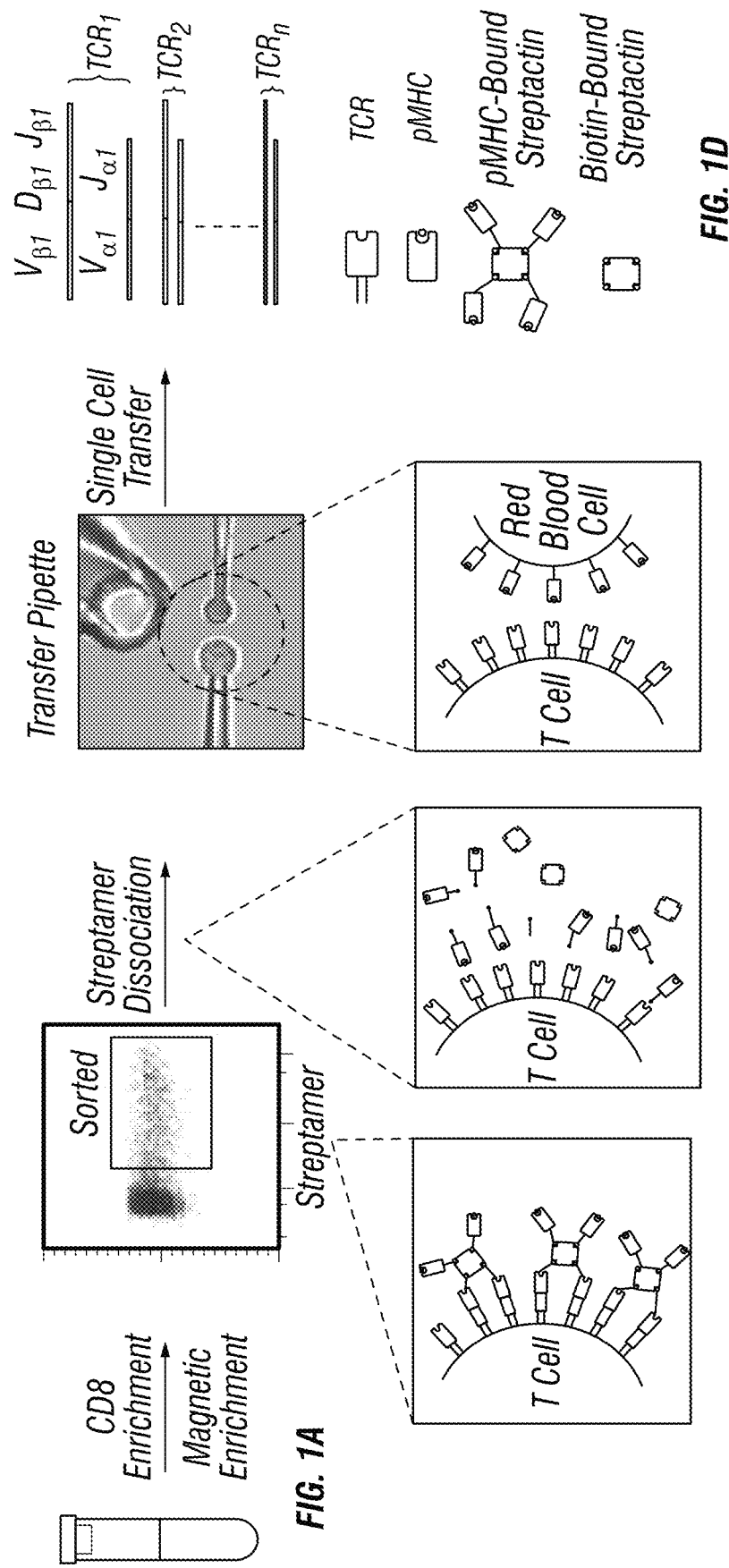

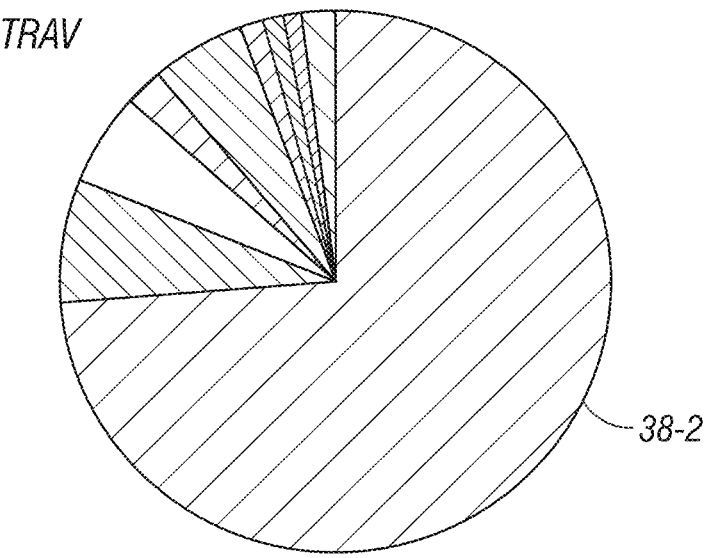
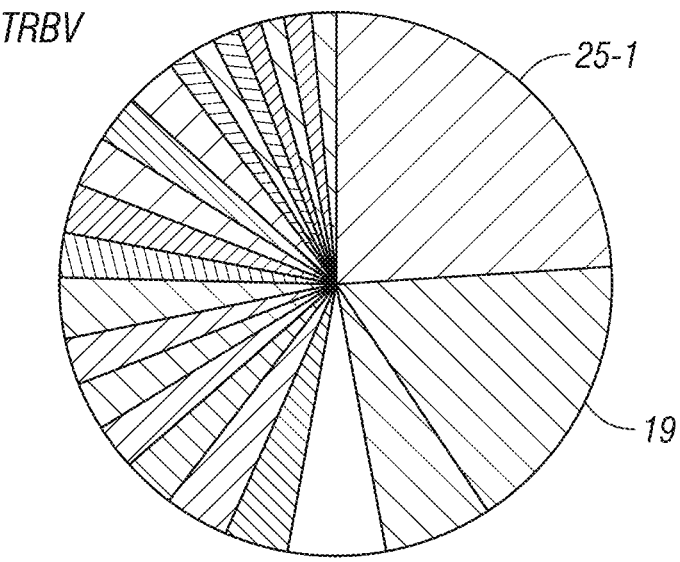
FIG. 5D a

| | low affinity (< 2x10⁵ μm⁴) | high affinity (> 2x10⁵ μm⁴) |
|---|---|---|
| old (49 + 62 yr) | 39 | 19 |
| young (33 yr) | 17 | 27 | b

| Donor | tet⁺ per 10⁶ CD8+ T cell | % naive |
|---|---|---|
| 1A | 0.19 | 75 |
| 1B | 0.96 | 80 |
| 2 | 0.27 | 63 |
| 3 | 2.74 | 97 |

A

| | Amplification Efficiency | |
|---|---|---|
| | Sample 1B | Sample 3 |
| TCRα | 9/16 (56%) | 25/44 (57%) |
| TCRβ | 13/16 (81%) | 33/44 (75%) |
| TCRαβ | 8/16 (50%) | 20/44 (45%) |

B

SEQUENCE LISTING

```
<160> NUMBER OF SEQ ID NOS: 172

<210> SEQ ID NO 1
<211> LENGTH: 10
<212> TYPE: PRT
<213> ORGANISM: Artificial Sequence
<220> FEATURE:
<223> OTHER INFORMATION: HCV Peptide

<400> SEQUENCE: 1

Lys Leu Val Ala Leu Gly Ile Asn Ala Val
1               5                   10

<210> SEQ ID NO 2
<211> LENGTH: 11
<212> TYPE: PRT
<213> ORGANISM: Artificial Sequence
<220> FEATURE:
<223> OTHER INFORMATION: High Affinity TCR 1

<400> SEQUENCE: 2

Cys Ala Ser Lys Met Gly Ala Glu Ala Phe Phe
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Low Affinity TCR 1

<400> SEQUENCE: 3

Cys Ala Ser Gly Gln Gly Gln Glu Thr Gln Tyr Phe
1               5                   10

<210> SEQ ID NO 4
<211> LENGTH: 15
<212> TYPE: PRT
<213> ORGANISM: Artificial Sequence
<220> FEATURE:
<223> OTHER INFORMATION: High Affinity TCR 2

<400> SEQUENCE: 4

Cys Ala Ser Ser Leu Glu Arg Glu Gly Arg Gly Glu Gln Phe Phe
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: Low Affinity TCR 2

<400> SEQUENCE: 5

Cys Ala Thr Ser Ile Asp Arg Gly Arg Glu Lys Leu Phe Phe
1               5                   10
```

<210> SEQ ID NO 6
<211> LENGTH: 25
<212> TYPE: DNA
<213> ORGANISM: Artificial Sequence
<220> FEATURE:
<223> OTHER INFORMATION: TCR Primer

<400> SEQUENCE: 6
gcacccacat tctktctta caatg                                          25

<210> SEQ ID NO 7
<211> LENGTH: 45
<212> TYPE: DNA
<213> ORGANISM: Artificial Sequence
<220> FEATURE:
<223> OTHER INFORMATION: TCR Primer

<400> SEQUENCE: 7
gacgtgtgct cttccgatct gamaggtcgt ttttcttcat tcctt                   45

<210> SEQ ID NO 8
<211> LENGTH: 25
<212> TYPE: DNA
<213> ORGANISM: Artificial Sequence
<220> FEATURE:
<223> OTHER INFORMATION: TCR Primer

<400> SEQUENCE: 8
atgtgcacca agactccttg ttaaa                                         25

<210> SEQ ID NO 9
<211> LENGTH: 45
<212> TYPE: DNA
<213> ORGANISM: Artificial Sequence
<220> FEATURE:
<223> OTHER INFORMATION: TCR Primer

<400> SEQUENCE: 9
gacgtgtgct cttccgatct agggacgata caacatgacc tatga                   45

<210> SEQ ID NO 10
<211> LENGTH: 21
<212> TYPE: DNA
<213> ORGANISM: Artificial Sequence
<220> FEATURE:
<223> OTHER INFORMATION: TCR Primer

<400> SEQUENCE: 10
gcagctatgg ctttgaagct g                                             21

<210> SEQ ID NO 11
<211> LENGTH: 40
<212> TYPE: DNA
<213> ORGANISM: Artificial Sequence
<220> FEATURE:
<223> OTHER INFORMATION: TCR Primer

<400> SEQUENCE: 11
gacgtgtgct cttccgatct tccttccacc tgavgaaacc                         40

<210> SEQ ID NO 12
<211> LENGTH: 21
<212> TYPE: DNA
<213> ORGANISM: Artificial Sequence
<220> FEATURE:

```
<223> OTHER INFORMATION: TCR Primer

<400> SEQUENCE: 12
aavggytttg aggctgaatt t                                       21

<210> SEQ ID NO 13
<211> LENGTH: 44
<212> TYPE: DNA
<213> ORGANISM: Artificial Sequence
<220> FEATURE:
<223> OTHER INFORMATION: TCR Primer

<400> SEQUENCE: 13
gacgtgtgct cttccgatct ttyaatctga ggaaaccctc tgtg              44

<210> SEQ ID NO 14
<211> LENGTH: 26
<212> TYPE: DNA
<213> ORGANISM: Artificial Sequence
<220> FEATURE:
<223> OTHER INFORMATION: TCR Primer

<400> SEQUENCE: 14
caagacaaaa gttacaaacg aagtgg                                  26

<210> SEQ ID NO 15
<211> LENGTH: 44
<212> TYPE: DNA
<213> ORGANISM: Artificial Sequence
<220> FEATURE:
<223> OTHER INFORMATION: TCR Primer

<400> SEQUENCE: 15
gacgtgtgct cttccgatct gacagaaagt ccagcactct gagc              44

<210> SEQ ID NO 16
<211> LENGTH: 25
<212> TYPE: DNA
<213> ORGANISM: Artificial Sequence
<220> FEATURE:
<223> OTHER INFORMATION: TCR Primer

<400> SEQUENCE: 16
tggacatgaa acaagaccaa agact                                   25

<210> SEQ ID NO 17
<211> LENGTH: 45
<212> TYPE: DNA
<213> ORGANISM: Artificial Sequence
<220> FEATURE:
<223> OTHER INFORMATION: TCR Primer

<400> SEQUENCE: 17
gacgtgtgct cttccgatct ggataaacat ctgtctctgc gcatt             45

<210> SEQ ID NO 18
<211> LENGTH: 24
<212> TYPE: DNA
<213> ORGANISM: Artificial Sequence
<220> FEATURE:
<223> OTHER INFORMATION: TCR Primer

<400> SEQUENCE: 18
aaaaaggaaa gaaagactga aggt                                    24
```

```
<210> SEQ ID NO 19
<211> LENGTH: 24
<212> TYPE: DNA
<213> ORGANISM: Artificial Sequence
<220> FEATURE:
<223> OTHER INFORMATION: TCR Primer

<400> SEQUENCE: 19
aaaaaggaaa gaaagactga aggt                                              24

<210> SEQ ID NO 20
<211> LENGTH: 25
<212> TYPE: DNA
<213> ORGANISM: Artificial Sequence
<220> FEATURE:
<223> OTHER INFORMATION: TCR Primer

<400> SEQUENCE: 20
tcagctggat atgagaagca gaaag                                             25

<210> SEQ ID NO 21
<211> LENGTH: 45
<212> TYPE: DNA
<213> ORGANISM: Artificial Sequence
<220> FEATURE:
<223> OTHER INFORMATION: TCR Primer

<400> SEQUENCE: 21
gacgtgtgct cttccgatct ttactgaaga atggaagcag cttgt                       45

<210> SEQ ID NO 22
<211> LENGTH: 25
<212> TYPE: DNA
<213> ORGANISM: Artificial Sequence
<220> FEATURE:
<223> OTHER INFORMATION: TCR Primer

<400> SEQUENCE: 22
aagggaagsa acaaaggttt tgaag                                             25

<210> SEQ ID NO 23
<211> LENGTH: 45
<212> TYPE: DNA
<213> ORGANISM: Artificial Sequence
<220> FEATURE:
<223> OTHER INFORMATION: TCR Primer

<400> SEQUENCE: 23
gacgtgtgct cttccgatct cgtaargaaa ccacttcttt ccact                       45

<210> SEQ ID NO 24
<211> LENGTH: 25
<212> TYPE: DNA
<213> ORGANISM: Artificial Sequence
<220> FEATURE:
<223> OTHER INFORMATION: TCR Primer

<400> SEQUENCE: 24
agaacacaaa gtcgaacgga agata                                             25

<210> SEQ ID NO 25
<211> LENGTH: 43
<212> TYPE: DNA
<213> ORGANISM: Artificial Sequence
<220> FEATURE:
<223> OTHER INFORMATION: TCR Primer
```

```
<400> SEQUENCE: 25
gacgtgtgct cttccgatct aagcaaagct ctctgcacat cac        43

<210> SEQ ID NO 26
<211> LENGTH: 25
<212> TYPE: DNA
<213> ORGANISM: Artificial Sequence
<220> FEATURE:
<223> OTHER INFORMATION: TCR Primer

<400> SEQUENCE: 26
ttgtgtcttt gaccttaatt caatc        25

<210> SEQ ID NO 27
<211> LENGTH: 46
<212> TYPE: DNA
<213> ORGANISM: Artificial Sequence
<220> FEATURE:
<223> OTHER INFORMATION: TCR Primer

<400> SEQUENCE: 27
gacgtgtgct cttccgatct gcttggaaaa garaartttt atagtg        46

<210> SEQ ID NO 28
<211> LENGTH: 23
<212> TYPE: DNA
<213> ORGANISM: Artificial Sequence
<220> FEATURE:
<223> OTHER INFORMATION: TCR Primer

<400> SEQUENCE: 28
tcartgttcc agagggagcc ayt        23

<210> SEQ ID NO 29
<211> LENGTH: 43
<212> TYPE: DNA
<213> ORGANISM: Artificial Sequence
<220> FEATURE:
<223> OTHER INFORMATION: TCR Primer

<400> SEQUENCE: 29
gacgtgtgct cttccgatct gaagatggaa ggtttacagc aca        43

<210> SEQ ID NO 30
<211> LENGTH: 22
<212> TYPE: DNA
<213> ORGANISM: Artificial Sequence
<220> FEATURE:
<223> OTHER INFORMATION: TCR Primer

<400> SEQUENCE: 30
ctgagtgtcc aggagggwga ca        22

<210> SEQ ID NO 31
<211> LENGTH: 47
<212> TYPE: DNA
<213> ORGANISM: Artificial Sequence
<220> FEATURE:
<223> OTHER INFORMATION: TCR Primer

<400> SEQUENCE: 31
gacgtgtgct cttccgatct tyattataga cattcgttca aatrtgg        47

<210> SEQ ID NO 32
<211> LENGTH: 24
```

```
<212> TYPE: DNA
<213> ORGANISM: Artificial Sequence
<220> FEATURE:
<223> OTHER INFORMATION: TCR Primer

<400> SEQUENCE: 32
agcagtgggg aaatgatttt tctt                                    24

<210> SEQ ID NO 33
<211> LENGTH: 45
<212> TYPE: DNA
<213> ORGANISM: Artificial Sequence
<220> FEATURE:
<223> OTHER INFORMATION: TCR Primer

<400> SEQUENCE: 33
gacgtgtgct cttccgatct ttgaatttcc agaaggcaag aaaat              45

<210> SEQ ID NO 34
<211> LENGTH: 25
<212> TYPE: DNA
<213> ORGANISM: Artificial Sequence
<220> FEATURE:
<223> OTHER INFORMATION: TCR Primer

<400> SEQUENCE: 34
tctagagaga gcatcaaagg cttca                                    25

<210> SEQ ID NO 35
<211> LENGTH: 45
<212> TYPE: DNA
<213> ORGANISM: Artificial Sequence
<220> FEATURE:
<223> OTHER INFORMATION: TCR Primer

<400> SEQUENCE: 35
gacgtgtgct cttccgatct gaccttaaca aaggcgagac atctt              45

<210> SEQ ID NO 36
<211> LENGTH: 25
<212> TYPE: DNA
<213> ORGANISM: Artificial Sequence
<220> FEATURE:
<223> OTHER INFORMATION: TCR Primer

<400> SEQUENCE: 36
cgttcaaatg aaagagagaa acaca                                    25

<210> SEQ ID NO 37
<211> LENGTH: 45
<212> TYPE: DNA
<213> ORGANISM: Artificial Sequence
<220> FEATURE:
<223> OTHER INFORMATION: TCR Primer

<400> SEQUENCE: 37
gacgtgtgct cttccgatct cttgacactt ccaagaaaag cagtt              45

<210> SEQ ID NO 38
<211> LENGTH: 25
<212> TYPE: DNA
<213> ORGANISM: Artificial Sequence
<220> FEATURE:
<223> OTHER INFORMATION: TCR Primer

<400> SEQUENCE: 38
```
cctgaaaagt tcagaaaacc aggag                                   25

<210> SEQ ID NO 39
<211> LENGTH: 45
<212> TYPE: DNA
<213> ORGANISM: Artificial Sequence
<220> FEATURE:
<223> OTHER INFORMATION: TCR Primer

<400> SEQUENCE: 39
gacgtgtgct cttccgatct ttttcaggcc agtcctatca agagt              45

<210> SEQ ID NO 40
<211> LENGTH: 25
<212> TYPE: DNA
<213> ORGANISM: Artificial Sequence
<220> FEATURE:
<223> OTHER INFORMATION: TCR Primer

<400> SEQUENCE: 40
ccttattcgt cggaactctt ttgat                                   25

<210> SEQ ID NO 41
<211> LENGTH: 45
<212> TYPE: DNA
<213> ORGANISM: Artificial Sequence
<220> FEATURE:
<223> OTHER INFORMATION: TCR Primer

<400> SEQUENCE: 41
gacgtgtgct cttccgatct tgaataagt ggtcggtatt cttgg              45

<210> SEQ ID NO 42
<211> LENGTH: 25
<212> TYPE: DNA
<213> ORGANISM: Artificial Sequence
<220> FEATURE:
<223> OTHER INFORMATION: TCR Primer

<400> SEQUENCE: 42
ctggggaaga aaggagaaa gaaag                                    25

<210> SEQ ID NO 43
<211> LENGTH: 45
<212> TYPE: DNA
<213> ORGANISM: Artificial Sequence
<220> FEATURE:
<223> OTHER INFORMATION: TCR Primer

<400> SEQUENCE: 43
gacgtgtgct cttccgatct agccacatta acaaagaagg aaagc              45

<210> SEQ ID NO 44
<211> LENGTH: 25
<212> TYPE: DNA
<213> ORGANISM: Artificial Sequence
<220> FEATURE:
<223> OTHER INFORMATION: TCR Primer

<400> SEQUENCE: 44
cagagagagc aaacaagtgg aagac                                   25

<210> SEQ ID NO 45
<211> LENGTH: 44
<212> TYPE: DNA
<213> ORGANISM: Artificial Sequence

```
<220> FEATURE:
<223> OTHER INFORMATION: TCR Primer

<400> SEQUENCE: 45
gacgtgtgct cttccgatct ttaatgcctc gctggataaa tcat                    44

<210> SEQ ID NO 46
<211> LENGTH: 25
<212> TYPE: DNA
<213> ORGANISM: Artificial Sequence
<220> FEATURE:
<223> OTHER INFORMATION: TCR Primer

<400> SEQUENCE: 46
catcaacctg ttttacattc cctca                                         25

<210> SEQ ID NO 47
<211> LENGTH: 44
<212> TYPE: DNA
<213> ORGANISM: Artificial Sequence
<220> FEATURE:
<223> OTHER INFORMATION: TCR Primer

<400> SEQUENCE: 47
gacgtgtgct cttccgatct gctacggaac gctacagctt attg                    44

<210> SEQ ID NO 48
<211> LENGTH: 25
<212> TYPE: DNA
<213> ORGANISM: Artificial Sequence
<220> FEATURE:
<223> OTHER INFORMATION: TCR Primer

<400> SEQUENCE: 48
gcattattga tagccatacg tccag                                         25

<210> SEQ ID NO 49
<211> LENGTH: 47
<212> TYPE: DNA
<213> ORGANISM: Artificial Sequence
<220> FEATURE:
<223> OTHER INFORMATION: TCR Primer

<400> SEQUENCE: 49
gacgtgtgct cttccgatct tgagtgaaaa gaaagaagga agattca                 47

<210> SEQ ID NO 50
<211> LENGTH: 25
<212> TYPE: DNA
<213> ORGANISM: Artificial Sequence
<220> FEATURE:
<223> OTHER INFORMATION: TCR Primer

<400> SEQUENCE: 50
taaatgggga tgaaaagaag aaagg                                         25

<210> SEQ ID NO 51
<211> LENGTH: 45
<212> TYPE: DNA
<213> ORGANISM: Artificial Sequence
<220> FEATURE:
<223> OTHER INFORMATION: TCR Primer

<400> SEQUENCE: 51
gacgtgtgct cttccgatct taccaaggag ggttacagct atttg                   45
```

<210> SEQ ID NO 52
<211> LENGTH: 20
<212> TYPE: DNA
<213> ORGANISM: Artificial Sequence
<220> FEATURE:
<223> OTHER INFORMATION: TCR Primer

<400> SEQUENCE: 52
ctggtggaca tcccgttttt                                           20

<210> SEQ ID NO 53
<211> LENGTH: 45
<212> TYPE: DNA
<213> ORGANISM: Artificial Sequence
<220> FEATURE:
<223> OTHER INFORMATION: TCR Primer

<400> SEQUENCE: 53
gacgtgtgct cttccgatct tggagaagtg aagaagcaga aaaga               45

<210> SEQ ID NO 54
<211> LENGTH: 23
<212> TYPE: DNA
<213> ORGANISM: Artificial Sequence
<220> FEATURE:
<223> OTHER INFORMATION: TCR Primer

<400> SEQUENCE: 54
attggtatcg acagmttcmc tcc                                       23

<210> SEQ ID NO 55
<211> LENGTH: 45
<212> TYPE: DNA
<213> ORGANISM: Artificial Sequence
<220> FEATURE:
<223> OTHER INFORMATION: TCR Primer

<400> SEQUENCE: 55
gacgtgtgct cttccgatct aagacagaaa gtccagyacc ttgat               45

<210> SEQ ID NO 56
<211> LENGTH: 25
<212> TYPE: DNA
<213> ORGANISM: Artificial Sequence
<220> FEATURE:
<223> OTHER INFORMATION: TCR Primer

<400> SEQUENCE: 56
cctgtcctcc tggtgacagt agtta                                     25

<210> SEQ ID NO 57
<211> LENGTH: 45
<212> TYPE: DNA
<213> ORGANISM: Artificial Sequence
<220> FEATURE:
<223> OTHER INFORMATION: TCR Primer

<400> SEQUENCE: 57
gacgtgtgct cttccgatct tggagaagtg aagaagctga agaga               45

<210> SEQ ID NO 58
<211> LENGTH: 25
<212> TYPE: DNA
<213> ORGANISM: Artificial Sequence
<220> FEATURE:
<223> OTHER INFORMATION: TCR Primer -continued

```
<400> SEQUENCE: 58 ggaccccctca tgtccttatt taaca                                       25

<210> SEQ ID NO 59
<211> LENGTH: 45
<212> TYPE: DNA
<213> ORGANISM: Artificial Sequence
<220> FEATURE:
<223> OTHER INFORMATION: TCR Primer

<400> SEQUENCE: 59
gacgtgtgct cttccgatct gaagactaaa atccgcagtc aaagc                  45

<210> SEQ ID NO 60
<211> LENGTH: 25
<212> TYPE: DNA
<213> ORGANISM: Artificial Sequence
<220> FEATURE:
<223> OTHER INFORMATION: TCR Primer

<400> SEQUENCE: 60
tgctgaaggt cctacattcc tgata                                        25

<210> SEQ ID NO 61
<211> LENGTH: 47
<212> TYPE: DNA
<213> ORGANISM: Artificial Sequence
<220> FEATURE:
<223> OTHER INFORMATION: TCR Primer

<400> SEQUENCE: 61
gacgtgtgct cttccgatct tccattaagg ataaaaatga agatgga                47

<210> SEQ ID NO 62
<211> LENGTH: 25
<212> TYPE: DNA
<213> ORGANISM: Artificial Sequence
<220> FEATURE:
<223> OTHER INFORMATION: TCR Primer

<400> SEQUENCE: 62
cccgtcttcc tgatgatatt actga                                        25

<210> SEQ ID NO 63
<211> LENGTH: 45
<212> TYPE: DNA
<213> ORGANISM: Artificial Sequence
<220> FEATURE:
<223> OTHER INFORMATION: TCR Primer

<400> SEQUENCE: 63
gacgtgtgct cttccgatct aagcrgcaaa gctccctgta cctta                  45

<210> SEQ ID NO 64
<211> LENGTH: 26
<212> TYPE: DNA
<213> ORGANISM: Artificial Sequence
<220> FEATURE:
<223> OTHER INFORMATION: TCR Primer

<400> SEQUENCE: 64
gaagattatt ttcctcattt atcagc                                       26

<210> SEQ ID NO 65
```

<211> LENGTH: 44
<212> TYPE: DNA
<213> ORGANISM: Artificial Sequence
<220> FEATURE:
<223> OTHER INFORMATION: TCR Primer

<400> SEQUENCE: 65
gacgtgtgct cttccgatct aatgcgacac agggtcaata ttct                    44

<210> SEQ ID NO 66
<211> LENGTH: 25
<212> TYPE: DNA
<213> ORGANISM: Artificial Sequence
<220> FEATURE:
<223> OTHER INFORMATION: TCR Primer

<400> SEQUENCE: 66
gggaaggccc taatatctta atgga                                         25

<210> SEQ ID NO 67
<211> LENGTH: 45
<212> TYPE: DNA
<213> ORGANISM: Artificial Sequence
<220> FEATURE:
<223> OTHER INFORMATION: TCR Primer

<400> SEQUENCE: 67
gacgtgtgct cttccgatct tgtggataga aacaggaca gaagg                    45

<210> SEQ ID NO 68
<211> LENGTH: 25
<212> TYPE: DNA
<213> ORGANISM: Artificial Sequence
<220> FEATURE:
<223> OTHER INFORMATION: TCR Primer

<400> SEQUENCE: 68
cccagtgaag agatggtttt cctta                                         25

<210> SEQ ID NO 69
<211> LENGTH: 45
<212> TYPE: DNA
<213> ORGANISM: Artificial Sequence
<220> FEATURE:
<223> OTHER INFORMATION: TCR Primer

<400> SEQUENCE: 69
gacgtgtgct cttccgatct taagtcaaat gcaaagcctg tgaac                   45

<210> SEQ ID NO 70
<211> LENGTH: 26
<212> TYPE: DNA
<213> ORGANISM: Artificial Sequence
<220> FEATURE:
<223> OTHER INFORMATION: TCR Primer

<400> SEQUENCE: 70
tgaaggtctt atcttcttga tgatgc                                        26

<210> SEQ ID NO 71
<211> LENGTH: 26
<212> TYPE: DNA
<213> ORGANISM: Artificial Sequence
<220> FEATURE:
<223> OTHER INFORMATION: TCR Primer

<400> SEQUENCE: 71
tgaaggtctt atcttcttga tgatgc                                    26

<210> SEQ ID NO 72
<211> LENGTH: 25
<212> TYPE: DNA
<213> ORGANISM: Artificial Sequence
<220> FEATURE:
<223> OTHER INFORMATION: TCR Primer

<400> SEQUENCE: 72
aggtcctgtc ctcttgatag cctta                                     25

<210> SEQ ID NO 73
<211> LENGTH: 45
<212> TYPE: DNA
<213> ORGANISM: Artificial Sequence
<220> FEATURE:
<223> OTHER INFORMATION: TCR Primer

<400> SEQUENCE: 73
gacgtgtgct cttccgatct ggaagactga ctgctcagtt tggta               45

<210> SEQ ID NO 74
<211> LENGTH: 25
<212> TYPE: DNA
<213> ORGANISM: Artificial Sequence
<220> FEATURE:
<223> OTHER INFORMATION: TCR Primer

<400> SEQUENCE: 74
ggaaaagaaa gctcccacat ttcta                                     25

<210> SEQ ID NO 75
<211> LENGTH: 45
<212> TYPE: DNA
<213> ORGANISM: Artificial Sequence
<220> FEATURE:
<223> OTHER INFORMATION: TCR Primer

<400> SEQUENCE: 75
gacgtgtgct cttccgatct tggaattgaa aagaagtcag gaaga               45

<210> SEQ ID NO 76
<211> LENGTH: 25
<212> TYPE: DNA
<213> ORGANISM: Artificial Sequence
<220> FEATURE:
<223> OTHER INFORMATION: TCR Primer

<400> SEQUENCE: 76
cctcatttcc ctgatacaaa tgcta                                     25

<210> SEQ ID NO 77
<211> LENGTH: 45
<212> TYPE: DNA
<213> ORGANISM: Artificial Sequence
<220> FEATURE:
<223> OTHER INFORMATION: TCR Primer

<400> SEQUENCE: 77
gacgtgtgct cttccgatct agaagatcag tggaagattc acagc               45

<210> SEQ ID NO 78
<211> LENGTH: 25
<212> TYPE: DNA

```
<213> ORGANISM: Artificial Sequence
<220> FEATURE:
<223> OTHER INFORMATION: TCR Primer

<400> SEQUENCE: 78
agcaggcaga tgattctcgt tattc                                    25

<210> SEQ ID NO 79
<211> LENGTH: 45
<212> TYPE: DNA
<213> ORGANISM: Artificial Sequence
<220> FEATURE:
<223> OTHER INFORMATION: TCR Primer

<400> SEQUENCE: 79
gacgtgtgct cttccgatct agaaagcagc caaatccttc agtct             45

<210> SEQ ID NO 80
<211> LENGTH: 25
<212> TYPE: DNA
<213> ORGANISM: Artificial Sequence
<220> FEATURE:
<223> OTHER INFORMATION: TCR Primer

<400> SEQUENCE: 80
gtctggaatc tctgtttgtg ttgct                                    25

<210> SEQ ID NO 81
<211> LENGTH: 45
<212> TYPE: DNA
<213> ORGANISM: Artificial Sequence
<220> FEATURE:
<223> OTHER INFORMATION: TCR Primer

<400> SEQUENCE: 81
gacgtgtgct cttccgatct gacgattaat ggcctcactt gatac             45

<210> SEQ ID NO 82
<211> LENGTH: 25
<212> TYPE: DNA
<213> ORGANISM: Artificial Sequence
<220> FEATURE:
<223> OTHER INFORMATION: TCR Primer

<400> SEQUENCE: 82
tgcagcttct tcagagagag acaat                                    25

<210> SEQ ID NO 83
<211> LENGTH: 45
<212> TYPE: DNA
<213> ORGANISM: Artificial Sequence
<220> FEATURE:
<223> OTHER INFORMATION: TCR Primer

<400> SEQUENCE: 83
gacgtgtgct cttccgatct ggaggcggaa atattaaaga caaaa             45

<210> SEQ ID NO 84
<211> LENGTH: 25
<212> TYPE: DNA
<213> ORGANISM: Artificial Sequence
<220> FEATURE:
<223> OTHER INFORMATION: TCR Primer

<400> SEQUENCE: 84
gcattgtttc cttgtttatg ctgag                                    25
```

<210> SEQ ID NO 85
<211> LENGTH: 45
<212> TYPE: DNA
<213> ORGANISM: Artificial Sequence
<220> FEATURE:
<223> OTHER INFORMATION: TCR Primer

<400> SEQUENCE: 85
gacgtgtgct cttccgatct gcatggaaga ttaattgcca caata         45

<210> SEQ ID NO 86
<211> LENGTH: 25
<212> TYPE: DNA
<213> ORGANISM: Artificial Sequence
<220> FEATURE:
<223> OTHER INFORMATION: TCR Primer

<400> SEQUENCE: 86
aagaaatccc tggagttcat gtttt         25

<210> SEQ ID NO 87
<211> LENGTH: 45
<212> TYPE: DNA
<213> ORGANISM: Artificial Sequence
<220> FEATURE:
<223> OTHER INFORMATION: TCR Primer

<400> SEQUENCE: 87
gacgtgtgct cttccgatct ctgacagctc tcgcttatac cttca         45

<210> SEQ ID NO 88
<211> LENGTH: 25
<212> TYPE: DNA
<213> ORGANISM: Artificial Sequence
<220> FEATURE:
<223> OTHER INFORMATION: TCR Primer

<400> SEQUENCE: 88
gtacagacaa atcttggggc agaaa         25

<210> SEQ ID NO 89
<211> LENGTH: 45
<212> TYPE: DNA
<213> ORGANISM: Artificial Sequence
<220> FEATURE:
<223> OTHER INFORMATION: TCR Primer

<400> SEQUENCE: 89
gacgtgtgct cttccgatct gcctgatgga tcaaatttca ctctg         45

<210> SEQ ID NO 90
<211> LENGTH: 25
<212> TYPE: DNA
<213> ORGANISM: Artificial Sequence
<220> FEATURE:
<223> OTHER INFORMATION: TCR Primer

<400> SEQUENCE: 90
tctgggccat ratrctatgt attgg         25

<210> SEQ ID NO 91
<211> LENGTH: 45
<212> TYPE: DNA
<213> ORGANISM: Artificial Sequence
<220> FEATURE:

<223> OTHER INFORMATION: TCR Primer

<400> SEQUENCE: 91
gacgtgtgct cttccgatct aatgaaacag ttccaaatcg mttct　　　　　　　　　　45

<210> SEQ ID NO 92
<211> LENGTH: 22
<212> TYPE: DNA
<213> ORGANISM: Artificial Sequence
<220> FEATURE:
<223> OTHER INFORMATION: TCR Primer

<400> SEQUENCE: 92
agtgtgccaa gtcgcttctc ac　　　　　　　　　　　　　　　　　　　　　22

<210> SEQ ID NO 93
<211> LENGTH: 42
<212> TYPE: DNA
<213> ORGANISM: Artificial Sequence
<220> FEATURE:
<223> OTHER INFORMATION: TCR Primer

<400> SEQUENCE: 93
gacgtgtgct cttccgatct ccaagtcgct tctcacctga at　　　　　　　　　　42

<210> SEQ ID NO 94
<211> LENGTH: 24
<212> TYPE: DNA
<213> ORGANISM: Artificial Sequence
<220> FEATURE:
<223> OTHER INFORMATION: TCR Primer

<400> SEQUENCE: 94
gggccccagt ttatctttca gtat　　　　　　　　　　　　　　　　　　　　24

<210> SEQ ID NO 95
<211> LENGTH: 44
<212> TYPE: DNA
<213> ORGANISM: Artificial Sequence
<220> FEATURE:
<223> OTHER INFORMATION: TCR Primer

<400> SEQUENCE: 95
gacgtgtgct cttccgatct cgccagttct ctaactctcg ctct　　　　　　　　　44

<210> SEQ ID NO 96
<211> LENGTH: 24
<212> TYPE: DNA
<213> ORGANISM: Artificial Sequence
<220> FEATURE:
<223> OTHER INFORMATION: TCR Primer

<400> SEQUENCE: 96
cagytcctcc tttggtatga cgag　　　　　　　　　　　　　　　　　　　　24

<210> SEQ ID NO 97
<211> LENGTH: 45
<212> TYPE: DNA
<213> ORGANISM: Artificial Sequence
<220> FEATURE:
<223> OTHER INFORMATION: TCR Primer

<400> SEQUENCE: 97
gacgtgtgct cttccgatct ttactgagtc aaacacggag ctagg　　　　　　　　45

<210> SEQ ID NO 98
<211> LENGTH: 45
<212> TYPE: DNA
<213> ORGANISM: Artificial Sequence
<220> FEATURE:
<223> OTHER INFORMATION: TCR Primer

<400> SEQUENCE: 98
gacgtgtgct cttccgatct ctctgagatg aatgtgagtg ccttg            45

<210> SEQ ID NO 99
<211> LENGTH: 43
<212> TYPE: DNA
<213> ORGANISM: Artificial Sequence
<220> FEATURE:
<223> OTHER INFORMATION: TCR Primer

<400> SEQUENCE: 99
gacgtgtgct cttccgatct ctgagctgaa tgtgaacgcc ttg              43

<210> SEQ ID NO 100
<211> LENGTH: 25
<212> TYPE: DNA
<213> ORGANISM: Artificial Sequence
<220> FEATURE:
<223> OTHER INFORMATION: TCR Primer

<400> SEQUENCE: 100
gagggtacca ctgacaaagg agaag                                  25

<210> SEQ ID NO 101
<211> LENGTH: 45
<212> TYPE: DNA
<213> ORGANISM: Artificial Sequence
<220> FEATURE:
<223> OTHER INFORMATION: TCR Primer

<400> SEQUENCE: 101
gacgtgtgct cttccgatct tctccagatt aaacaaacgg gagtt            45

<210> SEQ ID NO 102
<211> LENGTH: 25
<212> TYPE: DNA
<213> ORGANISM: Artificial Sequence
<220> FEATURE:
<223> OTHER INFORMATION: TCR Primer

<400> SEQUENCE: 102
actcagttgg tgagggtaca actgc                                  25

<210> SEQ ID NO 103
<211> LENGTH: 45
<212> TYPE: DNA
<213> ORGANISM: Artificial Sequence
<220> FEATURE:
<223> OTHER INFORMATION: TCR Primer

<400> SEQUENCE: 103
gacgtgtgct cttccgatct ctgatggcta caatgtctcc agatt            45

<210> SEQ ID NO 104
<211> LENGTH: 24
<212> TYPE: DNA
<213> ORGANISM: Artificial Sequence
<220> FEATURE:
<223> OTHER INFORMATION: TCR Primer

```
<400> SEQUENCE: 104
aggtaccact ggcaaaggag aagt                                          24

<210> SEQ ID NO 105
<211> LENGTH: 45
<212> TYPE: DNA
<213> ORGANISM: Artificial Sequence
<220> FEATURE:
<223> OTHER INFORMATION: TCR Primer

<400> SEQUENCE: 105
gacgtgtgct cttccgatct agtgtctcca gagcaaacac agatg                   45

<210> SEQ ID NO 106
<211> LENGTH: 24
<212> TYPE: DNA
<213> ORGANISM: Artificial Sequence
<220> FEATURE:
<223> OTHER INFORMATION: TCR Primer

<400> SEQUENCE: 106
tcagttggtg ctggtatcac tgay                                          24

<210> SEQ ID NO 107
<211> LENGTH: 45
<212> TYPE: DNA
<213> ORGANISM: Artificial Sequence
<220> FEATURE:
<223> OTHER INFORMATION: TCR Primer

<400> SEQUENCE: 107
gacgtgtgct cttccgatct gtctccagat caamcacaga ggatt                   45

<210> SEQ ID NO 108
<211> LENGTH: 25
<212> TYPE: DNA
<213> ORGANISM: Artificial Sequence
<220> FEATURE:
<223> OTHER INFORMATION: TCR Primer

<400> SEQUENCE: 108
tgctctcact gacaaaggag aagtt                                         25

<210> SEQ ID NO 109
<211> LENGTH: 44
<212> TYPE: DNA
<213> ORGANISM: Artificial Sequence
<220> FEATURE:
<223> OTHER INFORMATION: TCR Primer

<400> SEQUENCE: 109
gacgtgtgct cttccgatct aaacacagag gatttcccrc tcag                    44

<210> SEQ ID NO 110
<211> LENGTH: 25
<212> TYPE: DNA
<213> ORGANISM: Artificial Sequence
<220> FEATURE:
<223> OTHER INFORMATION: TCR Primer

<400> SEQUENCE: 110
tgctgctggt actactgaca aagaa                                         25

<210> SEQ ID NO 111
<211> LENGTH: 25
```

```
<212> TYPE: DNA
<213> ORGANISM: Artificial Sequence
<220> FEATURE:
<223> OTHER INFORMATION: TCR Primer

<400> SEQUENCE: 111
gctggtatca ctgacaaagg agaag                                            25

<210> SEQ ID NO 112
<211> LENGTH: 24
<212> TYPE: DNA
<213> ORGANISM: Artificial Sequence
<220> FEATURE:
<223> OTHER INFORMATION: TCR Primer

<400> SEQUENCE: 112
caggtcatam tgccctttay tggt                                             24

<210> SEQ ID NO 113
<211> LENGTH: 43
<212> TYPE: DNA
<213> ORGANISM: Artificial Sequence
<220> FEATURE:
<223> OTHER INFORMATION: TCR Primer

<400> SEQUENCE: 113
gacgtgtgct cttccgatct gtctgaggga tccatctcca ctc                        43

<210> SEQ ID NO 114
<211> LENGTH: 25
<212> TYPE: DNA
<213> ORGANISM: Artificial Sequence
<220> FEATURE:
<223> OTHER INFORMATION: TCR Primer

<400> SEQUENCE: 114
gacttactcc cagagtgatg ctcaa                                            25

<210> SEQ ID NO 115
<211> LENGTH: 44
<212> TYPE: DNA
<213> ORGANISM: Artificial Sequence
<220> FEATURE:
<223> OTHER INFORMATION: TCR Primer

<400> SEQUENCE: 115
gacgtgtgct cttccgatct tcgcttctct gcagagagga ctgg                       44

<210> SEQ ID NO 116
<211> LENGTH: 25
<212> TYPE: DNA
<213> ORGANISM: Artificial Sequence
<220> FEATURE:
<223> OTHER INFORMATION: TCR Primer

<400> SEQUENCE: 116
agggccmaga gtttctgact tmctt                                            25

<210> SEQ ID NO 117
<211> LENGTH: 45
<212> TYPE: DNA
<213> ORGANISM: Artificial Sequence
<220> FEATURE:
<223> OTHER INFORMATION: TCR Primer

<400> SEQUENCE: 117
```

```
gacgtgtgct cttccgatct ctgagggatc cgtctctact ctgaa        45
```

<210> SEQ ID NO 118
<211> LENGTH: 25
<212> TYPE: DNA
<213> ORGANISM: Artificial Sequence
<220> FEATURE:
<223> OTHER INFORMATION: TCR Primer

<400> SEQUENCE: 118

```
gccagagttt ctgacttatt tccag                              25
```

<210> SEQ ID NO 119
<211> LENGTH: 43
<212> TYPE: DNA
<213> ORGANISM: Artificial Sequence
<220> FEATURE:
<223> OTHER INFORMATION: TCR Primer

<400> SEQUENCE: 119

```
gacgtgtgct cttccgatct ctgagrgatc cgtctccact ctg          43
```

<210> SEQ ID NO 120
<211> LENGTH: 43
<212> TYPE: DNA
<213> ORGANISM: Artificial Sequence
<220> FEATURE:
<223> OTHER INFORMATION: TCR Primer

<400> SEQUENCE: 120

```
gacgtgtgct cttccgatct ggtctgagga tctttctcca cct          43
```

<210> SEQ ID NO 121
<211> LENGTH: 43
<212> TYPE: DNA
<213> ORGANISM: Artificial Sequence
<220> FEATURE:
<223> OTHER INFORMATION: TCR Primer

<400> SEQUENCE: 121

```
gacgtgtgct cttccgatct gagggatcca tctccactct gac          43
```

<210> SEQ ID NO 122
<211> LENGTH: 43
<212> TYPE: DNA
<213> ORGANISM: Artificial Sequence
<220> FEATURE:
<223> OTHER INFORMATION: TCR Primer

<400> SEQUENCE: 122

```
gacgtgtgct cttccgatct ctgcagagag gcctaaggga tct          43
```

<210> SEQ ID NO 123
<211> LENGTH: 25
<212> TYPE: DNA
<213> ORGANISM: Artificial Sequence
<220> FEATURE:
<223> OTHER INFORMATION: TCR Primer

<400> SEQUENCE: 123

```
tgctcagatt aggaaccatt attca                              25
```

<210> SEQ ID NO 124
<211> LENGTH: 43
<212> TYPE: DNA
<213> ORGANISM: Artificial Sequence

```
<220> FEATURE:
<223> OTHER INFORMATION: TCR Primer

<400> SEQUENCE: 124
gacgtgtgct cttccgatct aagctcaagc attttccctc aac                    43

<210> SEQ ID NO 125
<211> LENGTH: 24
<212> TYPE: DNA
<213> ORGANISM: Artificial Sequence
<220> FEATURE:
<223> OTHER INFORMATION: TCR Primer

<400> SEQUENCE: 125
aacagtgttc tgatatcgac agga                                         24

<210> SEQ ID NO 126
<211> LENGTH: 45
<212> TYPE: DNA
<213> ORGANISM: Artificial Sequence
<220> FEATURE:
<223> OTHER INFORMATION: TCR Primer

<400> SEQUENCE: 126
gacgtgtgct cttccgatct atgtcacaga ggggtactgt gtttc                  45

<210> SEQ ID NO 127
<211> LENGTH: 25
<212> TYPE: DNA
<213> ORGANISM: Artificial Sequence
<220> FEATURE:
<223> OTHER INFORMATION: TCR Primer

<400> SEQUENCE: 127
gtactggtac caacagagcc tggac                                        25

<210> SEQ ID NO 128
<211> LENGTH: 43
<212> TYPE: DNA
<213> ORGANISM: Artificial Sequence
<220> FEATURE:
<223> OTHER INFORMATION: TCR Primer

<400> SEQUENCE: 128
gacgtgtgct cttccgatct acagttccct gacttgcact ctg                    43

<210> SEQ ID NO 129
<211> LENGTH: 23
<212> TYPE: DNA
<213> ORGANISM: Artificial Sequence
<220> FEATURE:
<223> OTHER INFORMATION: TCR Primer

<400> SEQUENCE: 129
ggtatcgaca agaccyggr cat                                           23

<210> SEQ ID NO 130
<211> LENGTH: 45
<212> TYPE: DNA
<213> ORGANISM: Artificial Sequence
<220> FEATURE:
<223> OTHER INFORMATION: TCR Primer

<400> SEQUENCE: 130
gacgtgtgct cttccgatct acaaaggaga agtctcagat ggcta                  45
```

```
<210> SEQ ID NO 131
<211> LENGTH: 25
<212> TYPE: DNA
<213> ORGANISM: Artificial Sequence
<220> FEATURE:
<223> OTHER INFORMATION: TCR Primer

<400> SEQUENCE: 131
acagttgcct aaggatcgat tttct                                          25

<210> SEQ ID NO 132
<211> LENGTH: 44
<212> TYPE: DNA
<213> ORGANISM: Artificial Sequence
<220> FEATURE:
<223> OTHER INFORMATION: TCR Primer

<400> SEQUENCE: 132
gacgtgtgct cttccgatct tgtctccaga tccaagacag agaa                     44

<210> SEQ ID NO 133
<211> LENGTH: 25
<212> TYPE: DNA
<213> ORGANISM: Artificial Sequence
<220> FEATURE:
<223> OTHER INFORMATION: TCR Primer

<400> SEQUENCE: 133
cagggactgg aattgctgar ttact                                          25

<210> SEQ ID NO 134
<211> LENGTH: 44
<212> TYPE: DNA
<213> ORGANISM: Artificial Sequence
<220> FEATURE:
<223> OTHER INFORMATION: TCR Primer

<400> SEQUENCE: 134
gacgtgtgct cttccgatct ctgcagagag gctcaaagga gtag                     44

<210> SEQ ID NO 135
<211> LENGTH: 24
<212> TYPE: DNA
<213> ORGANISM: Artificial Sequence
<220> FEATURE:
<223> OTHER INFORMATION: TCR Primer

<400> SEQUENCE: 135
tctggtacag acagaccatg atgc                                           24

<210> SEQ ID NO 136
<211> LENGTH: 45
<212> TYPE: DNA
<213> ORGANISM: Artificial Sequence
<220> FEATURE:
<223> OTHER INFORMATION: TCR Primer

<400> SEQUENCE: 136
gacgtgtgct cttccgatct atcattctcy actctgagga tccar                    45

<210> SEQ ID NO 137
<211> LENGTH: 25
<212> TYPE: DNA
<213> ORGANISM: Artificial Sequence
<220> FEATURE:
<223> OTHER INFORMATION: TCR Primer
```

-continued

<400> SEQUENCE: 137
ttcgttttat gaaaagatgc agagc                                      25

<210> SEQ ID NO 138
<211> LENGTH: 45
<212> TYPE: DNA
<213> ORGANISM: Artificial Sequence
<220> FEATURE:
<223> OTHER INFORMATION: TCR Primer

<400> SEQUENCE: 138
gacgtgtgct cttccgatct actctgarga tccagccctc agaac                45

<210> SEQ ID NO 139
<211> LENGTH: 25
<212> TYPE: DNA
<213> ORGANISM: Artificial Sequence
<220> FEATURE:
<223> OTHER INFORMATION: TCR Primer

<400> SEQUENCE: 139
atcgattctt agctgaaagg actgg                                      25

<210> SEQ ID NO 140
<211> LENGTH: 46
<212> TYPE: DNA
<213> ORGANISM: Artificial Sequence
<220> FEATURE:
<223> OTHER INFORMATION: TCR Primer

<400> SEQUENCE: 140
gacgtgtgct cttccgatct cagctcaaca gttcagtgac tatcat               46

<210> SEQ ID NO 141
<211> LENGTH: 25
<212> TYPE: DNA
<213> ORGANISM: Artificial Sequence
<220> FEATURE:
<223> OTHER INFORMATION: TCR Primer

<400> SEQUENCE: 141
agacacccct gataacttcc aatcc                                      25

<210> SEQ ID NO 142
<211> LENGTH: 45
<212> TYPE: DNA
<213> ORGANISM: Artificial Sequence
<220> FEATURE:
<223> OTHER INFORMATION: TCR Primer

<400> SEQUENCE: 142
gacgtgtgct cttccgatct gaaaggactg gagggacgta ttcta                45

<210> SEQ ID NO 143
<211> LENGTH: 25
<212> TYPE: DNA
<213> ORGANISM: Artificial Sequence
<220> FEATURE:
<223> OTHER INFORMATION: TCR Primer

<400> SEQUENCE: 143
aaacaggtat gcccaaggaa agatt                                      25

<210> SEQ ID NO 144

```
<211> LENGTH: 44
<212> TYPE: DNA
<213> ORGANISM: Artificial Sequence
<220> FEATURE:
<223> OTHER INFORMATION: TCR Primer

<400> SEQUENCE: 144
gacgtgtgct cttccgatct gccgaacact tctttctgct ttct          44

<210> SEQ ID NO 145
<211> LENGTH: 25
<212> TYPE: DNA
<213> ORGANISM: Artificial Sequence
<220> FEATURE:
<223> OTHER INFORMATION: TCR Primer

<400> SEQUENCE: 145
aaacattgca gttgattcag ggatg                               25

<210> SEQ ID NO 146
<211> LENGTH: 45
<212> TYPE: DNA
<213> ORGANISM: Artificial Sequence
<220> FEATURE:
<223> OTHER INFORMATION: TCR Primer

<400> SEQUENCE: 146
gacgtgtgct cttccgatct attttcagct aagtgcctcc caaat         45

<210> SEQ ID NO 147
<211> LENGTH: 25
<212> TYPE: DNA
<213> ORGANISM: Artificial Sequence
<220> FEATURE:
<223> OTHER INFORMATION: TCR Primer

<400> SEQUENCE: 147
catagatgag tcaggaatgc caaag                               25

<210> SEQ ID NO 148
<211> LENGTH: 44
<212> TYPE: DNA
<213> ORGANISM: Artificial Sequence
<220> FEATURE:
<223> OTHER INFORMATION: TCR Primer

<400> SEQUENCE: 148
gacgtgtgct cttccgatct cacagctgaa agacctaacg gaac          44

<210> SEQ ID NO 149
<211> LENGTH: 27
<212> TYPE: DNA
<213> ORGANISM: Artificial Sequence
<220> FEATURE:
<223> OTHER INFORMATION: TCR Primer

<400> SEQUENCE: 149
tcagaaagga gatatagctg aagggta                             27

<210> SEQ ID NO 150
<211> LENGTH: 45
<212> TYPE: DNA
<213> ORGANISM: Artificial Sequence
<220> FEATURE:
<223> OTHER INFORMATION: TCR Primer

<400> SEQUENCE: 150
```

```
gacgtgtgct cttccgatct attttctgct gaatttccca aagag          45
```

<210> SEQ ID NO 151
<211> LENGTH: 25
<212> TYPE: DNA
<213> ORGANISM: Artificial Sequence
<220> FEATURE:
<223> OTHER INFORMATION: TCR Primer

<400> SEQUENCE: 151

```
caaggccaca tacgagcaag gcgtc                                25
```

<210> SEQ ID NO 152
<211> LENGTH: 43
<212> TYPE: DNA
<213> ORGANISM: Artificial Sequence
<220> FEATURE:
<223> OTHER INFORMATION: TCR Primer

<400> SEQUENCE: 152

```
gacgtgtgct cttccgatct gtctctcggg agaagaagga atc            43
```

<210> SEQ ID NO 153
<211> LENGTH: 26
<212> TYPE: DNA
<213> ORGANISM: Artificial Sequence
<220> FEATURE:
<223> OTHER INFORMATION: TCR Primer

<400> SEQUENCE: 153

```
tcagaaagca gaaataatca atgagc                               26
```

<210> SEQ ID NO 154
<211> LENGTH: 45
<212> TYPE: DNA
<213> ORGANISM: Artificial Sequence
<220> FEATURE:
<223> OTHER INFORMATION: TCR Primer

<400> SEQUENCE: 154

```
gacgtgtgct cttccgatct gacaagtttc tcatcaacca tgcaa          45
```

<210> SEQ ID NO 155
<211> LENGTH: 26
<212> TYPE: DNA
<213> ORGANISM: Artificial Sequence
<220> FEATURE:
<223> OTHER INFORMATION: TCR Primer

<400> SEQUENCE: 155

```
gaggagatct aactgaaggc tacgtg                               26
```

<210> SEQ ID NO 156
<211> LENGTH: 26
<212> TYPE: DNA
<213> ORGANISM: Artificial Sequence
<220> FEATURE:
<223> OTHER INFORMATION: TCR Primer

<400> SEQUENCE: 156

```
gaggagatct aactgaaggc tacgtg                               26
```

<210> SEQ ID NO 157
<211> LENGTH: 24
<212> TYPE: DNA

```
<213> ORGANISM: Artificial Sequence
<220> FEATURE:
<223> OTHER INFORMATION: TCR Primer

<400> SEQUENCE: 157
caagaaacgg agatgcacaa gaag                                    24

<210> SEQ ID NO 158
<211> LENGTH: 45
<212> TYPE: DNA
<213> ORGANISM: Artificial Sequence
<220> FEATURE:
<223> OTHER INFORMATION: TCR Primer

<400> SEQUENCE: 158
gacgtgtgct cttccgatct aggagaaggg gctatttctt ctcag             45

<210> SEQ ID NO 159
<211> LENGTH: 27
<212> TYPE: DNA
<213> ORGANISM: Artificial Sequence
<220> FEATURE:
<223> OTHER INFORMATION: TCR Primer

<400> SEQUENCE: 159
cggttgatct attactcctt tgatgtc                                 27

<210> SEQ ID NO 160
<211> LENGTH: 45
<212> TYPE: DNA
<213> ORGANISM: Artificial Sequence
<220> FEATURE:
<223> OTHER INFORMATION: TCR Primer

<400> SEQUENCE: 160
gacgtgtgct cttccgatct attctcatct caatgcccca agaac             45

<210> SEQ ID NO 161
<211> LENGTH: 25
<212> TYPE: DNA
<213> ORGANISM: Artificial Sequence
<220> FEATURE:
<223> OTHER INFORMATION: TCR Primer

<400> SEQUENCE: 161
aattccacag agaagggaga tcttt                                   25

<210> SEQ ID NO 162
<211> LENGTH: 43
<212> TYPE: DNA
<213> ORGANISM: Artificial Sequence
<220> FEATURE:
<223> OTHER INFORMATION: TCR Primer

<400> SEQUENCE: 162
gacgtgtgct cttccgatct gacaggcaca ggctaaattc tcc               43

<210> SEQ ID NO 163
<211> LENGTH: 25
<212> TYPE: DNA
<213> ORGANISM: Artificial Sequence
<220> FEATURE:
<223> OTHER INFORMATION: TCR Primer

<400> SEQUENCE: 163
actgggagca ctgaaaaagg agata                                   25
```

<210> SEQ ID NO 164
<211> LENGTH: 45
<212> TYPE: DNA
<213> ORGANISM: Artificial Sequence
<220> FEATURE:
<223> OTHER INFORMATION: TCR Primer

<400> SEQUENCE: 164
gacgtgtgct cttccgatct agtctccaga ataaggacgg agcat    45

<210> SEQ ID NO 165
<211> LENGTH: 25
<212> TYPE: DNA
<213> ORGANISM: Artificial Sequence
<220> FEATURE:
<223> OTHER INFORMATION: TCR Primer

<400> SEQUENCE: 165
ttcaatgaat gttgaggtga ctgat    25

<210> SEQ ID NO 166
<211> LENGTH: 45
<212> TYPE: DNA
<213> ORGANISM: Artificial Sequence
<220> FEATURE:
<223> OTHER INFORMATION: TCR Primer

<400> SEQUENCE: 166
gacgtgtgct cttccgatct ctctgagggg tatcatgttt cttga    45

<210> SEQ ID NO 167
<211> LENGTH: 27
<212> TYPE: DNA
<213> ORGANISM: Artificial Sequence
<220> FEATURE:
<223> OTHER INFORMATION: TCR Primer

<400> SEQUENCE: 167
cggctgatct atttctcata tgatgtt    27

<210> SEQ ID NO 168
<211> LENGTH: 46
<212> TYPE: DNA
<213> ORGANISM: Artificial Sequence
<220> FEATURE:
<223> OTHER INFORMATION: TCR Primer

<400> SEQUENCE: 168
gacgtgtgct cttccgatct caaagtctct cgaaaagaga agagga    46

<210> SEQ ID NO 169
<211> LENGTH: 22
<212> TYPE: DNA
<213> ORGANISM: Artificial Sequence
<220> FEATURE:
<223> OTHER INFORMATION: TCR Primer

<400> SEQUENCE: 169
gacactgatc gcaactgcaa at    22

<210> SEQ ID NO 170
<211> LENGTH: 44
<212> TYPE: DNA
<213> ORGANISM: Artificial Sequence
<220> FEATURE:

```
<223> OTHER INFORMATION: TCR Primer

<400> SEQUENCE: 170
gacgtgtgct cttccgatct aagaaggagc gcttctccct gatt                    44

<210> SEQ ID NO 171
<211> LENGTH: 23
<212> TYPE: DNA
<213> ORGANISM: Artificial Sequence
<220> FEATURE:
<223> OTHER INFORMATION: TCR Primer

<400> SEQUENCE: 171
gcctccagct gctcttctac tcc                                           23

<210> SEQ ID NO 172
<211> LENGTH: 42
<212> TYPE: DNA
<213> ORGANISM: Artificial Sequence
<220> FEATURE:
<223> OTHER INFORMATION: TCR Primer

<400> SEQUENCE: 172
gacgtgtgct cttccgatct cgcccaaacc taacattctc aa                      42
```

METHODS AND COMPOSITIONS FOR DETECTING SINGLE T CELL RECEPTOR AFFINITY AND SEQUENCE

The present application claims the priority benefit of U.S. Provisional Application Ser. No. 62/320,801, filed Apr. 11, 2016, the entire contents of which is hereby incorporated by reference.

The present application is a national phase application under 35 U.S.C. § 371 of International Application No. PCT/US2017/026286, filed Apr. 6, 2017, which claims the priority benefit of U.S. Provisional Application Ser. No. 62/320,801, filed Apr. 11, 2016, the entire contents of each of which is hereby incorporated by reference.

INCORPORATION OF SEQUENCE LISTING

The sequence listing that is contained in the file named "UTSBP1093US_ST25.txt", which is 32 KB (as measured in Microsoft Windows®) and was created on Oct. 9, 2018, is filed herewith by electronic submission and is incorporated by reference herein.

BACKGROUND OF THE INVENTION

1. Field of the Invention

The present invention relates generally to the fields of immunology and medicine. More particularly, it concerns methods of determining T cell receptor affinity and sequence.

2. Description of Related Art

The immune system generates a diverse repertoire of $CD8^+$ T cells each bearing a unique T cell receptor (TCR), which recognizes specific peptide antigens bound to major histocompatibility complex (pMHC). The affinity of the T cell receptor (TCR) interaction with its ligand, peptide bound to major histocompatibility complex (pMHC), is an important parameter for T cells to discriminate agonist ligand from partial-agonist and non-agonist ligands (Davis et al., 2007). TCR affinity impacts the downstream fate (King et al., 2012) and functional capacity (Aleksic et al., 2010) of T cells by affecting TCR signaling strength (Huang et al., 2010) and proliferation rates (Zehn et al., 2009). $CD8^+$ cytotoxic T Lymphocytes (CTLs) can directly kill pathogen infected host cells as well as cancer cells. Thus, the ability to track TCR affinities of antigen-specific CTLs within an individual can provide important information on the quality of an immune response and for selecting the optimum T cells for adoptive immunotherapies in cancer and persistent viral infections (Restifo et al., 2012; Heslop et al., 1996; Nauerth et al., 2013).

While the TCR affinity is an important parameter in T cell profiling, the current "gold standard" for measuring TCR-pMHC affinity by plasmon resonance (SPR) is laborious. SPR requires the expression of recombinant soluble TCR protein and is not feasible for analyzing large and polyclonal TCR repertoires. Current technologies for characterizing the TCR-pMHC kinetics in situ have limited applicability to primary human samples (Nauerth et al., 2013; Frost et al., 2015). These methods require either a high frequency (e.g., about 20% of the total T cells) or a high count (e.g., about 10,000/μl of antigen-specific CTLs), neither of which are usually obtainable in humans from a single blood draw. This is because antigen-specific CTLs responsive to most epitopes exist on a frequency of one in $10^4$-$10^7$ of total CTLs (Yu et al., 2015). In addition, these methods cannot easily link TCR biophysical binding parameters to its sequence, which is another piece of important information about TCR. As a result, a method for profiling TCR affinity and sequence from a small number of T cells is needed.

SUMMARY OF THE INVENTION

Embodiments of the present invention provide methods for measuring T cell receptor (TCR) affinity and obtaining TCR sequence comprising: (a) obtaining a population of antigen-specific T cells; (b) performing a micropipette adhesion assay on said antigen-specific T cells, thereby measuring the two-dimensional (2D) TCR affinity to a peptide-major histocompatibility complex (pMHC); and (c) sequencing the TCR by paired TCRα/TCRβ sequencing, thereby obtaining the sequence of said TCR. In certain aspects, the population of antigen-specific T cells comprises $CD8^+$ cytotoxic T Lymphocytes (CTLs). In some aspects, the population of antigen-specific T cells comprises less than 200 T cells. In particular aspects, the population of antigen-specific T cells comprises less than 100 T cells.

In some aspects, step (a) comprises antigen-specific T cell isolation from a starting population of T cells using pMHC-tagged streptamers. In certain aspects, antigen-specific T cell isolation comprises: (a) staining the starting population of T cells with pMHC-tagged streptamers; (b) sorting for the streptamer-bound T cells; and (c) dissociating the streptamers from the T cells, thereby obtaining a population of antigen-specific T cells. In some aspects, dissociating comprises incubating the streptamer-bound T cells in a dissociation buffer comprising biotin. In some aspects, the concentration of the biotin is 1 mM to 15 mM. In some aspects, the concentration of the biotin is 1 mM to 5 mM, 2 mM to 7 mM, 3 mM to 6 mM, 4 mM to 7 mM, 5 mM to 9 mM, 6 mM to 10 mM, 7 mM to 12 mM, 9 mM to 11 mM, 8 mM to 12 mM, 10 mM to 14 mM, or 12 mM to 15 mM. In some aspects, the dissociation buffer further comprises sodium azide. In some aspects, the concentration of the sodium azide is 0.05 percent mass-by-mass to 0.5 percent mass-by-mass. In some aspects, the concentration of the sodium azide is 0.05% to 0.3%, 0.1% to 0.4%, 0.2% to 0.3%, 0.3% to 0.4%, or 0.4% to 0.5%. In some aspects, the sodium azide prevents premature T cell activation. In certain aspects, the T cells are incubated for about 15 minutes to about 90 minutes. In certain aspects, the T cells are incubated for 15 min to 30 min, 20 min to 35 min, 40 min to 50 min, 45 min to 60 min, 50 min to 70 min, 60 min to 80 min, or 75 min to 90 min. In some aspects, the antigen-specific T cell isolation is at 3° C. to 5° C. In some aspects, the antigen-specific T cell isolation is at about 4° C.

In certain aspects, step (a) comprises in vitro clonal expansion of an antigen-specific T cell. In some aspects, in vitro clonal expansion comprises co-culturing a population of polyclonal T cells with antigen presenting cells loaded with antigen peptide. In certain aspects, in vitro clonal expansion comprises activating a population of polyclonal T cells with CD3 and CD28.

In some aspects, the starting population of T cells is obtained from a patient sample or healthy blood donor sample. In certain aspects, the patient sample or healthy blood donor sample is peripheral blood. In some aspects, the patient sample comprises tumor infiltrating lymphocytes (TILs).

In certain aspects, the antigen is a tumor associated self-antigen, tumor neo-antigen or viral antigen. For example, the tumor associated self-antigen is tEGFR, Her2, CD19, CD20, CD22, mesothelin, CEA, CD23, CD24, CD30, CD33, CD38, CD44, EGFR, EGP-2, EGP-4, EPHa2, ErbB2, FBP, MAGE-A1, MUC1, NY-ESO-1, or MART-1. In some aspects, the viral antigen is HCV. For example, the HCV antigen binds to HLA-A2 KLVALGINAV (SEQ ID NO: 1).

In some aspects, the population of antigen-specific T cells is transferred to a microscope chamber before step (b). In certain aspects, step (b) comprises contacting the antigen-specific T cells with red blood cells coated with agonist pMHC and measuring adhesion frequency. For example, the contacting is for 4 seconds. In some aspects, the adhesion frequency is between 30% and 80%. In some aspects, the adhesion frequency is between 40% and 60%. In some aspects, the adhesions frequency is between 50% and 70%, such as between 60% and 70%. In some aspects, the method further comprises measuring the TCR and pMHC site density. In certain aspects, the 2D affinity is calculated from the adhesion probability and site density. In some aspects, the method further comprises estimating that variance associated with the 2D TCR affinity measurement comprising: (a) measuring the standard deviation of TCR site density fluctuation between T cells by measuring the adhesion frequencies of one red blood cell (RBC) coated with anti-TCR antibody against multiple T cells; (b) measuring the standard deviation of pMHC site density fluctuation between RBCs by measuring the adhesion frequencies of one antigen-specific T cell against multiple RBCs coated with pMHC; and (c) measuring the standard deviation of TCR site density fluctuation on the surface of one T cell by measuring the adhesion frequencies of one RBC coated with anti-TCR antibody against multiple areas of one T cell.

In certain aspects, step (c) comprises transferring the antigen-specific T cells individually by micropipette into lysis buffer for reverse transcription, PCR amplification of TCR and next-generation sequencing. In some aspects, the paired TCRα/TCRβ sequencing is performed on single antigen-specific T cells. In some aspects, the method further comprises separating reads according to cell barcodes. In certain aspects, the method further comprises clustering reads based on sequence similarity. In some aspects, the TCR affinity and sequence correlate with CTL lysis capacity. In some aspects, the TCR affinity is obtained and TCR sequence is amplified in less than 48 hours. In certain aspects, the TCR affinity is obtained and TCR sequence is amplified in less than 24 hours.

A further embodiment provides a nucleic acid encoding a high affinity functional TCR identified by the methods of the embodiments.

Another embodiment provides a host cell comprising the nucleic acid of the embodiments. In some aspects, the host cell is a peripheral blood lymphocyte. In certain aspects, the host cell is a human cell. In some aspects, the host cell is a T cell. For example, the T cell is a CD4 or CD8 positive T-cell.

In yet another embodiment, there is provided a pharmaceutical composition comprising host cells provided herein.

Further embodiments provide a method of treating a viral infection in a subject comprising adoptive T cell transfer of the pharmaceutical composition of the embodiments. In some aspects, the host cells are HCV- or CMV-specific T cells.

Another embodiment provides a method of monitoring the TCR repertoire of a subject comprising obtaining TCR affinity and sequence by the methods provided herein. In some aspects, the patient has been treated with an immunotherapy. In certain aspects, the immunotherapy is a monoclonal antibody. For example, the monoclonal therapy is ipilimumab, In yet another embodiment, there is provided a method of treating cancer in a subject comprising adoptive T cell transfer of the pharmaceutical composition comprising host cells provided herein. In some aspects, the host cells are CTLs. In certain aspects, the host cells are autologous to the subject. In some aspects, the method further comprises lymphodepletion of the subject prior to the adoptive T cell transfer. In some aspects, the method comprises administration of cyclophosphamide and/or fludarabine. In some aspects, the method further comprises administering at least one additional therapeutic agent. For example, the at least one additional therapeutic agent is chemotherapy, immunotherapy, surgery, radiotherapy, or biotherapy. In some aspects, the cancer is bladder cancer, breast cancer, clear cell kidney cancer, head/neck squamous cell carcinoma, lung squamous cell carcinoma, melanoma, non-small-cell lung cancer (NSCLC), ovarian cancer, pancreatic cancer, prostate cancer, renal cell cancer, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL). For example, the cancer is melanoma.

A further embodiment provides a method for measuring the two-dimensional (2D) TCR affinity to a peptide-major histocompatibility complex (pMHC) comprising performing a micropipette adhesion assay on antigen-specific T cells, wherein the adhesion frequency is between 30% and 80%. In some aspects, the method comprises contacting the antigen-specific T cells with red blood cells coated with agonist pMHC and measuring adhesion frequency. In certain aspects, the method further comprises measuring the TCR and pMHC site density.

In some aspects, the present disclosure provides methods of assessing health in a subject. For example, a measure of TCR affinity distribution may be used to assess the health of a subject. For example, the TCR affinity distribution to the HCV peptide antigen skews to low T cell affinity with increased age. Thus, in some aspects, a decrease in TCR affinity distribution may indicate poor health (e.g., elderly donor) or diminished protection against infection.

In some embodiments, TCR affinity distribution can be used as a donor signature. For example, the TCR affinity distribution is consistent from multiple blood draws within the same donor; however, the TCR affinity distribution can differ between donors. Accordingly, in some aspects, the TCR affinity distribution can be used as a unique signature for a donor.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1D: Overview of the iTAST method. (A) A human blood sample is enriched for CD8$^+$ streptamer$^+$ T cells, sorted using flow cytometry (B), which then undergo streptamer dissociation by addition of excess biotin. (C) T cells are affinity-tested using micropipette adhesion assay, and then picked for paired single-cell TCR sequencing (D).

FIGS. 5A-5D: Analysis of the primary HCV-specific CTL repertoire in HCV-seronegative blood donors using iTAST. (A) Single-cell 2D affinity distribution of primary polyclonal HCV-specific CTLs within 12 HCV seronegative samples from 9 donors. Numbers indicate different donors and letters indicate separate blood draws from the same donor. Bar indicates median value. 2D affinities transformed by $\log_{10}$ for t-test in 4A-B (N=63), ANOVA in 5A-C (N=54), and t-test in aggregate 2D affinities from donor 4 and 5 (N=117). Two-tailed test is used in all cases. (B) Relation of single-cell 2D affinity with the number of pMHCs required to form one TCR-pMHC bond at 4 seconds of contact. (C) Median single-cell 2D affinity for each unique donor from FIG. 5A. Samples derived from the same donor were aggregated prior to calculation. (N=9, two-tailed Mann-Whitney U Test). (D) TCRα and TCRβ V-gene usage of CTLs from sample 4B, 5A, 6, and 7 in FIG. 5A.

Figure 2A:
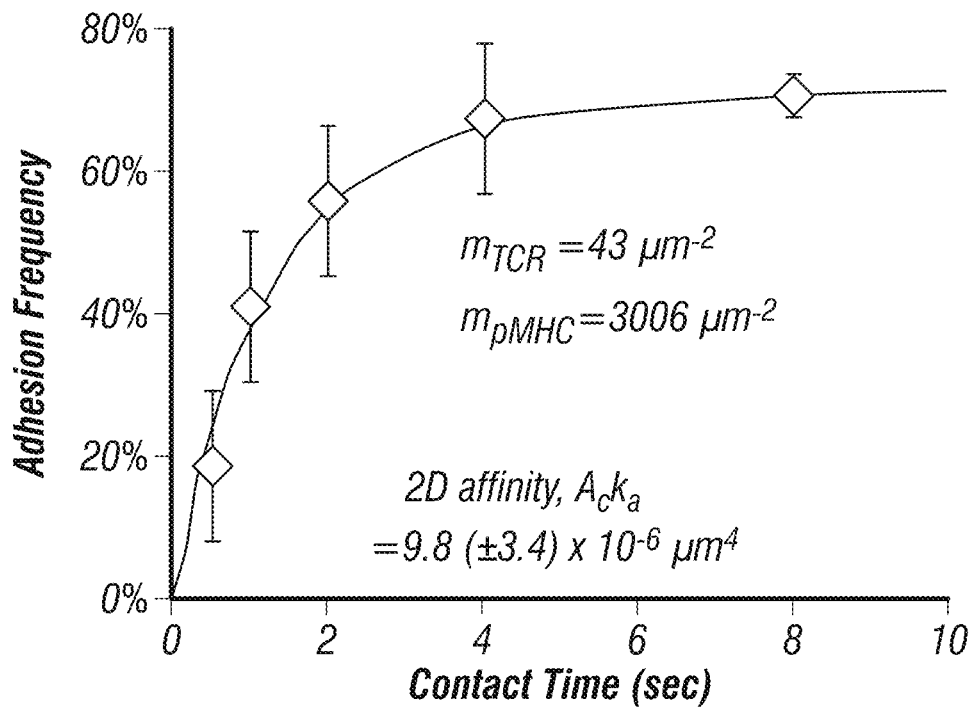
FIGS. 2A-2E: Verification of single-cell 2D affinity measurement by iTAST. (A) Adhesion curve for an HCV-specific CTL clone against HLA-A2-CD8mut/HCV. (B) TCR expression of a HCV-specific CTL, and its expression after streptamer staining and dissociation. (C) TCR expression of CTLs that was stained with phenotypic antibodies (CD27, CD45RA, CD57, CXCR3, CD95, CD45RO, and CCR7) for 3 hours at room temperature to mimic the environment for single-cell 2D affinity measurement. (D) Error analysis of factors associated with single-cell 2D affinity measurement. Factor I, T cell to T cell variation of TCR site density assessed by using one TCR antibody conjugated RBC against multiple primary CTLs, each point indicates one T cell. Factor II, variation of TCR site density in different areas on the same T cell assessed by using one TCR antibody conjugated RBC against different areas of one T cell, each point indicates one area of the same T cell (two T cells tested). Although the absolute adhesion frequencies are different between these two T cells, the variations of different areas of one T cell are similar between these two T cells. Factor III, RBC to RBC variation of MHC site density assessed by using one HCV-specific CTL clone against multiple HLA-A2-CD8mut/HCV coated RBCs, each point indicates one RBC. (E) Simulation of coefficient of variation at different adhesion frequency values using values measured from FIG. 2D.

$$\sigma^2 = \sigma^2_{binom} + \sigma^2_{Tcell\text{-}Tcell} + \sigma^2_{Tcell\_surface} + \sigma^2_{RBC\text{-}RBC}$$

$\sigma_{binom}$ refers to the intrinsic variability of a Bernoulli process. $\sigma_{Tcell\text{-}Tcell}$ refers to the TCR site density fluctuations between T cells. $\sigma_{Tcell\_surface}$ refers to variations in TCR site density across one T cell's surface. $\sigma_{RBC\text{-}RBC}$ refers to variations in pMHC site density between red blood cells (RBC). The errors are additive because each error is independent of the other. The $\sigma_{Tcell\text{-}Tcell}$ variation was isolated by using one RBC coated with biotinylated TCR antibody and measuring its adhesion frequency against multiple primary CD8+ T cells (condition (i) in panel A and B). $\sigma T_{cell\_surface}$ is isolated by measuring the adhesion frequency of one RBC against one T cell at multiple areas of the T cell, performed by releasing and re-aspirating the T cell at a different location (condition (iia,b) in panel a and b). Lastly, $\sigma_{RBC\text{-}RBC}$ is isolated by measuring the adhesion frequency of one HCV-specific T cell against multiple RBCs coated with the cognate pMHC (condition (iii) in panel a and b). (C) Just like TCR-pMHC interaction, the anti-TCR antibody-TCR interaction is also bimolecular. (D) Simulation of coefficient of variation of 2D affinity at various values of Pa using the measured variances FIGS. 13A-13H: Gating Strategy for Sorting HCV-streptamer+ T Cells. Starting from fresh LRS, the sample is first enriched for CD8+ T cells via ROSETTESEP™, and then further enriched for antigen-specific T cells via magnetic enrichment, following procedures outlined in Example 2. This procedure produces two samples; an enriched fraction contained the majority of the antigen-specific CD8+ T cells, as well as a flow-through fraction. Starting from the enriched fraction, gates are first set for single cell lymphocytes (A and B). Counting beads are added prior to analysis to allow counting of the antigen-specific T cell frequency. Although the enriched fraction is a subset of a CD8+ T cell enriched sample, a minority of other cell populations still exists. As such, CD8+ T cells are chosen using negative selection using markers for macrophages, neutrophils, natural killer cells, CD4+ T cells, and B cells (C) Anti-CD8 antibody is not added due to its tendency to activate T cells and alter the T cell receptor expression level. In the majority of these experiments, an enrichment of dead cells was observed using the magnetic enrichment procedure, and hence 7-AAD is always used to discern dead populations (c). Afterwards, the antigen-specific T cells are gated (D); the gating threshold is set by using the flow-through from the same sample, which has been stained with the same panel as the enriched fraction but should not contain streptamer labeled cells (E). Naïve antigen-specific T cells are isolated based on positive expression of CCR7, CD45RA, and CD27 (F and G). The frequency of HCV-specific CD8+ T cells in four HCV-seronegative human samples (H) is calculated as follows:

$$\text{frequency} = \frac{\# \text{ streptamer}^+ \text{ cells} * \frac{\# \text{ beads counted}}{\text{Theoretical } \# \text{ beads added}}}{\text{total } CD8^+ \text{ T cell count}}$$

Total CD8 T cell count is determined by measuring the fraction of CD8 in the flowthrough using CD8 and TCR antibodies, and multiplying that by the total live cell count of flowthrough by Cellometer.

Figure 2B:
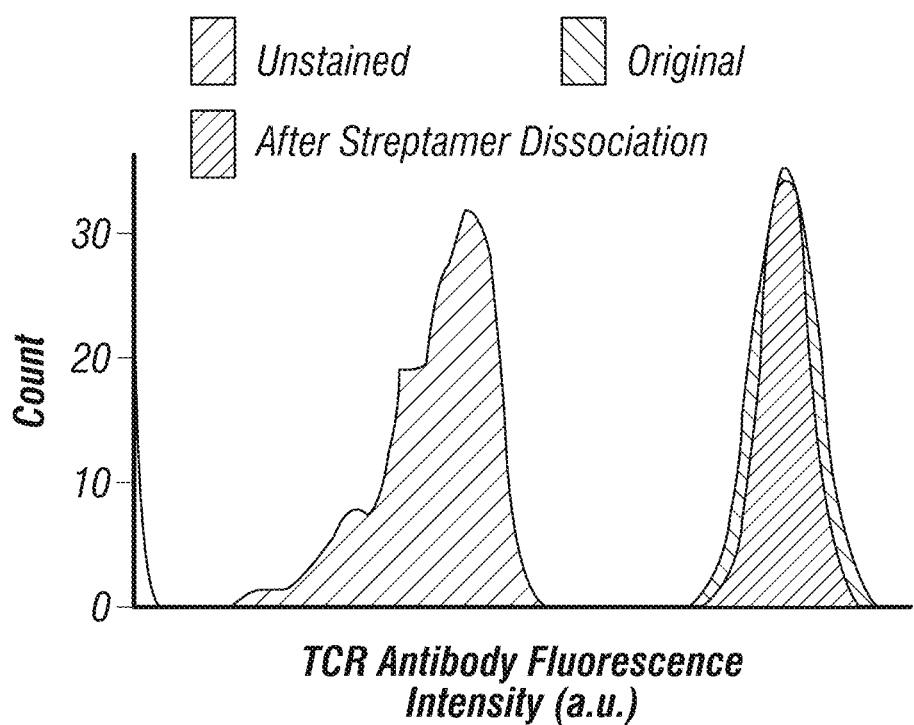
Figure 2C:
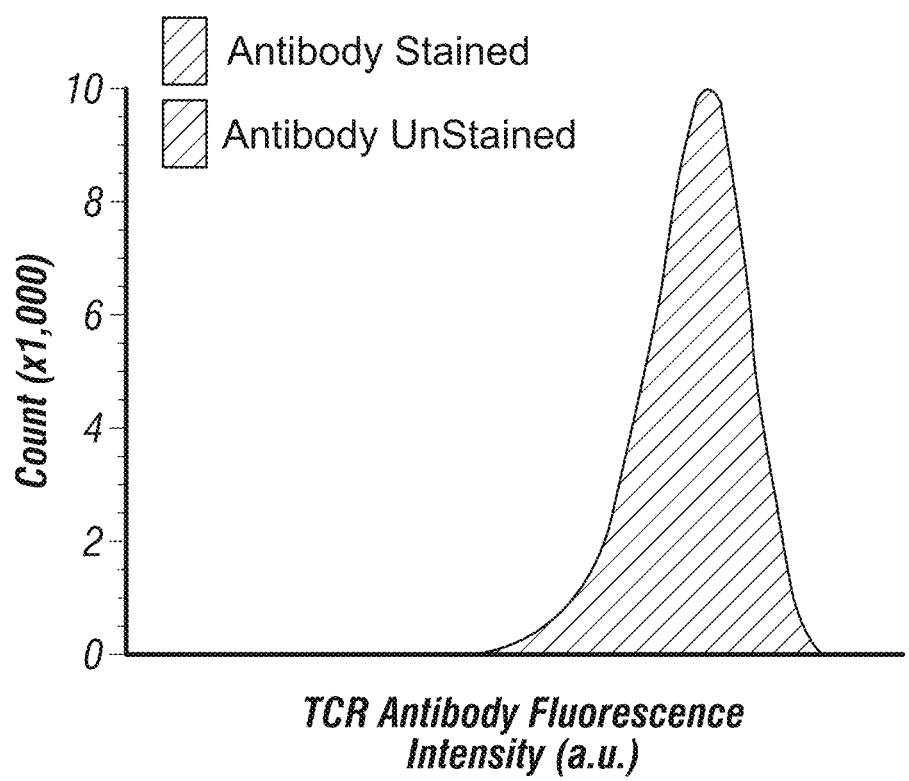
Figure 2E:
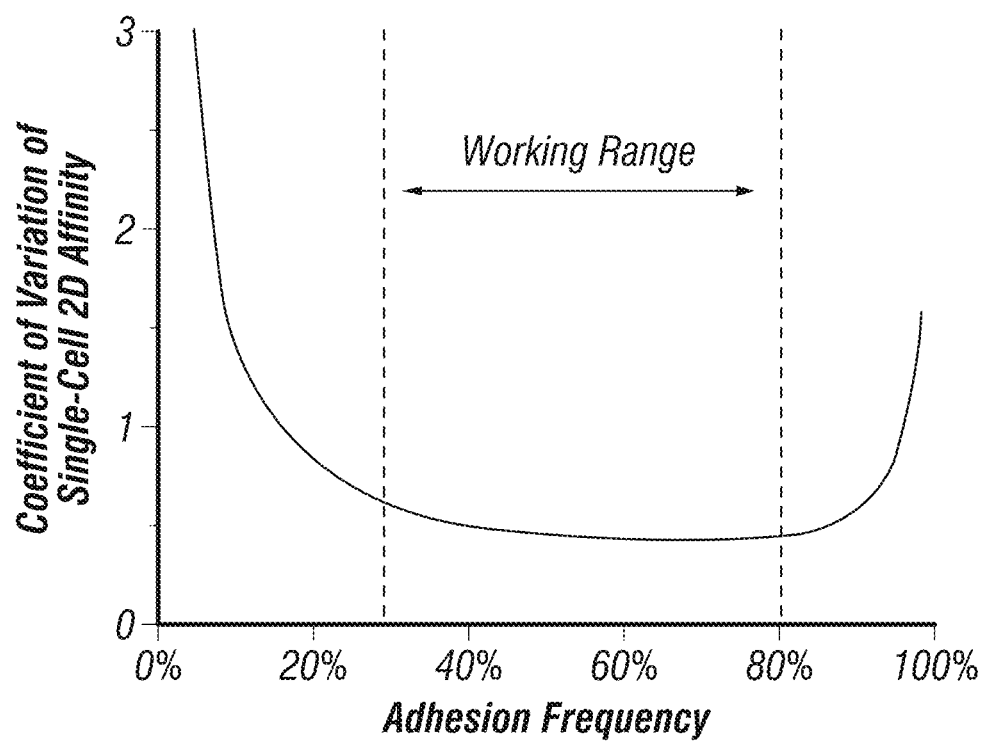
Figures 14A, 14B, 15A, 15B:
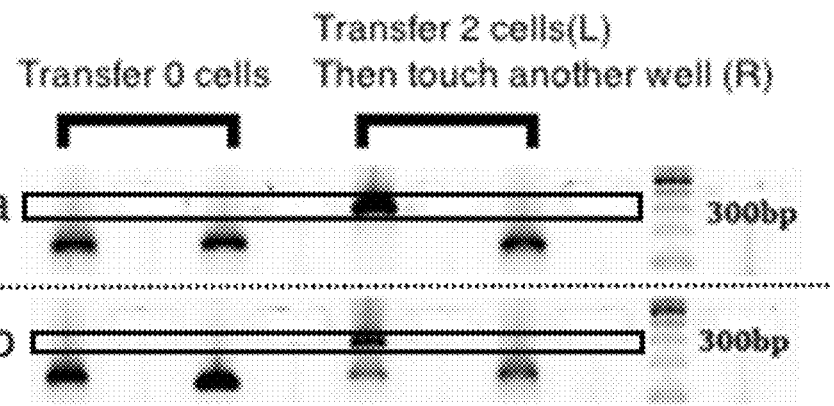

FIGS. 14A-14B: There is a dependence on the proportion of high affinity T cells and patient age. (A) From the primary 2D affinities of the 3 patients, a contingency table is created by grouping cells from the older donor 1 and 2 and compared against younger donor 3. A cutoff of $2 \times 10^5$ μm$^4$ 2 D affinity is used to categorize low and high affinity as this represents the threshold of in vitro T cell functionality (FIG. 2C). A significant dependence was found between age and the proportion of low and high affinity T cells (p<0.005, Pearson's Chi-Squared Test). (B) Frequency of the HCV-specific CTLs in the four samples and the percent of naïve cells within them as measured positive expression of CCR7, CD45RA, and CD27.

FIGS. 15A-15B: Amplification efficiency of affinity-tested cells from donor A and B. (A) Amplification efficiency of TCRα and TCRβ chains from Donor A and B. (B) In another experiment, the T cell transfer pipette was first dipped into the chamber to simulate cell picking and then dipped into lysis media (B, left) or two cells were aspirated by transfer pipette, injected into one tube, and then the pipette was immediately dipped into a second tube to test possible carry-over contamination (B, right).

Figures 16A, 16B, 16C:
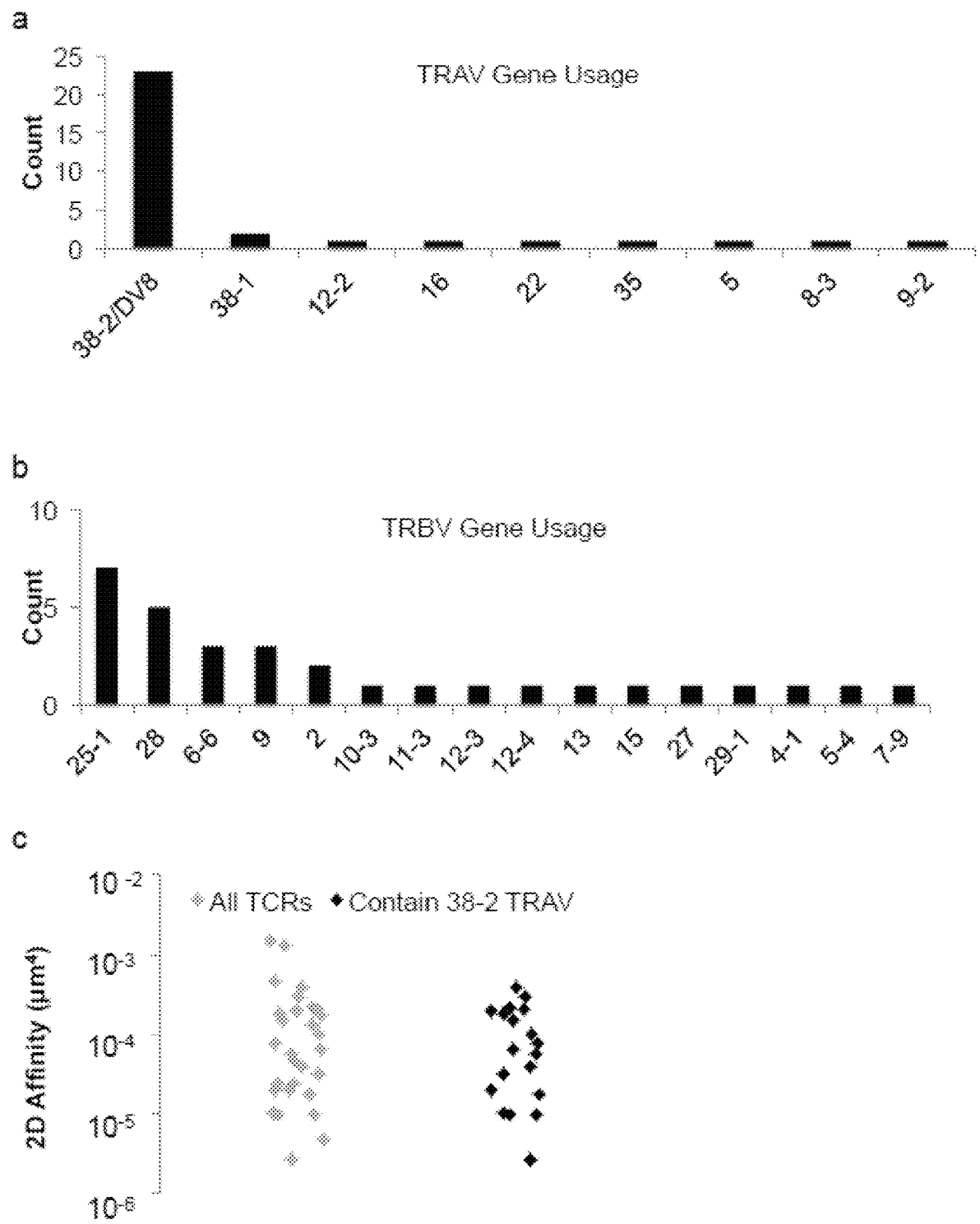

FIGS. 16A-16C: TCRα and TCRβ gene usage from donor A and B. (A,B) The distribution of TCRα and TCRβ genes among cells from donor A and B with successful paired TCRαβ amplification. (C) Affinity range comparison between all CTLs and those containing TRAV38-2.

Figure 17:
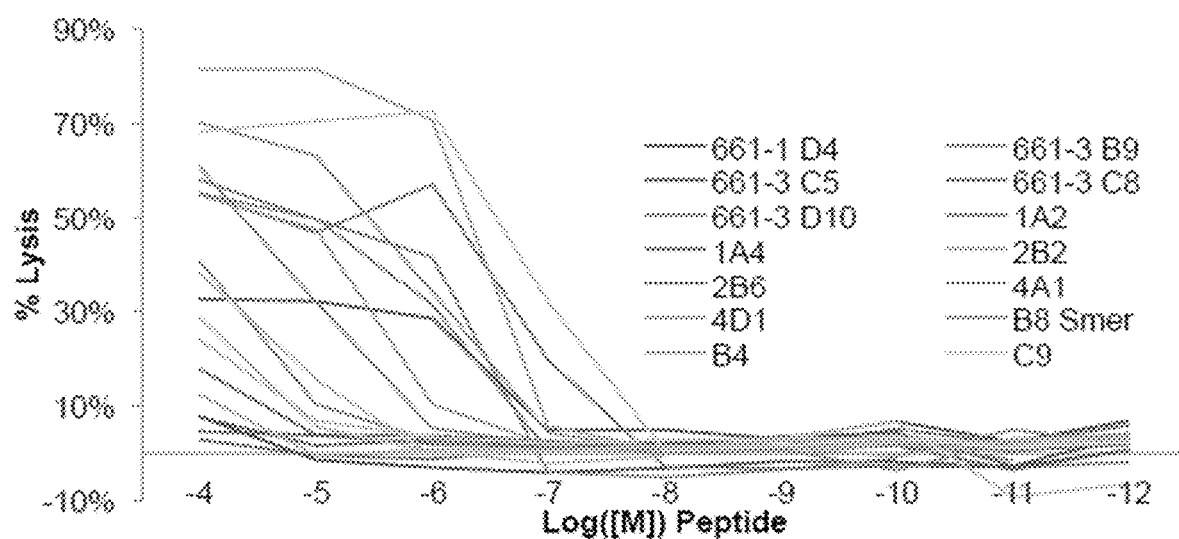

FIG. 17: Peptide titration curves of 14 selected HCV-specific clones. HCV-specific CD8+ T cell clones were washed three times with CTL media (RPMI, 10% v/v FBS, 4% v/v human serum, 1× Penicillin-Streptomycin-Amphotericin). JY cells were washed twice in CTL media, followed by addition of $10^4$-$10^{-12}$ HCV peptide and incubated for 4 hours at 37° C., and followed by two more washes in CTL media. $6\times10^4$ T cells were incubated with $6\times10^3$ JY cells in each well, with triplicates for each peptide dilution.

DESCRIPTION OF ILLUSTRATIVE EMBODIMENTS

The present disclosure overcomes challenges associated with current technologies by providing a method for obtaining the T Cell Receptor (TCR) affinity to peptide major histocompatibility complex (MHC) molecules on single T cells, such as CD8+ CTLs. The present disclosure also describes a method to obtain the paired TCRα/TCRβ sequence information from the affinity tested single T cells. The combined method of obtaining TCR affinity and sequence of antigen-specific T cells is accordingly referred to herein as the In Situ T Cell Receptor Affinity and Sequence Test (iTAST) method.

In one method, peripheral blood mononuclear cells (PBMC) that are enriched for CD8+ T cells are incubated with fluorescence-conjugated MHC I STREPTAMERS® bearing antigen-derived peptides. The MHC I STREPTAMERS® bind to the TCR of T cells that are specific for the given antigen. The cells that are positively stained are sorted into biotin-containing buffer using Fluorescence Activated Flow Cytometry. The biotin dissociates the streptamers from the cell surface, allowing the TCR of the T cells to remain free and unbound. The sorted T cells are then tested for their TCR affinity using the micropipette adhesion assay, and then transferred using a micropipette into cell lysis buffer. The picked single T cell is lysed and reverse transcribed with TCRα/β constant region primers. Then, the cDNA is amplified by the same constant region primer and multiplexed variable region primers. The first PCR product is further amplified with a pair of nested constant and variable region primers, which increases product specificity. Finally, a third PCR is used to attach an Illumina sequencing adaptor, constructing the library for Illumina MiSeq.

Thus, the methods provided by the present disclosure can be used to explore the antigen-specific T cell repertoire of human subjects. The TCR affinity for cognate MHC has long been implicated as a strong predictor of T cell in vitro and in vivo function. In addition, the present methods can be used to discover the role of TCR affinity and sequence in clonal selection and immune responses in disease settings. For translational research, the methods of the present disclosure can be used to monitor the quality of the T cell response in healthy and diseased human patients, as well as human patients undergoing drug or biologics therapy. The methods can also be used to select T cells bearing high affinity TCR for therapeutics such as adoptive T cell transfer (ACT).

I. Definitions

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a T cell therapy comprising T cells bearing high affinity TCR(s).

"Subject" and "patient" refer to either a human or non-human, such as primates, mammals, and vertebrates. In particular embodiments, the subject is a human.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

"T cell" as used herein denotes a lymphocyte that is maintained in the thymus and has either α:β or γ:δ heterodimeric receptor. There are Vα, vβ, Vγ and V8, Jα, Iβ, Jγ and J5, and v̈β and Oδ loci. Naive T cells have not encountered specific antigens and T cells are naive when leaving the thymus. Naive T cells are identified as CD45RO⁻, CD45RA⁺, and CD62L⁺. Memory T cells mediate immunological memory to respond rapidly on re-exposure to the antigen that originally induced their expansion and can be "CD8+" (T cytotoxic cells) or "CD4+" (T helper cells). Memory CD4 T cells are identified as CD4⁺, CD45RO⁺ cells and memory CD8 cells are identified as CD8⁺ CD45RO⁺.

"T cell receptor" (TCR) refers to a molecule found on the surface of T cells (or T lymphocytes) that, in association with CD3, is generally responsible for recognizing antigens bound to major histocompatibility complex (MHC) molecules. The TCR has a disulfide-linked heterodimer of the highly variable a and β chains (also known as TCRα and TCRβ, respectively) in most T cells. In a small subset of T cells, the TCR is made up of a heterodimer of variable γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., 1997). TCR as used in the present disclosure may be from various animal species, including human, mouse, rat, or other mammals. A TCR may be cell-bound or in soluble form.

TCRs of this disclosure can be "immunospecific" or capable of binding to a desired degree, including "specifically or selectively binding" a target while not significantly binding other components present in a test sample, if they bind a target molecule with an affinity or Ka (i.e., an equilibrium association constant of a particular binding interaction with units of 1/M) of, for example, greater than or equal to about $10^3$ M$^{-1}$. "High affinity" TCR refers to those TCRs with a Ka of, for example, $10^4$ M$^{-1}$ or greater. The affinities obtained by iTAST are 2-dimensional (2D) affinities, but are highly correlated with the conventional 3-dimensional (3D) affinities referenced above (FIG. 2F). Thus, 2D is a reliable surrogate for 3D affinity. In some aspects, the iTAST method can be used to choose a TCR of desired affinity, such as high, medium or low, for adoptive T cell therapy.

"Major histocompatibility complex molecules" (MHC molecules) refer to glycoproteins that deliver peptide antigens to a cell surface. MHC class I molecules are heterodimers consisting of a membrane spanning a chain and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where the peptide:MHC complex is recognized by CD8⁺ T cells. MHC class II molecules deliver peptides originating in the vesicular system to the cell surface, where they are recognized by CD4⁺ T cells. An MHC molecule may be from various animal species, including human, mouse, rat, or other mammals.

"Peptide antigen" refers to an amino acid sequence, ranging from about 7 amino acids to about 25 amino acids in length that is specifically recognized by a TCR, or binding domains thereof, as an antigen, and which may be derived from or based on a fragment of a longer target biological molecule (e.g., polypeptide, protein) or derivative thereof. An antigen may be expressed on a cell surface, within a cell, or as an integral membrane protein. An antigen may be a host-derived (e.g., tumor antigen, autoimmune antigen) or have an exogenous origin (e.g., bacterial, viral).

"MHC-peptide tetramer staining" refers to an assay used to detect antigen-specific T cells, which features a tetramer of MHC molecules, each comprising an identical peptide having an amino acid sequence that is cognate (e.g., identical or related to) at least one antigen, wherein the complex is capable of binding T cells specific for the cognate antigen. Each of the MHC molecules may be tagged with a biotin molecule. Biotinylated MHC/peptides are tetramerized by the addition of streptavidin, which is typically fluorescently labeled. The tetramer may be detected by flow cytometry via the fluorescent label.

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is generally single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al, editors, PCR: A Practical Approach and PCR2: A Practical Approach (IRL Press, Oxford, 1991 and 1995, respectively).

"Nested PCR" refers to a two-stage PCR wherein the amplicon of a first PCR becomes the sample for a second PCR using a new set of primers, at least one of which binds to an interior location of the first amplicon. As used herein, "initial primers" or "first set of primers" in reference to a nested amplification reaction mean the primers used to generate a first amplicon, and "secondary primers" or "second set of primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, *Anal. Biochem.*, 273: 221-228 (1999) (two-color real-time PCR). Usually, distinct sets of primers are employed for each sequence being amplified.

The term "barcode" refers to a nucleic acid sequence that is used to identify a single cell or a subpopulation of cells. Barcode sequences can be linked to a target nucleic acid of interest during amplification and used to trace back the amplicon to the cell from which the target nucleic acid originated. A barcode sequence can be added to a target nucleic acid of interest during amplification by carrying out PCR with a primer that contains a region comprising the barcode sequence and a region that is complementary to the target nucleic acid such that the barcode sequence is incorporated into the final amplified target nucleic acid product (i.e., amplicon). Barcodes can be included in either the forward primer or the reverse primer or both primers used in PCR to amplify a target nucleic acid.

II. Antigen-Specific T Cell Isolation

Embodiments of the present disclosure concern obtaining a population of antigen-specific T cells which are used to determine TCR affinity and sequence. Particularly, the present disclosure relates to a substantially pure antigen-specific T cell population having a functional status which is substantially unaltered by a purification procedure comprising staining the desired T cell population, isolating the stained T cell population from a sample comprising non-stained T cell population and removing said stain, i.e. the functional status of the T cell population before purification is substantially the same as after the purification. In particular aspects, a T cell population is provided which is substantially free from any binding reagents used for the isolation of the population, e.g. antibodies or TCR binding ligands such as multimeric TCR binding ligands. The T cells may be from an in vitro culture, or a physiologic sample. For the most part, the physiologic samples employed will be blood or lymph, but samples may also involve other sources of T cells, particularly where T cells may be invasive. Thus other sites of interest are tissues, or associated fluids, as in the brain, lymph node, neoplasms, spleen, liver, kidney, pancreas, tonsil, thymus, joints, and synovia. Prior treatments may involve removal of cells by various techniques, including centrifugation, using Ficoll-Hypaque, panning, affinity separation, using antibodies specific for one or more markers present as surface membrane proteins on the surface of cells, or any other technique that provides enrichment of the set or subset of cells of interest.

A. Starting Population of T Cells

A starting population of T cells can be obtained from a patient sample or from a healthy blood donor. In some aspects, the sample is a blood sample such as peripheral blood sample. The blood sample can be about 1 mL to about 10 mL, such as about 2 mL to 8 mL, such as about 5 mL. The sample can include at least 500 antigen-specific T cells, at least 250 antigen-specific T cells, at least 100 antigen-specific T cells or at least 50 antigen-specific T cells.

In some embodiments, the T cells are derived from the blood, bone marrow, lymph, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., $CD4^+$ and/or $CD8^+$ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells). In one embodiment, the cells (e.g., $CD8^+$ cells or $CD3^+$ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Ra (CD127). In some examples, $CD8^+$ T cells are enriched for cells positive for CD45RO (or negative for CD45RA) and for CD62L.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about $2\times10^6$ lymphocytes), e.g., from about 10 to about 30 days, such as about 15 to about 28 days.

The cultured T cells can be pooled and rapidly expanded. Rapid expansion provides an increase in the number of antigen-specific T-cells of at least about 50-fold (e.g., 50-, 60-, 70-, 80-, 90-, 100-, 150-fold or greater) over a period of about 10 to about 28 days. In particular, rapid expansion provides an increase of at least about 200-fold (e.g., 200-, 300-, 400-, 500-, 600-, 700-, 800-, 900-, 1000-fold or greater) over a period of about 10 to about 28 days. In some aspects, the TCR affinity is measured and/or sequence is obtained from T cells, such as tumor infiltrating lymphocytes with or without in vitro expansion.

B. Antigens

Any suitable antigen may find use in the present method. Exemplary antigens include, but are not limited to, antigenic molecules from infectious agents, auto-/self-antigens, tumor-/cancer-associated antigens, and tumor neoantigens (Linnemann et al., 2015).

Tumor-associated antigens may be derived from prostate, breast, colorectal, lung, pancreatic, renal, mesothelioma, ovarian, or melanoma cancers. Exemplary tumor-associated antigens or tumor cell-derived antigens include MAGE 1, 3, and MAGE 4 (or other MAGE antigens such as those disclosed in International Patent Publication No. WO99/40188); PRAME; BAGE; RAGE, Lage (also known as NY ESO 1); SAGE; and HAGE or GAGE. These non-limiting examples of tumor antigens are expressed in a wide range of tumor types such as melanoma, lung carcinoma, sarcoma, and bladder carcinoma. See, e.g., U.S. Pat. No. 6,544,518. Prostate cancer tumor-associated antigens include, for example, prostate specific membrane antigen (PSMA), prostate-specific antigen (PSA), prostatic acid phosphates, NKX3.1, and six-transmembrane epithelial antigen of the prostate (STEAP) (Hubert et al., 1999); see also, e.g., Reiter et al., 1998; Nelson, et al., 1999); WO 98/12302; U.S. Pat. Nos. 5,955,306; 5,840,871 and 5,786,148; International Patent Publication Nos. WO 98/20117; WO 00/04149; WO 98/137418).

Other tumor associated antigens include Plu-1, HASH-1, HasH-2, Cripto and Criptin. Additionally, a tumor antigen may be a self peptide hormone, such as whole length gonadotrophin hormone releasing hormone (GnRH, International Patent Publication No. WO 95/20600), a short 10 amino acid long peptide, useful in the treatment of many cancers.

Tumor antigens include tumor antigens derived from cancers that are characterized by tumor-associated antigen expression, such as HER-2/neu expression. Tumor-associated antigens of interest include lineage-specific tumor antigens such as the melanocyte-melanoma lineage antigens MART-1/Melan-A, gp100, gp75, mda-7, tyrosinase and tyrosinase-related protein. Illustrative tumor-associated antigens include, but are not limited to, tumor antigens derived from or comprising any one or more of, p53, Ras, c-Myc, cytoplasmic serine/threonine kinases (e.g., A-Raf, B-Raf, and C-Raf, cyclin-dependent kinases), MAGE-AL MAGE-A2, MAGE-A3, MAGE-A4, MAGE-A6, MAGE-A10, MAGE-A12, MART-1, BAGE, DAM-6, -10, GAGE-1, -2, -8, GAGE-3, -4, -5, -6, -7B, NA88-A, MART-1, MC1R, Gp100, PSA, PSM, Tyrosinase, TRP-1, TRP-2, ART-4, CAMEL, CEA, Cyp-B, hTERT, hTRT, iCE, MUC1, MUC2, Phosphoinositide 3-kinases (PI3Ks), TRK receptors, PRAME, P15, RUL RU2, SART-1, SART-3, Wilms' tumor antigen (WT1), AFP, -catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, receptor tyrosine kinases (e.g., Epidermal Growth Factor receptor (EGFR) (in particular, EGFRvIII), platelet derived growth factor receptor (PDGFR), vascular endothelial growth factor receptor (VEGFR)), cytoplasmic tyrosine kinases (e.g., src-family, syk-ZAP70 family), integrin-linked kinase (ILK), signal transducers and activators of transcription STAT3, STAT5, and STATE, hypoxia inducible factors (e.g., HIF-1 and HIF-2), Nuclear Factor-Kappa B (NF-B), Notch receptors (e.g., Notch1-4), c-Met, mammalian targets of rapamycin (mTOR), WNT, extracellular signal-regulated kinases (ERKs), and their regulatory subunits, PMSA, PR-3, MDM2, Mesothelin, renal cell carcinoma-5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGsS, SART3, STn, PAXS, OY-TES1, sperm protein 17, LCK, HMWMAA, AKAP-4, SSX2, XAGE 1, B7H3, legumain, TIE2, Page4, MAD-CT-1, FAP, MAD-CT-2, fos related antigen 1, CBX2, CLDN6, SPANX, TPTE, ACTL8, ANKRD30A, CDKN2A, MAD2L1, CTAG1B, SUNC1, LRRN1 and idiotype.

Antigens may include epitopic regions or epitopic peptides derived from genes mutated in tumor cells or from genes transcribed at different levels in tumor cells compared to normal cells, such as telomerase enzyme, survivin, mesothelin, mutated ras, bcr/abl rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; tumor antigens that include epitopic regions or epitopic peptides derived from oncoviral processes, such as human papilloma virus proteins E6 and E7; Epstein bar virus protein LMP2; nonmutated oncofetal proteins with a tumor-selective expression, such as carcinoembryonic antigen and alpha-fetoprotein. See also Boon et al., 1994; Renkvist et al., 2001.

In other embodiments, an antigen is obtained or derived from a pathogenic microorganism or from an opportunistic pathogenic microorganism (also called herein an infectious disease microorganism), such as a virus, fungus, parasite, and bacterium. In certain embodiments, antigens derived from such a microorganism include full-length proteins.

Illustrative pathogenic organisms whose antigens are contemplated for use in the method described herein include human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV), *Staphylococcus* species including Methicillin-resistant *Staphylococcus aureus* (MRSA), and *Streptococcus* species including *Streptococcus pneumoniae*. As would be understood by the skilled person, proteins derived from these and other pathogenic microorganisms for use as antigen as described herein and nucleotide sequences encoding the proteins may be identified in publications and in public databases such as GENBANK®, Swiss-Prot®, and TrEMBL®.

Antigens derived from human immunodeficiency virus (HIV) include any of the HIV virion structural proteins (e.g., gp120, gp41, p17, p24), protease, reverse transcriptase, or HIV proteins encoded by tat, rev, nef, vif, vpr and vpu.

Antigens derived from herpes simplex virus (e.g., HSV 1 and HSV2) include, but are not limited to, proteins expressed from HSV late genes. The late group of genes predominantly encodes proteins that form the virion particle. Such proteins include the five proteins from (UL) which form the viral capsid: UL6, UL18, UL35, UL38 and the major capsid protein UL19, UL45, and UL27, each of which may be used as an antigen as described herein (see, e.g., McGeoch et al., 2006). Other illustrative HSV proteins contemplated for use as antigens herein include the ICP27 (H1, H2), glycoprotein B (gB) and glycoprotein D (gD) proteins. The HSV genome comprises at least 74 genes, each encoding a protein that could potentially be used as an antigen.

Antigens derived from cytomegalovirus (CMV) include CMV structural proteins, viral antigens expressed during the immediate early and early phases of virus replication, glycoproteins I and III, capsid protein, coat protein, lower matrix protein pp65 (ppUL83), p52 (ppUL44), IE1 and 1E2 (UL123 and UL122), protein products from the cluster of genes from UL128-UL150 (Rykman, et al., 2006), envelope glycoprotein B (gB), gH, gN, and pp150. As would be understood by the skilled person, CMV proteins for use as antigens described herein may be identified in public databases such as GenBank®, Swiss-Prot®, and TrEMBL® (see e.g., Bennekov et al., 2004; Loewendorf et al., 2010; Marschall et al., 2009).

Antigens derived from Epstein-Ban virus (EBV) that are contemplated for use in certain embodiments include EBV lytic proteins gp350 and gp110, EBV proteins produced during latent cycle infection including Epstein-Ban nuclear antigen (EBNA)-1, EBNA-2, EBNA-3A, EBNA-3B, EBNA-3C, EBNA-leader protein (EBNA-LP) and latent membrane proteins (LMP)-1, LMP-2A and LMP-2B (see, e.g., Lockey et al., 2008).

Antigens derived from respiratory syncytial virus (RSV) that are contemplated for use herein include any of the eleven proteins encoded by the RSV genome, or antigenic fragments thereof: NS 1, NS2, N (nucleocapsid protein), M (Matrix protein) SH, G and F (viral coat proteins), M2 (second matrix protein), M2-1 (elongation factor), M2-2 (transcription regulation), RNA polymerase, and phosphoprotein P.

Antigens derived from Vesicular stomatitis virus (VSV) that are contemplated for use include any one of the five major proteins encoded by the VSV genome, and antigenic fragments thereof: large protein (L), glycoprotein (G), nucleoprotein (N), phosphoprotein (P), and matrix protein (M) (see, e.g., Rieder et al., 1999).

Antigens derived from an influenza virus that are contemplated for use in certain embodiments include hemagglutinin (HA), neuraminidase (NA), nucleoprotein (NP), matrix proteins M1 and M2, NS1, NS2 (NEP), PA, PB1, PB1-F2, and PB2.

Exemplary viral antigens also include, but are not limited to, adenovirus polypeptides, alphavirus polypeptides, calicivirus polypeptides (e.g., a calicivirus capsid antigen), coronavirus polypeptides, distemper virus polypeptides, Ebola virus polypeptides, enterovirus polypeptides, flavivirus polypeptides, hepatitis virus (AE) polypeptides (a hepatitis B core or surface antigen, a hepatitis C virus E1 or E2 glycoproteins, core, or non-structural proteins), herpesvirus polypeptides (including a herpes simplex virus or varicella zoster virus glycoprotein), infectious peritonitis virus polypeptides, leukemia virus polypeptides, Marburg virus polypeptides, orthomyxovirus polypeptides, papilloma virus polypeptides, parainfluenza virus polypeptides (e.g., the hemagglutinin and neuraminidase polypeptides), paramyxovirus polypeptides, parvovirus polypeptides, pestivirus polypeptides, picorna virus polypeptides (e.g., a poliovirus capsid polypeptide), pox virus polypeptides (e.g., a vaccinia virus polypeptide), rabies virus polypeptides (e.g., a rabies virus glycoprotein G), reovirus polypeptides, retrovirus polypeptides, and rotavirus polypeptides.

In certain embodiments, the antigen may be bacterial antigens. In certain embodiments, a bacterial antigen of interest may be a secreted polypeptide. In other certain embodiments, bacterial antigens include antigens that have a portion or portions of the polypeptide exposed on the outer cell surface of the bacteria.

Antigens derived from *Staphylococcus* species including Methicillin-resistant *Staphylococcus aureus* (MRSA) that are contemplated for use include virulence regulators, such as the Agr system, Sar and Sae, the Arl system, Sar homologues (Rot, MgrA, SarS, SarR, SarT, SarU, SarV, SarX, SarZ and TcaR), the Srr system and TRAP. Other *Staphylococcus* proteins that may serve as antigens include Clp proteins, HtrA, MsrR, aconitase, CcpA, SvrA, Msa, CfvA and CfvB (see, e.g., *Staphylococcus*: Molecular Genetics, 2008 Caister Academic Press, Ed. Jodi Lindsay). The genomes for two species of *Staphylococcus aureus* (N315 and Mu50) have been sequenced and are publicly available, for example at PATRIC (PATRIC: The VBI PathoSystems Resource Integration Center, Snyder et al., 2007). As would be understood by the skilled person, *Staphylococcus* proteins for use as antigens may also be identified in other public databases such as GenBank®, Swiss-Prot®, and TrEMBL®.

Antigens derived from *Streptococcus pneumoniae* that are contemplated for use in certain embodiments described herein include pneumolysin, PspA, choline-binding protein A (CbpA), NanA, NanB, SpnHL, PavA, LytA, Pht, and pilin proteins (RrgA; RrgB; RrgC). Antigenic proteins of *Streptococcus pneumoniae* are also known in the art and may be used as an antigen in some embodiments (see, e.g., Zysk et al., 2000). The complete genome sequence of a virulent strain of *Streptococcus pneumoniae* has been sequenced and, as would be understood by the skilled person, *S. pneumoniae* proteins for use herein may also be identified in other public databases such as GenBank®, Swiss-Prot®, and TrEMBL®. Proteins of particular interest for antigens according to the present disclosure include virulence factors and proteins predicted to be exposed at the surface of the pneumococci (see, e.g., Frolet et al., 2010).

Examples of bacterial antigens that may be used as antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides (e.g., *B. burgdorferi* OspA), *Brucella* polypeptides, *Campylobacter* polypeptides, Capnocytophaga polypeptides, *Chlamydia* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides (e.g., *H. influenzae* type b outer membrane protein), *Helicobacter* polypeptides, *Klebsiella* polypeptides, L-form bacteria polypeptides, *Leptospira* polypeptides, *Listeria* polypeptides, Mycobacteria polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Pepto-* streptococcus polypeptides, Pneumococcus polypeptides (i.e., *S. pneumoniae* polypeptides) (see description herein), *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, group A *streptococcus* polypeptides (e.g., *S. pyogenes* M proteins), group B *streptococcus* (*S. agalactiae*) polypeptides, *Treponema* polypeptides, and *Yersinia* polypeptides (e.g., *Y. pestis* F1 and V antigens).

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides. Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides. (e.g., *P. falciparum* circumsporozoite (PfCSP)), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of ectoparasite antigens include, but are not limited to, polypeptides (including antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

In some embodiments, the antigen is an autoantigen. In one embodiment, the autoantigen is a type 1 diabetes autoantigen, including, but not limited to, PDX1, AnT8, CHGA IAAP, GAD(65) and/or DiaPep277. In one embodiment, the autoantigen is an alopecia areata autoantigen, including, but not limited to, keratin 16, K18585, M10510, J01523, 022528, D04547, 005529, B20572 and/or F11552. In one embodiment, the autoantigen is a systemic lupus erythematosus autoantigen, including, but not limited to, TRIM21/Ro52/SS-A 1 and/or histone H2B. In one embodiment, the autoantigen is a Behcet's disease autoantigen, including, but not limited to, S-antigen, alpha-enolase, selenium binding partner and/or Sip1 C-ter. In one embodiment, the autoantigen is a Sjögren's syndrome autoantigen, including, but not limited to, La/SSB, KLK11 and/or a 45-kd nucleus protein. In one embodiment, the autoantigen is a rheumatoid arthritis autoantigen, including, but not limited to, vimentin, gelsolin, alpha 2 HS glycoprotein (AHSG), glial fibrillary acidic protein (GFAP), α1B-glycoprotein (A1BG), RA33 and/or citrullinated 31F4G1. In one embodiment, the autoantigen is a Grave's disease autoantigen. In one embodiment, the autoantigen is an antiphospholipid antibody syndrome autoantigen, including, but not limited to, zwitterionic phospholipids, phosphatidyl-ethanolamine, phospholipid-binding plasma protein, phospholipid-protein complexes, anionic phospholipids, cardiolipin, f2-glycoprotein I (β2GPI), phosphatidylserine, lyso(bis)phosphatidic acid, phosphatidylethanolamine, vimentin and/or annexin A5. In one embodiment, the autoantigen is a multiple sclerosis autoantigen, including, but not limited to, myelin-associated oligodendrocytic basic protein (MOBP), myelin basic protein (MBP), myelin proteolipid protein (PLP), myelin oligodendrocyte glycoprotein (MOG) and/or alpha-B-crytallin. In one embodiment, the autoantigen is an irritable bowel disease autoantigen, including, but not limited to, a ribonucleoprotein complex, a small nuclear ribonuclear polypeptide A and/or Ro-5,200 kDa. In one embodiment, the autoantigen is a Crohn's disease autoantigen, including, but not limited to, zymogen granule membrane glycoprotein 2 (GP2), an 84 by allele of CTLA-4 AT repeat polymorphism, MRP8, MRP14 and/or complex MRP8/14. In one embodiment, the autoantigen is a dermatomyositis autoantigen, including, but not limited to, aminoacyl-tRNA synthetases, Mi-2 helicase/deacetylase protein complex, signal recognition particle (SRP), T2F1-γ, MDAS, NXP2, SAE and/or HMGCR. In one embodiment, the autoantigen is an ulcerative colitis autoantigen, including, but not limited to, 7E12H12 and/or M(r) 40 kD autoantigen.

In some embodiments, the autoantigen is a collagen, e.g., collagen type II; other collagens such as collagen type IX, collagen type V, collagen type XXVII, collagen type XVIII, collagen type IV, collagen type IX; aggrecan I; pancreas-specific protein disulphide isomerise A2; interphotoreceptor retinoid binding protein (IRBP); a human IRBP peptide 1-20; protein lipoprotein; insulin 2; glutamic acid decarboxylase (GAD) 1 (GAD67 protein), BAFF, IGF2. Further examples of autoantigens include ICA69 and CYP1A2, Tph and Fabp2, Tgn, Spt1 & 2 and Mater, and the CB11 peptide from collagen.

C. Isolation by Streptamers

In some aspects, the T cells are reversibly stained by contacting the population of T cells with tetravalent conjugates (e.g., MHC I STREPTAMERS®) which comprise four identical subunits of a single ligand (e.g., peptide-major histocompatibility complexes (pMHC)) which specifically binds to the TCR and has a detectable label. For example, the ligand may be pMHC in which the peptide may be conjugated to an α and/or a 13 chain of the MHC molecule. The binding complex may have a wide variety of peptide-MHC combinations. Multimers of class I MHC molecules will usually be used to detect CD8+ T cells, and class II multimers will usually be used to detect CD4+ T cells. The peptide usually has a length of about 8 to about 25 amino acids and may comprise anchor amino acid residues capable of allele-specific binding to a predetermined MHC molecule class, e.g. an MHC class I, an MHC class II or a non-classical MHC class. In particular aspects, the MHC molecule is an MHC class I molecule. Included in the HLA proteins are the class II subunits HLA-DPα, HLA-DPβ, HLA-DQα, HLA-DQβ, HLA-DRα and HLA-DRβ, and the class I proteins HLA-A, HLA-B, HLA-C, and $\beta_2$-microglobulin.

The peptides may have a sequence derived from a wide variety of proteins. The T cell epitopic sequences from a number of antigens are known in the art. Alternatively, the epitopic sequence may be empirically determined, by isolating and sequencing peptides bound to native MHC proteins, by synthesis of a series of peptides from the target sequence, then assaying for T cell reactivity to the different peptides, or by producing a series of binding complexes with different peptides and quantitating the T cell binding. Preparation of fragments, identifying sequences, and identifying the minimal sequence is described in U.S. Pat. No. 5,019,384; incorporated herein by reference. The peptides may be prepared in a variety of ways. Conveniently, they can be synthesized by conventional techniques employing automatic synthesizers, or may be synthesized manually. Alternatively, DNA sequences can be prepared which encode the particular peptide and may be cloned and expressed to provide the desired peptide. In this instance a methionine may be the first amino acid. In addition, peptides may be produced by recombinant methods as a fusion to proteins that are one of a specific binding pair, allowing purification of the fusion protein by means of affinity reagents, followed by proteolytic cleavage, usually at an engineered site to yield the desired peptide (see for example Driscoll et al., 1993). The peptides may also be isolated from natural sources and purified by known techniques, including, for example, chromatography on ion exchange materials, separation by size, immunoaffinity chromatography and electrophoresis.

The labeled binding partner may be free in solution, or may be attached to an insoluble support. Examples of suitable insoluble supports include beads, e.g. magnetic beads, membranes and microtiter plates. These are typically made of glass, plastic (e.g. polystyrene), polysaccharides, nylon or nitrocellulose. In general the label will have a light detectable characteristic. Preferred labels are fluorophores, such as fluorescein isothiocyanate (FITC), rhodamine, Texas Red, phycoerythrin and allophycocyanin. Other labels of interest may include dyes, enzymes, chemiluminescers, particles, radioisotopes, or other directly or indirectly detectable agent.

A number of methods for detection and quantitation of labeled cells are known in the art. Flow cytometry is a convenient means of enumerating cells that are a small percent of the total population. Fluorescent microscopy may also be used. Various immunoassays, e.g. ELISA, RIA, etc. may be used to quantitate the number of cells present after binding to an insoluble support. In particular aspects, flow cyometry is used for the separation of a labeled subset of T cells from a complex mixture of cells.

Alternative means of separation utilize the binding complex bound directly or indirectly to an insoluble support, e.g. column, microtiter plate, magnetic beads, etc. The cell sample is added to the binding complex. The complex may be bound to the support by any convenient means. After incubation, the insoluble support is washed to remove non-bound components. From one to six washes may be employed, with sufficient volume to thoroughly wash non-specifically bound cells present in the sample. The desired cells are then eluted from the binding complex. In particular the use of magnetic particles to separate cell subsets from complex mixtures is described in Miltenyi et al., 1990.

In some embodiments, the T cells which bind the specific pMHC can then be isolated by sorting for the detectable label. The separation of T cell, from other sample components, e.g. unstained T cells may be effected by conventional methods, e.g. cell sorting, preferably by FACS methods using commercially available systems (e.g. FACSVantage by Becton Dickinson or Moflo by Cytomation), or by magnetic cell separation (e.g. MACS by Miltenyi). The staining may be removed from the T cell by disruption of the reversible bond which results in a complete removal of any reagent bound to the target cell, because the bond between the receptor-binding component and the receptor on the target cell is a low-affinity interaction. For example, the addition of biotin could be used to disrupt the Strep-tag and the Strep-Tactin complex of a STREPTAMER®. In some aspects, the Strep-tag and the Strep-Tactin are dissociated by a dissociation buffer comprising biotin at a final concentration of about 1 mM to about 15 mM. In particular aspects, the dissociation buffer may comprise sodium azide to prevent premature T cell activation (e.g., about 0.1% to about 0.5%). The streptamer-bound T cells may be incubated in the dissociation buffer for about at least 15, 20, 25, 30, 40, 45, 50, 55, 60, 65, 70, 75, 80, 85 or 90 minutes.

The medium in which the cells are labeled will be any suitable medium as known in the art. If live cells are desired a medium will be chosen that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc. In some aspects, the staining and the subsequent removal of the staining is carried out at a temperature of ≤15° C., such as ≤10° C., such as at about 4° C.

Peptide sequences (Strep-tags) such as disclosed in U.S. Pat. No. 5,506,121 demonstrate binding affinity for the biotin binding site of streptavidin, e.g. with a $K_d$ of approx. between $10^{-4}$ and $10^{-5}$ M. The binding affinity may be further improved by making a mutations within the streptavidin molecule. Examples of optimized streptavidin mutants (STREP-TACTIN® peptides, IBA GmbH) are described in U.S. Pat. No. 6,103,493, which is herein incorporated by reference.

Alternatively, an antigen-specific population of T cells can be obtained by clonal expansion of an antigen-specific T cell. For example, a T cell can be engineered to express a given TCR (e.g., described for example in U.S. Patent Publication No. 20150307585; incorporated herein by reference) and then expanded in vitro. For example, the T cells may be transduced to express a T cell receptor (TCR) having antigenic specificity for a cancer antigen using transduction techniques described in Heemskerk et al., 2009.

III. Two-Dimensional TCR-pMHC Affinity

Certain embodiments of the present disclosure concern the use of the micropipette adhesion assay to determine the 2D TCR-pMHC affinity. One method to perform a micropipette adhesion is described in Huang et al., 2010; incorporated herein by reference. Briefly, this methods measures 2D TCR-pMHC affinity by using a micropipette and biomembrane force probe with a red blood cell (RBC) as the adhesion sensor. The RBC may be coated with pMHC by biotin-streptavidin coupling. The T cell is micro-manipulated to touch the RBC with a controlled contact area and time. Specifically, the micropipette and BFP apparatuses are centered around an inverted microscope placed on an anti-vibration table equipped with manometer systems to apply suction pressures through glass pipettes. Two opposing pipettes are used in both apparatuses to control contacts of a T cell (target) with a pMHC-presenting surface (e.g., a RBC (micropipette) or a bead (BFP)). The TCR-pMHC binding, if present, is observed by RBC elongation. To determine the likelihood of adhesion, the cell pair is repeatedly moved in and out of contact for a given contact time to yield and adhesion frequency. In particular aspects, the adhesion frequency is between 30% and 80%. If the adhesion frequency is lower than 30% after 10 contacts, then a new RBC with a higher site density is used and adhesion frequency is measured again until at least 30% is reached for 10 contacts.

Accordingly, some embodiments provide the 2D TCR-pMHC affinity to determine the T cell function or responsiveness. The function may be measured by the magnitude of cell killing as well as sensitivity to a given antigen.

An adhesion curve can be determined by obtaining the adhesion probability at multiple contact times using Equation 1 (Eq. 1) for reversible bimolecular interactions at two-dimensional surfaces:

$$P_a = 1 - \exp\{-m_r m_l A_c K_a [-k_{off} t]\} \quad \text{(Eq. 1)}$$

Where $P_a$ is the adhesion frequency, $m_r$ is the TCR site density, $m_l$ is the pMHC site density, $A_c$ is the contact area between RBC and T cell, $K_a$ is the 2D affinity, $k_{off}$ is the 2D dissociation rate constant, and t is contact time. $A_c$ is kept constant for all measurements, and it is estimated it to be within several percent of 3 $\mu m^2$ based on the length-calibrated images from the microscope. However, since the actual contact area cannot be known, $A_c K_a$ is used as the effective 2D affinity in all 2D affinity publications (Huang et al., 2010), with a unit of $\mu m^4$.

In Eq. 1 as t goes to infinity, $P_a$ reaches an equilibrium value:

$$A_c K_a = -\ln(1 - P_{a,eq})/m_r m_l \quad \text{(Eq. 2)}$$

The site density of the TCR and the pMHC can be measured by flow cytometry. In one method, the T cells are incubated with The fluorescent intensities are compared to standard calibration beads (BD Quantibrite PE Beads, BD or FITC calibration beads, Bangs laboratories) to determine the total number of molecules per cell/bead, which are divided by the cell/bead surface area to obtain site densities. The apparent surface areas of the naive (158 $\mu m^2$) and activated (260 $\mu m^2$) T cells are calculated as the areas of smooth spheres from their radii measured microscopically. In particular aspects, the assay is performed at a temperature of either 4° C., room temperature (e.g., 25° C.), or physiological temperatures (e.g., 37° C.).

Alternatively, the adhesion frequency Pa can be calculated by using the average bond number <n>:

$$P_a = 1 - \exp(-<n>)$$

$$<n> = m_r m_l A_c K_a$$

The number of pMHCs required for an average bond number of 1 to form was then derived, using 3 $\mu m^2$ to approximate the contact area:

$$\text{\# of } pMHC \text{ to form 1 bond} = \frac{A_c m_{pMHC}}{<n>} = -\frac{A_c m_{pMHC}}{\ln(1 - P_a)} \quad \text{(Eq. 3)}$$

IV. TCR Sequencing

Methods are also provided herein for the sequencing of the TCR. The sequencing may be performed on a T cell after the 2D affinity has been determined by transferring the T cell to lysis buffer using a micropipette. In some embodiments, methods are provided for the simultaneous sequencing of TCRα and TCRβ genes and amplification of transcripts of functional interest in the single T cells which enable linkage of TCR specificity with information about T cell function. The methods generally involve sorting of single T cells into separate locations (e.g., separate wells of a multi-well titer plate) followed by nested polymerase chain reaction (PCR) amplification of nucleic acids encoding TCRs and T cell phenotypic markers. The amplicons are barcoded to identify their cell of origin, combined, and analyzed by deep sequencing.

In one method, a nested PCR approach is used in combination with deep sequencing such as described in Han et al., 2014; incorporated herein by reference. Briefly, single T cells are sorted into separate wells (e.g., 96-well PCR plate) and reverse transcription is performed using TCR primers and phenotyping primers. In order to amplify unknown TCR sequences, ligation anchor PCR may be used. One amplification primer is specific for a TCR constant region. The other primer is ligated to the terminus of cDNA synthesized from TCR encoding mRNA. The variable region is amplified by PCR between the constant region sequence and the ligated primer. Next, nested PCR is performed with TCRα/TCRβ primers (e.g., sequences in Tables 1 and 2) and a third reaction is performed to incorporate individual barcodes. The products are combined, purified and sequenced using the Illumina MiSeq platform. The resulting paired-end sequencing reads are assembled and deconvoluted using barcode identifiers at both ends of each sequence by a custom software pipeline to separate reads from every well in every plate. For TCR sequences, the CDR3 nucleotide sequences are then extracted and translated.

TABLE 1

| TCRα Primer Sequences | | | |
|---|---|---|---|
| TCRα alleles | 1st PCR outer 5' - 3' | TCRα alleles | 2nd PCR inner 5' - 3' |
| TRAV1-1/2 | GCACCCACATTTCTKT CTTACAATG (SEQ ID NO: 6) | TRAV1-1/2 | GACGTGTGCTCTTCCGATCTGAMAG GTCGTTTTTCTTCATTCCTT (SEQ ID NO: 7) |
| TRAV2 | ATGTGCACCAAGACTC CTTGTTAAA (SEQ ID NO: 8) | TRAV2 | GACGTGTGCTCTTCCGATCTAGGGA CGATACAACATGACCTATGA (SEQ ID NO: 9) |
| TRAV3 | GCAGCTATGGCTTTGA AGCTG (SEQ ID NO: 10) | TRAV3/8-2/4/5/6/7 | GACGTGTGCTCTTCCGATCTTCCTTC CACCTGAVGAAACC (SEQ ID NO: 11) |
| TRAV8 | AAVGGYTTTGAGGCTG AATTT (SEQ ID NO: 12) | TRAV8-1/2/3 | GACGTGTGCTCTTCCGATCTTTYAAT CTGAGGAAACCCTCTGTG (SEQ ID NO: 13) |
| TRAV4 | CAAGACAAAAGTTACA AACGAAGTGG (SEQ ID NO: 14) | TRAV4 | GACGTGTGCTCTTCCGATCTGACAG AAAGTCCAGCACTCTGAGC (SEQ ID NO: 15) |
| TRAV5 | TGGACATGAAACAAGA CCAAAGACT (SEQ ID NO: 16) | TRAV5 | GACGTGTGCTCTTCCGATCTGGATAA ACATCTGTCTCTGCGCATT (SEQ ID NO: 17) |
| TRAV6 | AAAAAGGAAAGAAAG ACTGAAGGT (SEQ ID NO: 18) | TRAV6 | GACGTGTGCTCTTCCGATCTCACCTT TGATACCACCCTTAAMCAG (SEQ ID NO: 19) |
| TRAV7 | TCAGCTGGATATGAGA AGCAGAAAG (SEQ ID NO: 20) | TRAV7 | GACGTGTGCTCTTCCGATCTTTACTG AAGAATGGAAGCAGCTTGT (SEQ ID NO: 21) |
| TRAV9 | AAGGGAAGSAACAAA GGTTTTGAAG (SEQ ID NO: 22) | TRAV9 | GACGTGTGCTCTTCCGATCTCGTAAR GAAACCACTTCTTTCCACT (SEQ ID NO: 23) |
| TRAV10 | AGAACACAAAGTCGAA CGGAAGATA (SEQ ID NO: 24) | TRAV10 | GACGTGTGCTCTTCCGATCTAAGCA AAGCTCTCTGCACATCAC (SEQ ID NO: 25) |
| TRAV11/15 | TTGTGTCTTTGACCTTA ATTCAATC (SEQ ID NO: 26) | TRAV11/15 | GACGTGTGCTCTTCCGATCTGCTTGG AAAAGARAARTTTTATAGTG (SEQ ID NO: 27) |
| TRAV12 | TCARTGTTCCAGAGGG AGCCAYT (SEQ ID NO: 28) | TRAV12 | GACGTGTGCTCTTCCGATCTGAAGAT GGAAGGTTTACAGCACA (SEQ ID NO: 29) |
| TRAV13 | CTGAGTGTCCAGGAGG GWGACA (SEQ ID NO: 30) | TRAV13 | GACGTGTGCTCTTCCGATCTTYATTA TAGACATTCGTTCAAATRTGG (SEQ ID NO: 31) |
| TRAV14 | AGCAGTGGGGAAATGA TTTTTCTT (SEQ ID NO: 32) | TRAV14 | GACGTGTGCTCTTCCGATCTTTGAAT TTCCAGAAGGCAAGAAAAT (SEQ ID NO: 33) |
| TRAV16 | TCTAGAGAGAGCATCA AAGGCTTCA (SEQ ID NO: 34) | TRAV16 | GACGTGTGCTCTTCCGATCTGACCTT AACAAAGGCGAGACATCTT (SEQ ID NO: 35) |
| TRAV17 | CGTTCAAATGAAAGAG AGAAACACA (SEQ ID NO: 36) | TRAV17 | GACGTGTGCTCTTCCGATCTCTTGAC ACTTCCAAGAAAAGCAGTT (SEQ ID NO: 37) |
| TRAV18 | CCTGAAAAGTTCAGAA AACCAGGAG (SEQ ID NO: 38) | TRAV18 | GACGTGTGCTCTTCCGATCTTTTTCA GGCCAGTCCTATCAAGAGT (SEQ ID NO: 39) |
| TRAV19 | CCTTATTCGTCGGAAC TCTTTTGAT (SEQ ID NO: 40) | TRAV19 | GACGTGTGCTCTTCCGATCTGAAAT AAGTGGTCGGTATTCTTGG (SEQ ID NO: 41) |
| TRAV20 | CTGGGGAAGAAAAGG AGAAAGAAAG (SEQ ID NO: 42) | TRAV20 | GACGTGTGCTCTTCCGATCTAGCCAC ATTAACAAAGAAGGAAAGC (SEQ ID NO: 43) |

TABLE 1-continued

TCRα Primer Sequences

| TCRα alleles | 1st PCR outer 5' - 3' | TCRα alleles | 2nd PCR inner 5' - 3' |
|---|---|---|---|
| TRAV21 | CAGAGAGAGCAAACAAGTGGAAGAC (SEQ ID NO: 44) | TRAV21 | GACGTGTGCTCTTCCGATCTTTAATGCCTCGCTGGATAAATCAT (SEQ ID NO: 45) |
| TRAV22 | CATCAACCTGTTTTACATTCCCTCA (SEQ ID NO: 46) | TRAV22 | GACGTGTGCTCTTCCGATCTGCTACGGAACGCTACAGCTTATTG (SEQ ID NO: 47) |
| TRAV23 | GCATTATTGATAGCCATACGTCCAG (SEQ ID NO: 48) | TRAV23 | GACGTGTGCTCTTCCGATCTGAGTGAAAAGAAAGAAGGAAGATTCA (SEQ ID NO: 49) |
| TRAV24 | TAAATGGGGATGAAAAGAAGAAAGG (SEQ ID NO: 50) | TRAV24 | GACGTGTGCTCTTCCGATCTTACCAAGGAGGGTTACAGCTATTTG (SEQ ID NO: 51) |
| TRAV25 | CTGGTGGACATCCCGTTTTT (SEQ ID NO: 52) | TRAV25 | GACGTGTGCTCTTCCGATCTGGAGAAGTGAAGAAGCAGAAAAGA (SEQ ID NO: 53) |
| TRAV26 | ATTGGTATCGACAGMTTCMCTCC (SEQ ID NO: 54) | TRAV26 | GACGTGTGCTCTTCCGATCTAAGACAGAAAGTCCAGYACCTTGAT (SEQ ID NO: 55) |
| TRAV27 | CCTGTCCTCCTGGTGACAGTAGTTA (SEQ ID NO: 56) | TRAV27 | GACGTGTGCTCTTCCGATCTTGGAGAAGTGAAGAAGCTGAAGAGA (SEQ ID NO: 57) |
| TRAV28 | GGACCCCTCATGTCCTTATTTAACA (SEQ ID NO: 58) | TRAV28 | GACGTGTGCTCTTCCGATCTGAAGACTAAAATCCGCAGTCAAAGC (SEQ ID NO: 59) |
| TRAV29 | TGCTGAAGGTCCTACATTCCTGATA (SEQ ID NO: 60) | TRAV29 | GACGTGTGCTCTTCCGATCTTCCATTAAGGATAAAAATGAAGATGGA (SEQ ID NO: 61) |
| TRAV30 | CCCGTCTTCCTGATGATATTACTGA (SEQ ID NO: 62) | TRAV30 | GACGTGTGCTCTTCCGATCTAAGCRGCAAAGCTCCCTGTACCTTA (SEQ ID NO: 63) |
| TRAV31 | GAAGATTATTTTCCTCATTTATCAGC (SEQ ID NO: 64) | TRAV31 | GACGTGTGCTCTTCCGATCTAATGCGACACAGGGTCAATATTCT (SEQ ID NO: 65) |
| TRAV32 | GGGAAGGCCCTAATATCTTAATGGA (SEQ ID NO: 66) | TRAV32 | GACGTGTGCTCTTCCGATCTTGTGGATAGAAAACAGGACAGAAGG (SEQ ID NO: 67) |
| TRAV33 | CCCAGTGAAGAGATGGTTTTCCTTA (SEQ ID NO: 68) | TRAV33 | GACGTGTGCTCTTCCGATCTAAGTCAAATGCAAAGCCTGTGAAC (SEQ ID NO: 69) |
| TRAV34 | TGAAGGTCTTATCTTCTTGATGATGC (SEQ ID NO: 70) | TRAV34 | GACGTGTGCTCTTCCGATCTGGGAAGAGAAAAGTCATGAAAAGA (SEQ ID NO: 71) |
| TRAV35 | AGGTCCTGTCCTCTTGATAGCCTTA (SEQ ID NO: 72) | TRAV35 | GACGTGTGCTCTTCCGATCTGGAAGACTGACTGCTCAGTTTGGTA (SEQ ID NO: 73) |
| TRAV36 | GGAAAAGAAAGCTCCCACATTTCTA (SEQ ID NO: 74) | TRAV36 | GACGTGTGCTCTTCCGATCTTGGAATTGAAAAGAAGTCAGGAAGA (SEQ ID NO: 75) |
| TRAV37 | CCTCATTTCCCTGATACAAATGCTA (SEQ ID NO: 76) | TRAV37 | GACGTGTGCTCTTCCGATCTAGAAGATCAGTGGAAGATTCACAGC (SEQ ID NO: 77) |
| TRAV38 | AGCAGGCAGATGATTCTCGTTATTC (SEQ ID NO: 78) | TRAV38 | GACGTGTGCTCTTCCGATCTAGAAAGCAGCCAAATCCTTCAGTCT (SEQ ID NO: 79) |

TABLE 1-continued

TCRα Primer Sequences

| TCRα alleles | 1st PCR outer 5' - 3' | TCRα alleles | 2nd PCR inner 5' - 3' |
|---|---|---|---|
| TRAV39 | GTCTGGAATCTCTGTTT GTGTTGCT (SEQ ID NO: 80) | TRAV39 | GACGTGTGCTCTTCCGATCTGACGAT TAATGGCCTCACTTGATAC (SEQ ID NO: 81) |
| TRAV40 | TGCAGCTTCTTCAGAG AGAGACAAT (SEQ ID NO: 82) | TRAV40 | GACGTGTGCTCTTCCGATCTGGAGG CGGAAATATTAAAGACAAAA (SEQ ID NO: 83) |
| TRAV41 | GCATTGTTTCCTTGTTT ATGCTGAG (SEQ ID NO: 84) | TRAV41 | GACGTGTGCTCTTCCGATCTGCATGG AAGATTAATTGCCACAATA (SEQ ID NO: 85) |

TABLE 2

TCRβ Primer Sequences

| TCRβ alleles | 1st PCR outer 5' - 3' | TCRβ alleles | 2nd PCR inner 5' - 3' |
|---|---|---|---|
| TRBV1 | AAGAAATCCCTGGAGT TCATGTTTT (SEQ ID NO: 86) | TRBV1 | GACGTGTGCTCTTCCGATCTCTGAC AGCTCTCGCTTATACCTTCA (SEQ ID NO: 87) |
| TRBV2 | GTACAGACAAATCTTG GGGCAGAAA (SEQ ID NO: 88) | TRBV2 | GACGTGTGCTCTTCCGATCTGCCTG ATGGATCAAATTTCACTCTG (SEQ ID NO: 89) |
| TRBV3 | TCTGGGCCATRATRCTA TGTATTGG (SEQ ID NO: 90) | TRBV3 | GACGTGTGCTCTTCCGATCTAATG AAACAGTTCCAAATCGMTTCT (SEQ ID NO: 91) |
| TRBV4 | AGTGTGCCAAGTCGCTT CTCAC (SEQ ID NO: 92) | TRBV4 | GACGTGTGCTCTTCCGATCTCCAA GTCGCTTCTCACCTGAAT (SEQ ID NO: 93) |
| TRBV5-1/2/3/4/5/6/7 | GGGCCCCAGTTTATCTT TCAGTAT (SEQ ID NO: 94) | TRBV5-1 | GACGTGTGCTCTTCCGATCTCGCCA GTTCTCTAACTCTCGCTCT (SEQ ID NO: 95) |
| TRBV5-8 | CAGYTCCTCCTTTGGTA TGACGAG (SEQ ID NO: 96) | TRBV5-2 | GACGTGTGCTCTTCCGATCTTTACT GAGTCAAACACGGAGCTAGG (SEQ ID NO: 97) |
| | | TRBV5-3 | GACGTGTGCTCTTCCGATCTCTCTG AGATGAATGTGAGTGCCTTG (SEQ ID NO: 98) |
| | | TRBV5-4/5/6/7/8 | GACGTGTGCTCTTCCGATCTCTGAG CTGAATGTGAACGCCTTG (SEQ ID NO: 99) |
| TRBV6-1 | GAGGGTACCACTGACA AAGGAGAAG (SEQ ID NO: 100) | TRBV6-1 | GACGTGTGCTCTTCCGATCTTCTCC AGATTAAACAAACGGGAGTT (SEQ ID NO: 101) |
| TRBV6-2/3 | ACTCAGTTGGTGAGGG TACAACTGC (SEQ ID NO: 102) | TRBV6-2/3 | GACGTGTGCTCTTCCGATCTCTGAT GGCTACAATGTCTCCAGATT (SEQ ID NO: 103) |
| TRBV6-4 | AGGTACCACTGGCAAA GGAGAAGT (SEQ ID NO: 104) | TRBV6-4 | GACGTGTGCTCTTCCGATCTAGTGT CTCCAGAGCAAACACAGATG (SEQ ID NO: 105) |
| TRBV6-5/6 | TCAGTTGGTGCTGGTAT CACTGAY (SEQ ID NO: 106) | TRBV6-5/6/7 | GACGTGTGCTCTTCCGATCTGTCTC CAGATCAAMCACAGAGGATT (SEQ ID NO: 107) |
| TRBV6-7 | TGCTCTCACTGACAAA GGAGAAGTT (SEQ ID NO: 108) | TRBV6-8/9 | GACGTGTGCTCTTCCGATCTAAAC ACAGAGGATTTCCCRCTCAG (SEQ ID NO: 109) |

TABLE 2-continued

TCRβ Primer Sequences

| TCRβ alleles | 1st PCR outer 5' - 3' | TCRβ alleles | 2nd PCR inner 5' - 3' |
|---|---|---|---|
| TRBV6-8 | TGCTGCTGGTACTACTGACAAAGAA (SEQ ID NO: 110) | | |
| TRBV6-9 | GCTGGTATCACTGACAAAGGAGAAG (SEQ ID NO: 111) | | |
| TRBV7-1/2/3 | CAGGTCATAMTGCCCTTTAYTGGT (SEQ ID NO: 112) | TRBV7-1 | GACGTGTGCTCTTCCGATCTGTCTGAGGGATCCATCTCCACTC (SEQ ID NO: 113) |
| TRBV7-4 | GACTTACTCCCAGAGTGATGCTCAA (SEQ ID NO: 114) | TRBV7-2 | GACGTGTGCTCTTCCGATCTTCGCTTCTCTGCAGAGAGGACTGG (SEQ ID NO: 115) |
| TRBV7-5/6/7/9 | AGGGCCMAGAGTTTCTGACTTMCTT (SEQ ID NO: 116) | TRBV7-3 | GACGTGTGCTCTTCCGATCTCTGAGGGATCCGTCTCTACTCTGAA (SEQ ID NO: 117) |
| TRBV7-8 | GCCAGAGTTTCTGACTTATTTCCAG (SEQ ID NO: 118) | TRBV7-4/8 | GACGTGTGCTCTTCCGATCTCTGAGRGATCCGTCTCCACTCTG (SEQ ID NO: 119) |
| | | TRBV7-5 | GACGTGTGCTCTTCCGATCTGGTCTGAGGATCTTTCTCCACCT (SEQ ID NO: 120) |
| | | TRBV7-6/7 | GACGTGTGCTCTTCCGATCTGAGGGATCCATCTCCACTCTGAC (SEQ ID NO: 121) |
| | | TRBV7-9 | GACGTGTGCTCTTCCGATCTCTGCAGAGAGGCCTAAGGGATCT (SEQ ID NO: 122) |
| TRBV8-1 | TGCTCAGATTAGGAACCATTATTCA (SEQ ID NO: 123) | TRBV8-1 | GACGTGTGCTCTTCCGATCTAAGCTCAAGCATTTCCCTCAAC (SEQ ID NO: 124) |
| TRBV8-2 | AACAGTGTTCTGATATCGACAGGA (SEQ ID NO: 125) | TRBV8-2 | GACGTGTGCTCTTCCGATCTATGTCACAGAGGGGTACTGTGTTTC (SEQ ID NO: 126) |
| TRBV9 | GTACTGGTACCAACAGAGCCTGGAC (SEQ ID NO: 127) | TRBV9 | GACGTGTGCTCTTCCGATCTACAGTTCCCTGACTTGCACTCTG (SEQ ID NO: 128) |
| TRBV10 | GGTATCGACAAGACCYGGGRCAT (SEQ ID NO: 129) | TRBV10-1/3 | GACGTGTGCTCTTCCGATCTACAAAGGAGAAGTCTCAGATGGCTA (SEQ ID NO: 130) |
| TRBV11 | ACAGTTGCCTAAGGATCGATTTTCT (SEQ ID NO: 131) | TRBV10-2 | GACGTGTGCTCTTCCGATCTTGTCTCCAGATCCAAGACAGAGAA (SEQ ID NO: 132) |
| TRBV12-1/2 | CAGGGACTGGAATTGCTGARTTACT (SEQ ID NO: 133) | TRBV11 | GACGTGTGCTCTTCCGATCTCTGCAGAGAGGCTCAAAGGAGTAG (SEQ ID NO: 134) |
| TRVB12-3/4/5 | TCTGGTACAGACAGACCATGATGC (SEQ ID NO: 135) | TRBV12-1/2 | GACGTGTGCTCTTCCGATCTATCATTCTCYACTCTGAGGATCCAR (SEQ ID NO: 136) |
| TRBV13 | TTCGTTTTATGAAAGATGCAGAGC (SEQ ID NO: 137) | TRVB12-3/4/5 | GACGTGTGCTCTTCCGATCTACTCTGARGATCCAGCCCTCAGAAC (SEQ ID NO: 138) |
| TRBV14 | ATCGATTCTTAGCTGAAAGGACTGG (SEQ ID NO: 139) | TRBV13 | GACGTGTGCTCTTCCGATCTCAGCTCAACAGTTCAGTGACTATCAT (SEQ ID NO: 140) |
| TRBV15 | AGACACCCCTGATAACTTCCAATCC (SEQ ID NO: 141) | TRBV14 | GACGTGTGCTCTTCCGATCTGAAAGGACTGGAGGGACGTATTCTA (SEQ ID NO: 142) |

TABLE 2-continued

TCRβ Primer Sequences

| TCRβ alleles | 1st PCR outer 5' - 3' | TCRβ alleles | 2nd PCR inner 5' - 3' |
|---|---|---|---|
| TRBV16 | AAACAGGTATGCCCAA GGAAAGATT (SEQ ID NO: 143) | TRBV15 | GACGTGTGCTCTTCCGATCTGCCG AACACTTCTTTCTGCTTTCT (SEQ ID NO: 144) |
| TRBV17 | AAACATTGCAGTTGATT CAGGGATG (SEQ ID NO: 145) | TRBV16 | GACGTGTGCTCTTCCGATCTATTTT CAGCTAAGTGCCTCCCAAAT (SEQ ID NO: 146) |
| TRBV18 | CATAGATGAGTCAGGA ATGCCAAAG (SEQ ID NO: 147) | TRBV17 | GACGTGTGCTCTTCCGATCTCACA GCTGAAAGACCTAACGGAAC (SEQ ID NO: 148) |
| TRBV19 | TCAGAAAGGAGATATA GCTGAAGGGTA (SEQ ID NO: 149) | TRBV18 | GACGTGTGCTCTTCCGATCTATTTT CTGCTGAATTTCCCAAAGAG (SEQ ID NO: 150) |
| TRBV20-1 | CAAGGCCACATACGAG CAAGGCGTC (SEQ ID NO: 151) | TRBV19 | GACGTGTGCTCTTCCGATCTGTCTC TCGGGAGAAGAAGGAATC (SEQ ID NO: 152) |
| TRBV21-1 | TCAGAAAGCAGAAATA ATCAATGAGC (SEQ ID NO: 153) | TRBV20-1 | GACGTGTGCTCTTCCGATCTGACA AGTTTCTCATCAACCATGCAA (SEQ ID NO: 154) |
| TRBV22-1 | GAGGAGATCTAACTGA AGGCTACGTG (SEQ ID NO: 155) | TRBV21-1 | GACGTGTGCTCTTCCGATCTCAATG CTCCAAAAACTCATCCTGT (SEQ ID NO: 156) |
| TRBV23-1 | CAAGAAACGGAGATGC ACAAGAAG (SEQ ID NO: 157) | TRBV22-1 | GACGTGTGCTCTTCCGATCTAGGA GAAGGGGCTATTTCTTCTCAG (SEQ ID NO: 158) |
| TRBV24-1 | CGGTTGATCTATTACTC CTTTGATGTC (SEQ ID NO: 159) | TRBV23-1 | GACGTGTGCTCTTCCGATCTATTCT CATCTCAATGCCCCAAGAAC (SEQ ID NO: 160) |
| TRBV25-1 | AATTCCACAGAGAAGG GAGATCTTT (SEQ ID NO: 161) | TRBV24-1 | GACGTGTGCTCTTCCGATCTGACA GGCACAGGCTAAATTCTCC (SEQ ID NO: 162) |
| TRBV26 | ACTGGGAGCACTGAAA AAGGAGATA (SEQ ID NO: 163) | TRBV25-1 | GACGTGTGCTCTTCCGATCTAGTCT CCAGAATAAGGACGGAGCAT (SEQ ID NO: 164) |
| TRBV27 | TTCAATGAATGTTGAG GTGACTGAT (SEQ ID NO: 165) | TRBV26 | GACGTGTGCTCTTCCGATCTCTCTG AGGGGTATCATGTTTCTTGA (SEQ ID NO: 166) |
| TRBV28 | CGGCTGATCTATTTCTC ATATGATGTT (SEQ ID NO: 167) | TRBV27 | GACGTGTGCTCTTCCGATCTCAAA GTCTCTCGAAAAGAGAAGAGGA (SEQ ID NO: 168) |
| TRBV29-1 | GACACTGATCGCAACT GCAAAT (SEQ ID NO: 169) | TRBV28 | GACGTGTGCTCTTCCGATCTAAGA AGGAGCGCTTCTCCCTGATT (SEQ ID NO: 170) |
| TRBV30 | GCCTCCAGCTGCTCTTC TACTCC (SEQ ID NO: 171) | TRBV29-1 | GACGTGTGCTCTTCCGATCTCGCCC AAACCTAACATTCTCAA (SEQ ID NO: 172) |

In some aspects, the present disclosure provides a method for analyzing single T cells comprising: a) sorting single T cells f into separate locations; b) amplifying nucleic acids from each single T cell using a first set of primers capable of amplifying a plurality of nucleic acids encoding T cell receptors to produce a first set of amplicon products; c) performing nested PCR with a second set of primers to produce a second set of amplicon products, wherein each primer comprises a common sequence such that each amplicon product is capable of hybridizing to a primer comprising a barcode sequence; d) amplifying the second set of amplicon products with a third set of primers, wherein each primer comprises a barcode sequence to identify the single T cell from which each amplified nucleic acid originated; and e) sequencing the third set of amplicon products. The method may further comprise lysing each single T cell prior to amplifying the target nucleic acids. If desired, the relative expression levels of the target nucleic acids may also be determined. In certain embodiments, the method further comprises analyzing the sequences of the amplified nucleic acids for splice variations, somatic mutations, or genetic polymorphisms.

The separate locations can be separate reaction containers, such as wells of a multi-well plate (e.g., 96 well plate, 384-well plate, 1536-well plate) or microwell array, capillaries or tubes (e.g., 0.2 mL tubes, 0.5 mL tubes, 1.5 mL tubes), or chambers in a microfluidic device. Alternatively, the separate locations can be emulsion droplets that spatially separate cells.

Various methods are known in the art for isolating single cells. In some embodiments, the sample is sorted to obtain single T cells using a flow cytometer. Methods of preparing a sample of cells for flow cytometry analysis is described in, e.g., U.S. Pat. Nos. 5,378,633, 5,631,165, 6,524,858, 5,266,269, 5,017,497 and 6,549,876; U.S. App. Pub. Nos. US20120178098, US20080153170, 20010006787, US20080158561, US20100151472, US20100099074, US20100009364, US20090269800, US20080241820, US20080182262, US20070196870 and US20080268494; PCT publication WO99/54494; Brown et al (Clin Chem. 2000 46:1221-9), McCoy et al (Hematol. Oncol. Clin. North Am. 2002 16:229-43) and Scheffold J. Clin. Immunol. 2000 20:400-7) and books such as Carey et al (*Flow Cytometry in Clinical Diagnosis*, 4th Edition ASCP Press, 2007), Ormerod (*Flow Cytometry—A practical approach* 3rd Edition. Oxford University Press, Oxford, U K 2000), Ormerod (*Flow Cytometry* 2nd Edition. BIOS Scientific Publishers, Oxford, U K 1999) and Ormerod (*Flow Cytometry—A basic introduction* 2009 Cytometry Part A 75A, 2009), each of which are incorporated by reference herein.

Primers used in amplification include TCR primers for both TCR alpha and beta chain gene transcripts and phenotyping primers for multiple cytokines (e.g., pro-inflammatory and inhibitory) and transcription factors that are important in T cell function and specific for particular T cell types. Exemplary TCR and T cell phenotypic marker primers are disclosed for example in U.S. Patent Publication No. 20150337369; incorporated herein by reference. The primers are used in polymerase chain reaction (PCR)-based techniques, such as RT-PCR, for amplification of T cell mRNA. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) *PCR Protocols* (Academic Press, N Y 1990); Taylor (1991) *Polymerase chain reaction: basic principles and automation, in PCR: A Practical Approach*, McPherson et al. (eds.) IRL Press, Oxford; Saiki et al. (1986) *Nature* 324:163; as well as in U.S. Pat. Nos. 4,683,195, 4,683,202 and 4,889,818, all incorporated herein by reference.

In particular, PCR uses relatively short oligonucleotide primers which flank the target nucleotide sequence to be amplified, oriented such that their 3' ends face each other, each primer extending toward the other. The polynucleotide sample is extracted and denatured, e.g., by heat, and hybridized with first and second primers that are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. In some cases, PCR is carried out with a commercially available thermal cycler, e.g., Perkin Elmer.

RNA may be amplified by reverse transcribing the RNA into cDNA, and then performing PCR (RT-PCR), as described above. Alternatively, a single enzyme may be used for both steps as described in U.S. Pat. No. 5,322,770, incorporated herein by reference in its entirety. RNA may also be reverse transcribed into cDNA, followed by asymmetric gap ligase chain reaction (RT-AGLCR) as described by Marshall et al. (1994) *PCR Meth. App.* 4:80-84. Suitable DNA polymerases include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. In some cases, exogenous RNAse H, such as *E. coli* RNAse H, is added, even when AMV reverse transcriptase is used. RNAse H is readily available from, e.g., Bethesda Research Laboratories.

The methods of the present disclosure may utilize a multiplexed nested RT-PCR approach. For each T cell target nucleic acid, PCR is carried out in at least two steps, wherein the amplicon product from a first round of PCR becomes the template for a second round of PCR using a second set of primers, at least one of which binds to an interior location of the amplicon from the first round of PCR, to generate a second amplicon product. In certain embodiments, a third round of PCR is carried out on the second amplicon product using a third set of primers to generate a third amplicon product.

In certain embodiments, multiplexed nested PCR is carried out with multiple T cell target sequences (e.g., encoding TCRs and other T cell phenotypic markers) simultaneously in the same reaction mixture. Distinct sets of primers are employed for each sequence being amplified as described herein. Exemplary primers are described in U.S. Patent Publication No. 20150337369 for amplifying TCRs (e.g., both α and (β chains of the heterodimer) and various other T cell phenotypic markers, including cytokines (e.g., pro-inflammatory and inhibitory) and transcription factors, which are important in T cell function and specific for particular T cell types, and also for adding barcodes and sequencing adapters for paired-end sequencing. Changes to the nucleotide sequences of these primers may be introduced corresponding to genetic variations in particular T cells.

In certain cases, a first set of primers used to amplify a target nucleic acid, e.g., a nucleic acid encoding a TCR or a T cell phenotypic marker, may contain a primer that specifically hybridizes to and amplifies, when paired with another appropriate primer in the first set, the target nucleic acid during a first round of PCR. A second set of primers may then be used to further amplify the target nucleic acid when the second set contains a primer that specifically hybridizes to and amplifies, when paired with another appropriate primer in the second set, a specific amplification product of the first round of PCR during a second round of PCR. Similarly, a third set of primers may then be used to further amplify the target nucleic acid when the third set contains a primer that specifically hybridizes to and amplifies, when paired with another appropriate primer in the third set, a specific amplification product of the second round of PCR during a third round of PCR.

In some embodiments, primers within a set of primers may include, in addition to a sequence that hybridizes to a target nucleic acid, or an amplification product thereof, a common sequence and/or a barcode sequence. The common sequence may be the same sequence among a plurality of primers that otherwise hybridize to and amplify, when appropriately paired with another primer, different target nucleic acids, or amplification products thereof. In some cases, the common sequence in a primer used during a round of PCR enables a primer used during a following round of PCR to anneal to and amplify, when paired with an appropriate primer, the target nucleic acid by serving as an annealing site for the primer used during a following round of PCR. As such, in some cases the common sequence in a primer used during a round of PCR is a sequence that does not hybridize to target-specific sequences of a target nucleic acid, or to a specific amplification product from a previous round of PCR. In some cases, the common sequence is a sequence that hybridizes to a target nucleic acid, if, for example, the target nucleic acid includes a sequence that is shared among different target nucleic acids, e.g., a sequence encoding a constant region of a TCR.

The multiplexed PCR reactions may be carried out in one or more of the separate locations into which single T cells from a sample have been sorted. In some cases, the amplification products of the multiplexed PCR reaction carried out in multiple separate locations are combined into one pool before sequencing. In such cases, the barcode sequence used in one of the rounds of the multiplexed PCR reactions may be used to enable identification of the location, e.g., well, from which a particular sequenced amplification product originated, as described further below.

In certain embodiments, the T cell phenotypic marker is selected from IL2, IL10, IL12A, IL13, IL17A, IFNG, PRF1, GZMB TGFB, TNFA, BCL6, TBET, GATA3, RORC, FOXP3, RUNX1, RUNX3, CD4, CD8, CD11a, CD18, CD25, CD29, CCD30, CD38, CD44, CD45, CD45RA, CD45RO, CD49d, CD62, CD62L, CD69, CD71, CD103, CD137 (4-1BB), CD161, CD294, CCR5, CXCR4, HLA-DR, IL-5, IL-6, IL-9, IL-12, IL-15, IL-21, TLR2, TLR3, TLR4, TLR5, TLR6, TLR7, TLR8, TLR9 and TLR10. In some embodiments, the T cell phenotypic marker is selected from: IL2, IL10, IL12A, IL13, IL17A, IFNG, PRF1, GZMB TGFB, TNFA, BCL6, TBET, GATA3, RORC, FOXP3, RUNX1, and RUNX3.

Additionally, barcode sequences can be added to amplicon products to identify the single T cell from which each amplified nucleic acid originated. The use of barcodes allows nucleic acid analytes from different cells to be pooled in a single reaction mixture for sequencing while still being able to trace back a particular target nucleic acid to the particular cell from which it originated. Each cell is identified by a unique barcode sequence comprising at least five nucleotides. A barcode sequence can be added during amplification by carrying out PCR with a primer that contains a region comprising the barcode sequence and a region that is complementary to the target nucleic acid of interest such that the barcode sequence is incorporated into the final amplified target nucleic acid product. Barcode sequences can be added at one or both ends of an amplicon. In certain embodiments, single cells are initially sorted to separate locations in an ordered array or multi-well plate where the cell can be identified by its position using barcodes. For example, barcode sequences can be added at both ends of an amplicon to identify the position of a cell in a multi-well plate by using a first barcode added at one end to identify the row and a second barcode added at the other end to identify the column of the multi-well plate.

In addition, adapter sequences can be added to amplicons to facilitate high-throughput amplification or sequencing. For example, a pair of adapter sequences can be added at the 5' and 3' ends of a DNA template to allow amplification or sequencing of multiple DNA templates simultaneously by the same set of primers.

Primers can be readily synthesized by standard techniques, e.g., solid phase synthesis via phosphoramidite chemistry, as disclosed in U.S. Pat. Nos. 4,458,066 and 4,415,732, incorporated herein by reference; Beaucage et al., *Tetrahedron* (1992) 48:2223-2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109. Poly(A) or poly(C), or other non-complementary nucleotide extensions may be incorporated into oligonucleotides using these same methods. Hexaethylene oxide extensions may be coupled to the oligonucleotides by methods known in the art. Cload et al., *J. Am. Chem. Soc.* (1991) 113:6324-6326; U.S. Pat. No. 4,914,210 to Levenson et al.; Durand et al., *Nucleic Acids Res.* (1990) 18:6353-6359; and Horn et al., Tet. Lett. (1986) 27:4705-4708.

Moreover, the oligonucleotides, particularly the primer oligonucleotides for amplification or sequencing, may be coupled to labels for detection. There are several means known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., *Nucl. Acids Res.* (1978) 5:363-384 which discloses the use of ferritin-avidin-biotin labels; and Chollet et al., *Nucl. Acids Res.* (1985) 13:1529-1541 which discloses biotinylation of the 5' termini of oligonucleotides via an aminoalkylphosphoramide linker arm.

Any high-throughput technique for sequencing can be used in the practice of the invention. DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, sequencing by synthesis using allele specific hybridization to a library of labeled clones followed by ligation, real time monitoring of the incorporation of labeled nucleotides during a polymerization step, polony sequencing, SOLID sequencing, and the like. These sequencing approaches can thus be used to sequence target nucleic acids of interest, including nucleic acids encoding TCRs and other T cell phenotypic markers amplified from single T cells.

Certain high-throughput methods of sequencing comprise a step in which individual molecules are spatially isolated on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. Patent Publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). Such methods may comprise amplifying the isolated molecules either before or after they are spatially isolated on a solid surface. Prior amplification may comprise emulsion-based amplification, such as emulsion PCR, or rolling circle amplification.

Of particular interest is sequencing on the Illumina® MiSeq platform, which uses reversible-terminator sequencing by synthesis technology (see, e.g., Shen et al. (2012) *BMC Bioinformatics* 13:160; Junemann et al. (2013) *Nat. Biotechnol.* 31(4):294-296; Glenn (2011) *Mol. Ecol. Resour.* 11(5):759-769; Thudi et al. (2012) *Brief Funct. Genomics* 11(1):3-11; herein incorporated by reference).

The present disclosure also provides a method for analyzing multiplexed single cell sequencing data, such as those acquired using the method of analyzing single T cells described herein. In one implementation of the computer-implemented method, a user may access a file on a computer system, wherein the file is generated by sequencing multiplexed PCR amplification products from multiple single T cells by, e.g., a method of analyzing single T cells, as described herein. Thus, the file may include a plurality of sequencing reads for a plurality of nucleic acids derived from multiple T cells. Each of the sequencing reads may be a sequencing read of a nucleic acid that contains a target nucleic acid nucleotide sequence (e.g., a nucleotide sequence encoding T cell receptor or a T cell phenotypic marker) and one or more barcode sequences that identifies the single cell source (e.g., a single cell in a well in a multi-well plate, a capillary, a microfluidic chamber, etc.) from which the nucleic acid originated (e.g., after multiple nested PCR of the target nucleic acid expressed by a single T cell in the well). In some embodiments, the sequencing read is a paired-end sequencing read.

The sequencing reads in the file may be assembled to generate a consensus sequence of a target nucleic acid nucleotide sequence by matching the nucleotide sequence corresponding to the target nucleic acid nucleotide sequence and the barcode sequences contained in each sequencing read. Those sequencing reads that originate from the same single cell source (e.g., same well) and have a target nucleotide sequence that has a higher identity to a reference sequence than a threshold identity level may be assigned to the same target nucleic acid that was initially amplified from the single cell source, and may be grouped into a subset representing the target nucleic acid. The number of sequencing reads within the subset indicates how likely it is that the consensus sequence assembled from the sequencing reads in a subset is part of an actual nucleic acid molecule that was present in the single cell source. Thus, if the number of sequencing reads in a subset is above a background level, the consensus sequence derived from the subset may be considered to represent an actual sequence of a target nucleic acid in the single cell source. The consensus sequence may then be outputted, e.g., to a display, printout, database, etc.

V. Methods of Use

In some embodiments, the methods of the present disclosure provide T cells with known 2D affinity and sequence. Further embodiments provide methods for the use of these antigen-specific T cells for adoptive cell transfer (ACT) such as for the treatment of cancer or infections as well as methods of monitoring immunotherapies including monoclonal antibodies and ACT. In order to extend the capacity to use adoptive cell therapy (ACT) to treat patients with more rapidly growing tumors, it is a goal to transfer enriched, peptide-specific effector T cells (both CD4 T helper cells and cytotoxic T lymphocytes) that have been selected for their ligand specificities to effectively attack tumor cells while avoiding serious attack of normal tissues. The affinity of TCR's for a specific antigen makes them valuable for several therapeutic approaches. For example, cancer patients, such as melanoma patients, can be effectively treated by using adoptive immunotherapy.

Characterization of antigen-specific T cells is of interest in connection with a variety of conditions associated with T cell activation. Such conditions include autoimmune diseases, e.g. multiple sclerosis, myasthenia gravis, rheumatoid arthritis, type 1 diabetes, graft vs. host disease, Grave's disease, etc.; various forms of cancer, e.g. carcinomas, melanomas, sarcomas, lymphomas and leukemias. Various infectious diseases such as those caused by viruses, e.g. HIV-1, hepatitis, herpesviruses, enteric viruses, respiratory viruses, rhabdovirus, rubeola, poxvirus, paramyxovirus, morbillivirus, etc. are of interest. Infectious agents of interest also include bacteria, such as *Pneumococcus, Staphylococcus, Bacillus. Streptococcus, Meningococcus, Gonococcus, Eschericia, Klebsiella, Proteus, Pseudomonas, Salmonella, Shigella, Hemophilus, Yersinia, Listeria, Corynebacterium, Vibrio, Clostridia, Chlamydia, Mycobacterium, Helicobacter* and *Treponema*; protozoan pathogens, and the like. T cell associated allergic responses may also be monitored, e.g. delayed type hypersensitivity or contact hypersensitivity involving T cells.

High affinity functional antigen-specific T cells identified by the methods of the present disclosure may be used to treat a disease (e.g., cancer, infectious disease, or autoimmune disease) in a subject by administering a composition comprising the high affinity antigen-specific T cells.

Accordingly, embodiments of the present disclosure concern obtaining and administering T cells to a subject as an immunotherapy to target cancer cells. A wide variety of cancers, including solid tumors and leukemias are amenable to the compositions and methods disclosed herein. Types of cancer that may be treated include: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; Sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include: angiokeratoma; angio lymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In some embodiments, the subject can be administered nonmyeloablative lymphodepleting chemotherapy prior to the T cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m$^2$ fludarabine is administered for five days.

In certain embodiments, a T-cell growth factor that promotes the growth and activation of the autologous T cells is administered to the subject either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T-cell growth factor.

In certain embodiments, the compositions and methods of the present embodiments involve a high affinity T cell therapy in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

Infectious diseases include those associated with infectious agents and include any of a variety of bacteria (e.g., pathogenic *E. coli, S. typhimurium, P. aeruginosa, B. anthracia, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses (e.g., adenovirus, bunyavirus, herpesvirus, papovavirus, paramyxovirus, picornavirus, rhabdovirus (e.g., Rabies), orthomyxovirus (e.g., influenza), poxvirus (e.g., Vaccinia), reovirus, retroviruses, lentiviruses (e.g., HIV), flaviviruses (e.g., HCV) and the like).

Further embodiments provide methods for the generation of human T cell lines or clones (e.g. pathogen/tumor-specific or autoreactive T cells) for clinical research, diagnostics, and immunotherapy. The isolation of antigen-specific T cell populations directly ex vivo followed by immediate transfer of the cells into recipients (without any further in vitro propagation) is of special clinical interest. It is expected that directly isolated cell populations are much more efficient than cultured cells for in vivo applications. Extremely high numbers of in vitro expanded T cells are required for effective adoptive transfers, a phenomenon most likely due to the adaptation of T cells to in vitro culture conditions. An example for an important clinical application for this procedure is the parallel purification and adoptive transfer of EBV- and/or CMV-specific T cell populations during [otherwise] T cell-depleted stem cell transplantations, a protocol which is likely to dramatically reduce the incidence of EBV and CMV-related malignancies in transplant patients. Thus, the antigen-specific T cells identified by the methods of the present invention can be used for these clinical applications.

Another embodiment of the invention relates to a method, where after characterization of the T cell affinity and sequence, the TCR sequence is cloned. In this embodiment the method comprises the steps of (i) preparing cDNA from said T-cell clone, (ii) amplifying said cDNA, and (iii) cloning the respective TCR α and β genes into a vector. In particular aspects, the vector is a retroviral vector for the transduction of human peripheral blood lymphocytes.

In some embodiments, the methods provided herein are used for functional T cell diagnostics. The iTAST method allows for the direct characterization of live, antigen-specific T cells. Thus, the characterized antigen-specific T cells can be used in functional assays of chronic virus infections (e.g., HIV, CMV, EBV, HBV, or HCV) or tumor-specific T cell populations.

In some aspects, the present invention provides a pharmaceutical composition which comprises a high affinity functional CTL and a pharmaceutically acceptable carrier. An injectable composition is a pharmaceutically acceptable fluid composition comprising at least one active ingredient, e.g., an expanded T-cell population (for example autologous or allogenic to the patient to be treated) expressing a given TCR. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this disclosure are conventional; appropriate formulations are well known to those of ordinary skill in the art.

Methods are also provided for optimizing therapy, by analyzing the TCR repertoire in a sample, and based on that information, selecting the appropriate therapy, dose, treatment modality, etc. that is optimal for stimulating or suppressing a targeted immune response, while minimizing undesirable toxicity. The treatment is optimized by selection for a treatment that minimizes undesirable toxicity, while providing for effective activity. For example, a patient may be assessed for the immune repertoire relevant to an autoimmune disease, and a systemic or targeted immunosuppressive regimen may be selected based on that information.

In some aspects, the present disclosure provides methods of assessing health in a subject. For example, a measure of TCR affinity distribution may be used to assess the health of a subject. For example, the TCR affinity distribution to the HCV peptide antigen skews to low T cell affinity with increased age. Thus, in some aspects, a decrease in TCR affinity distribution may indicate poor health (e.g., elderly donor) or diminished protection against infection.

In some embodiments, TCR affinity distribution can be used as a donor signature. For example, the TCR affinity distribution is consistent from multiple blood draws within the same donor; however, the TCR affinity distribution can differ between donors. Accordingly, in some aspects, the TCR affinity distribution can be used as a unique signature for a donor.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—In Situ T Cell Receptor Affinity and Sequence Test (iTAST)

In order to solve issues with measuring TCR affinity, the in situ T cell receptor affinity and sequence test (iTAST) technology was developed to enable measurement of both TCR affinity and its sequence directly from primary CTLs. Starting from blood, TCR affinity and sequence for about 50 T cells can be determined in a day starting from as few as 75 antigen-specific CTLs. iTAST takes advantage of streptamers (Knabel et al., 2002) to reversibly label antigen-specific T cells and the recently-developed micropipette adhesion assay (Huang et al., 2010; Jiang et al., 2011) for measurement of two dimensional (2-D) TCR-pMHC binding affinity (FIG. 2A), which correlates better with T cell function than three-dimensional (3-D) affinity obtained in SPR5. The analysis was focused on CTLs because of their ability to directly kill target cells and their wide applications in cancer immunotherapy and persistent viral infections (Restifo et al., 2012; Heslop et al., 1996). CTLs specific for a given antigen were first isolated with streptamers using the tetramer enrichment protocol (Yu et al., 2015) dissociated off using an excess amount of biotin to leave the TCRs unbound, and then contacted with pMHCs coated on Red Blood Cells (RBCs) for 2-D affinity measurement in the micropipette adhesion assay. CTLs were then transferred individually into lysis buffer for TCR sequence amplification and next-generation sequencing library preparation.

Figure 6:
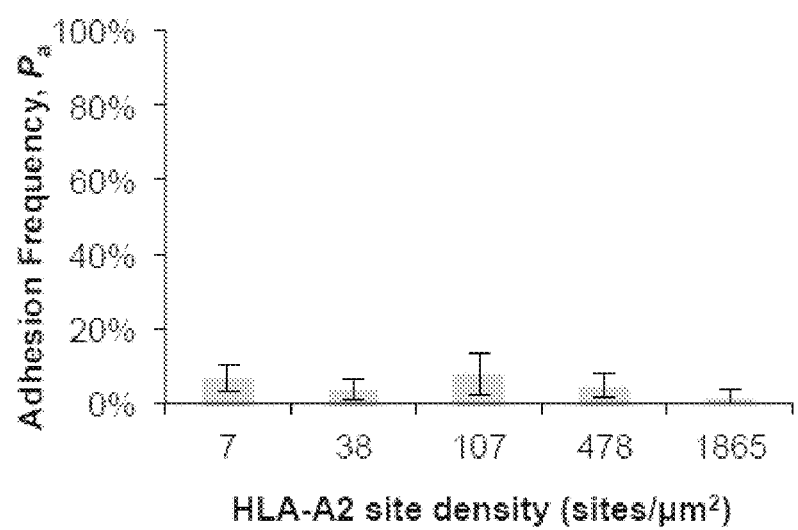
FIG. 6: Non-specific adhesion on primary CD8$^+$ T cells is negligible and is not correlated with pMHC site density. Red blood cells bearing HCV-HLA-A*02:01 (CD8 mutant) of varying site densities were used to interact with freshly purified CD8$^+$ T cells from human PBMCs to assess the background adhesion level. Adhesion frequency is measured by the average of 50 contacts with 4 seconds at each contact. pMHC site densities were measured using HLA-A2 antibody.
Figures 7A, 7B:
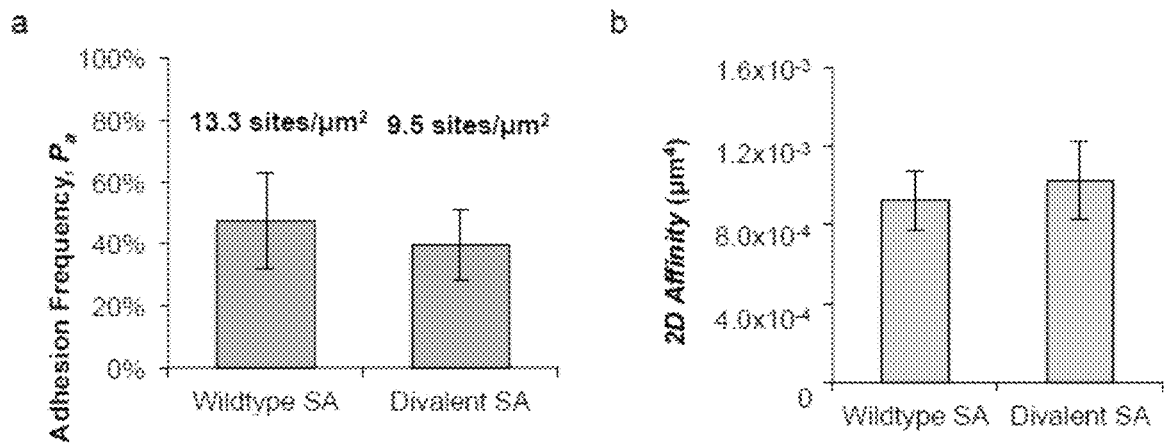
FIG. 7A-B: Multi-valency of pMHC does not affect 2D affinity measurement. To exclude the possibility of multivalent TCR-pMHC interactions introduced by immobilizing multiple pMHCs onto one streptavidin molecule, the affinity measurement obtained from one HCV-specific T cell clone was compared using either red blood cells conjugated with pMHC captured by (A) wild type tetravalent streptavidin or (B) mutant divalent streptavidin. Divalent streptavidin would represent a biomolecular interaction, as one binding pocket is occupied to the biotin on the red blood cell, and the other one by the pMHC. No differences were observed in the affinity measurement between divalent and tetravalent streptavidin, indicating that wild type streptavidin is suitable for measurement of the bimolecular TCR-pMHC interaction (Huang et al., 2010).

Affinity measurements were performed using HLA-A2 monomers with mutations in the α3 domain that abolish CD8 cooperativity in TCR-pMHC binding (Jiang et al., 2011). The nonspecific binding with primary CTLs was negligible and stayed relatively constant with relation to a large range of pMHC site densities on RBCs (FIG. 6). Using a panel of CTL clones, it was confirmed that the adhesion frequency curve fit the model for bimolecular interactions (Chesla et al., 1998) (FIG. 2A and Eq 1) and the use of wild type streptavidin as a means to present pMHC on RBC membrane did not cause alterations of 2D affinity via possible multivalent interactions (Huang et al., 2010) (FIG. 7).

Figure 8:
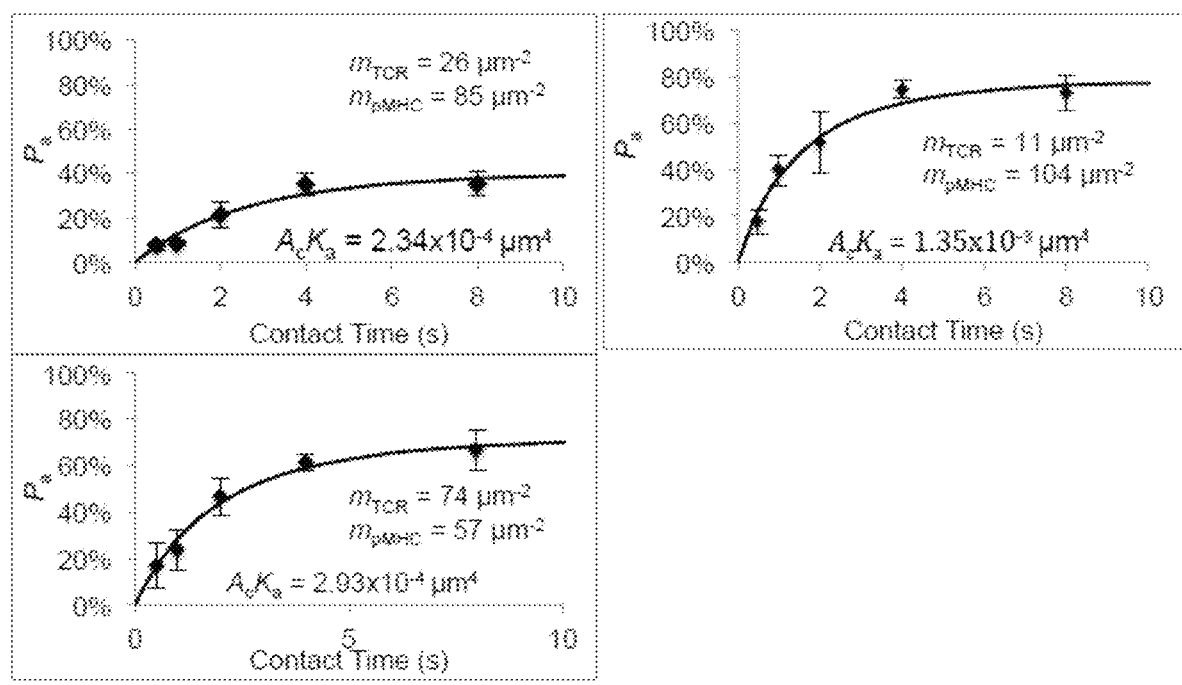
FIG. 8: 2-dimensional affinity kinetics curve for three additional CD8$^+$ T cell clones. Adhesion probability (Pa) was plotted as a function of contact time(s). TCR affinity, AcKa, for each clone is indicated. Solid line is the model fit.
Figure 9:
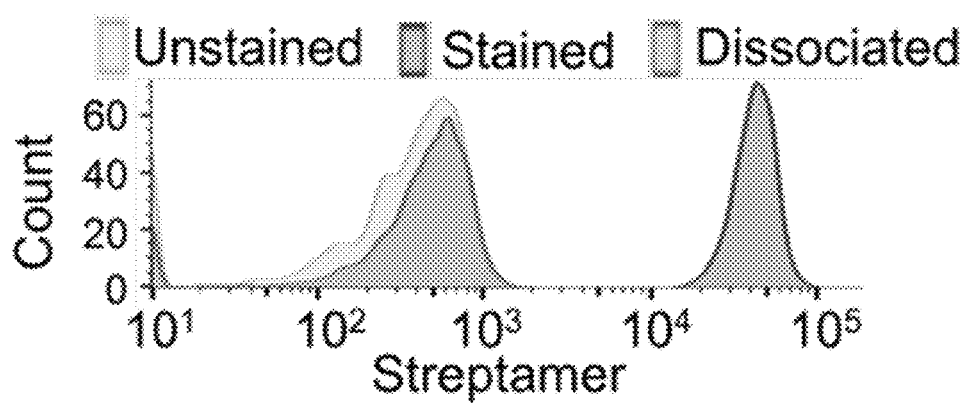
FIG. 9: Streptamer staining is fully reversible. Streptamers can be completely dissociated off of the surface of antigen-specific T cells. An HCV-specific clone is stained with PE-labeled streptamer bearing the HCV peptide at 4° C. in FACS buffer (PBS, 2% FBS, 2 mM EDTA, sodium azide) (Nauerth et al., 2013). Cells were then dissociated of streptamer by washing into FACS buffer containing excess biotin and are shown to overlap with unstained cells.
Figure 10:
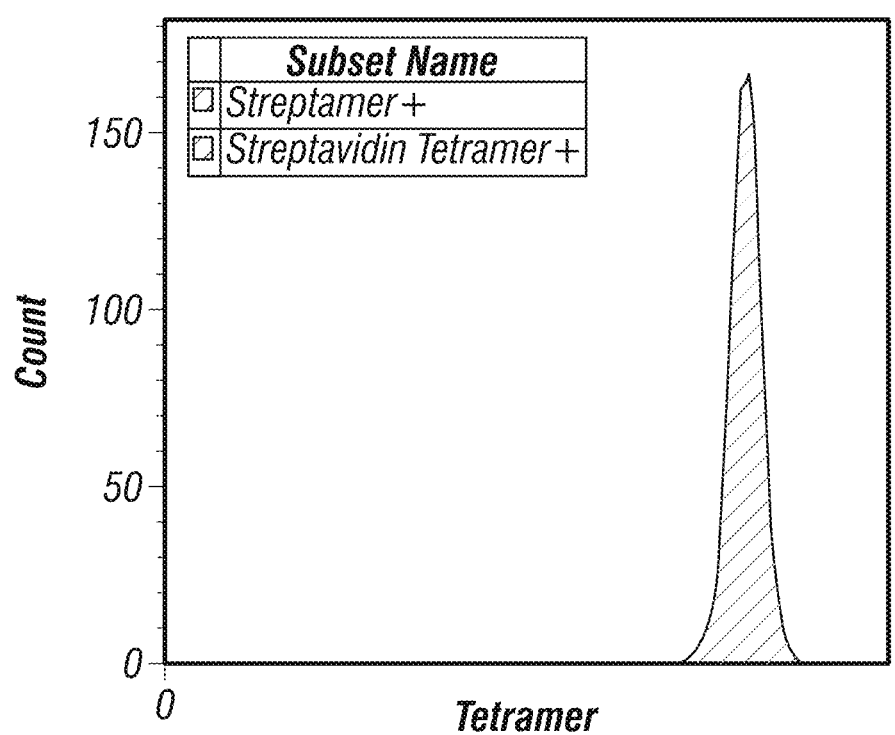
FIG. 10: Streptamers stain with similar intensity as conventional tetramers. CD8-enriched cells from one sample were split in half, with one half stained using conventional tetramers made from streptavidin and other half stained with streptamers, both for the HCV peptide.
Figure 11:
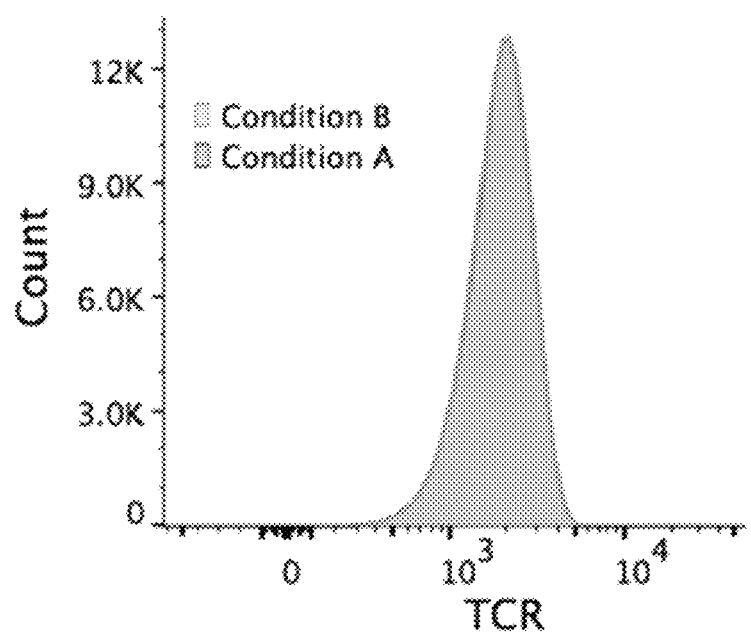
FIG. 11: Phenotypic antibodies have no effect on TCR expression level. The ability to accurately measure 2D affinity requires that the T cell receptor expression level remain constant during the duration of the affinity experiment. Although streptamers are dissociated off of the T cells after sorting, the other antibodies remain attached. To show that attachment of these antibodies do not change the TCR expression level, the following experiment was performed. A CD8+ primary T cell enriched sample was split in half into two conditions. For Condition A, cells were stained with an antibody cocktail (specific for CD27, CD45RA, CD57, CXCR3, CD95, CD45RO, and CCR7) for 30 minutes at 4° C. in FACS buffer, then left to sit in CTL media at room temperature for 3 hours to simulate 2D affinity measurement, and then stained with TCR antibody at 4° C. for 30 minutes in FACS buffer before analysis. For Condition B, cells were left for 30 minutes at 4° C. in FACS buffer, followed by sitting in CTL media at room temperature for 3 hours, and then stained with both the antibody cocktail mentioned in condition A and TCR antibody at 4° C. for 30 minutes before analysis. As such, conditions A and B were treated the same way with regards to their environment, with the exception that condition A had antibodies conjugated to the T cells during the 3 hours in CTL media, which represents their condition during the 2D affinity test. No difference can be seen in the TCR expression level between condition A and condition B, which means that staining of the given antibodies did not affect the TCR expression level of cells during the 2D affinity test.

Measurement of the 2D binding affinity in iTAST requires measurement of receptor-ligand adhesion frequency at an equilibrium contact time with a known TCR site density and a known pMHC site density (Eq. 2) (Chesla et al., 1998). Based on the CTL clones, it was found that four seconds was a sufficient contact time to achieve equilibrium adhesion frequency for a range of TCR affinities (FIGS. 2A and 8). While HLA-A2- and TCR-specific antibodies are used to measure site densities, TCR site density cannot be measured directly on single streptamer-positive T cells as the TCR antibody would impede the interrogation of their 2D affinity. Thus, bulk CTLs from the same patient were used as a surrogate. Streptamer sorted cells have the same TCR site density as the bulk CTL because streptamers completely dissociate from the cell surface (FIG. 9) and do not alter TCR site density (FIG. 2B). Streptamers also perform similarly to conventional tetramers, as both reagents yield similar cell frequencies and staining intensity from the same sample (FIG. 10). The ligation of common CTL phenotypic antibodies CD27, CD45RA, CD45RO, and CCR7 also did not change the TCR site density during affinity measurement (FIG. 11).

Figure 2D:
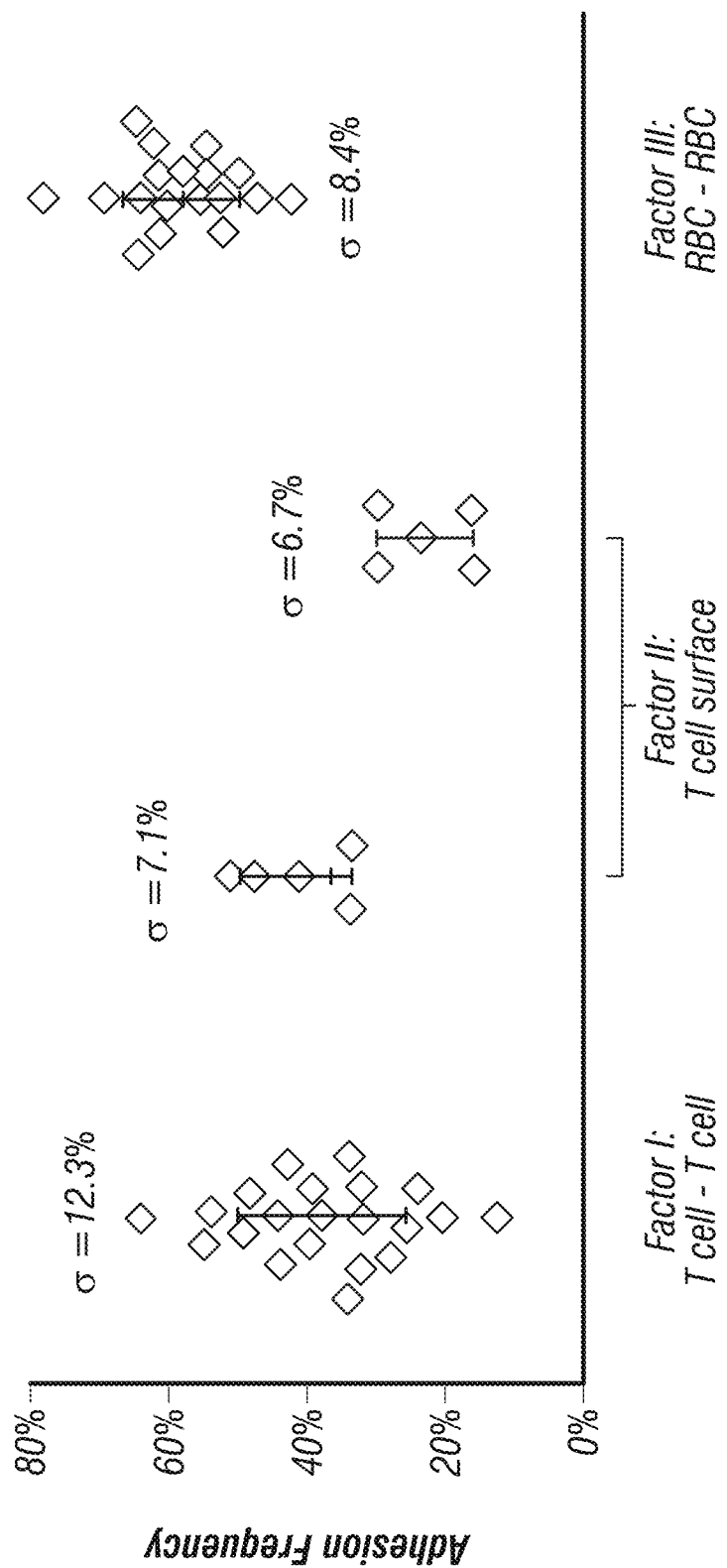
Figures 12A, 12B, 12C, 12D:
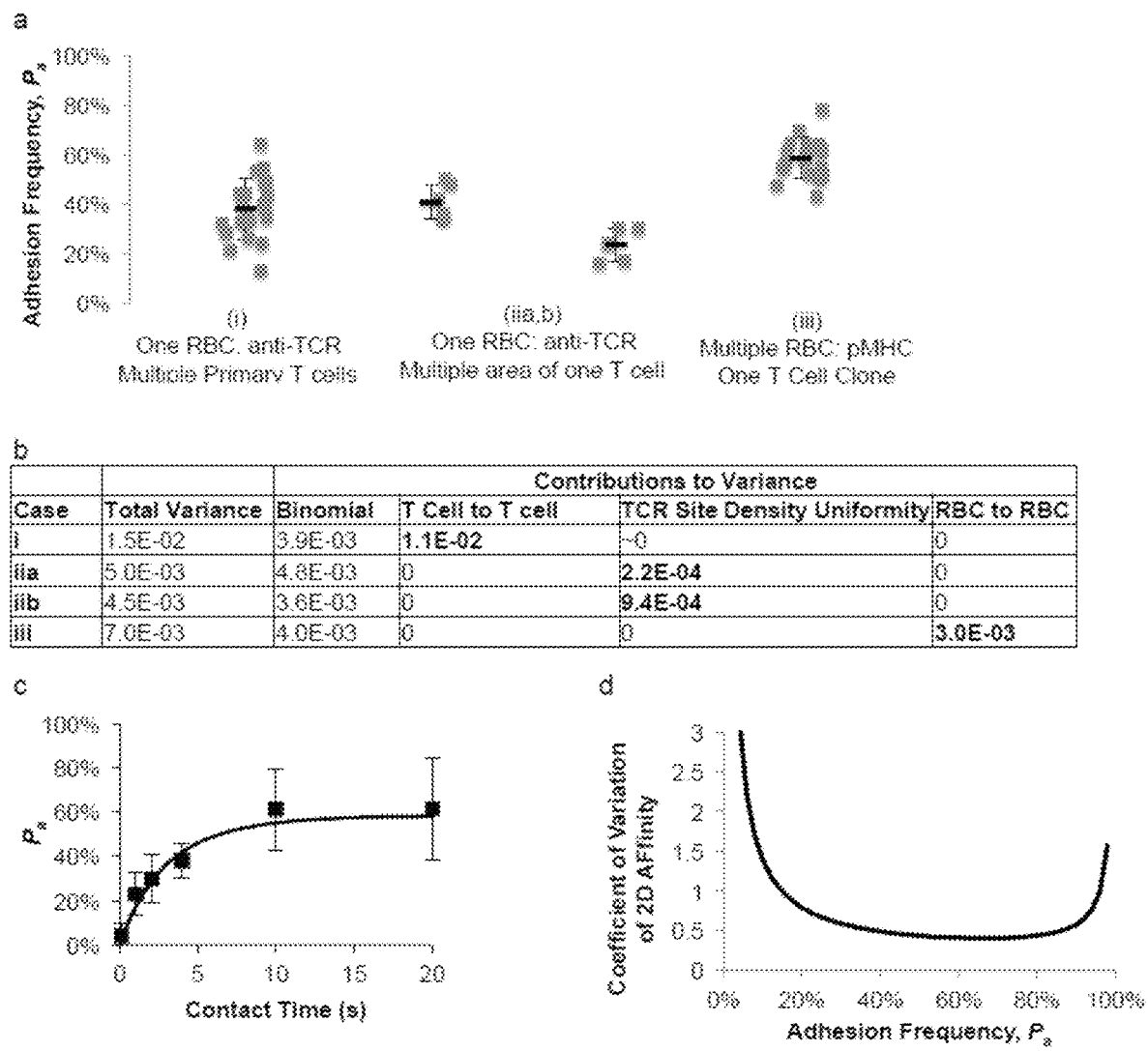
FIGS. 12A-12D: Estimating the error of primary T cell affinity measurements. To measure the error in the 2D affinity calculation of primary T cells, all possible sources of errors to the measured adhesion frequency were considered, Pa.
Figures 13A, 13B, 13C, 13D, 13E, 13F, 13G, 13H:
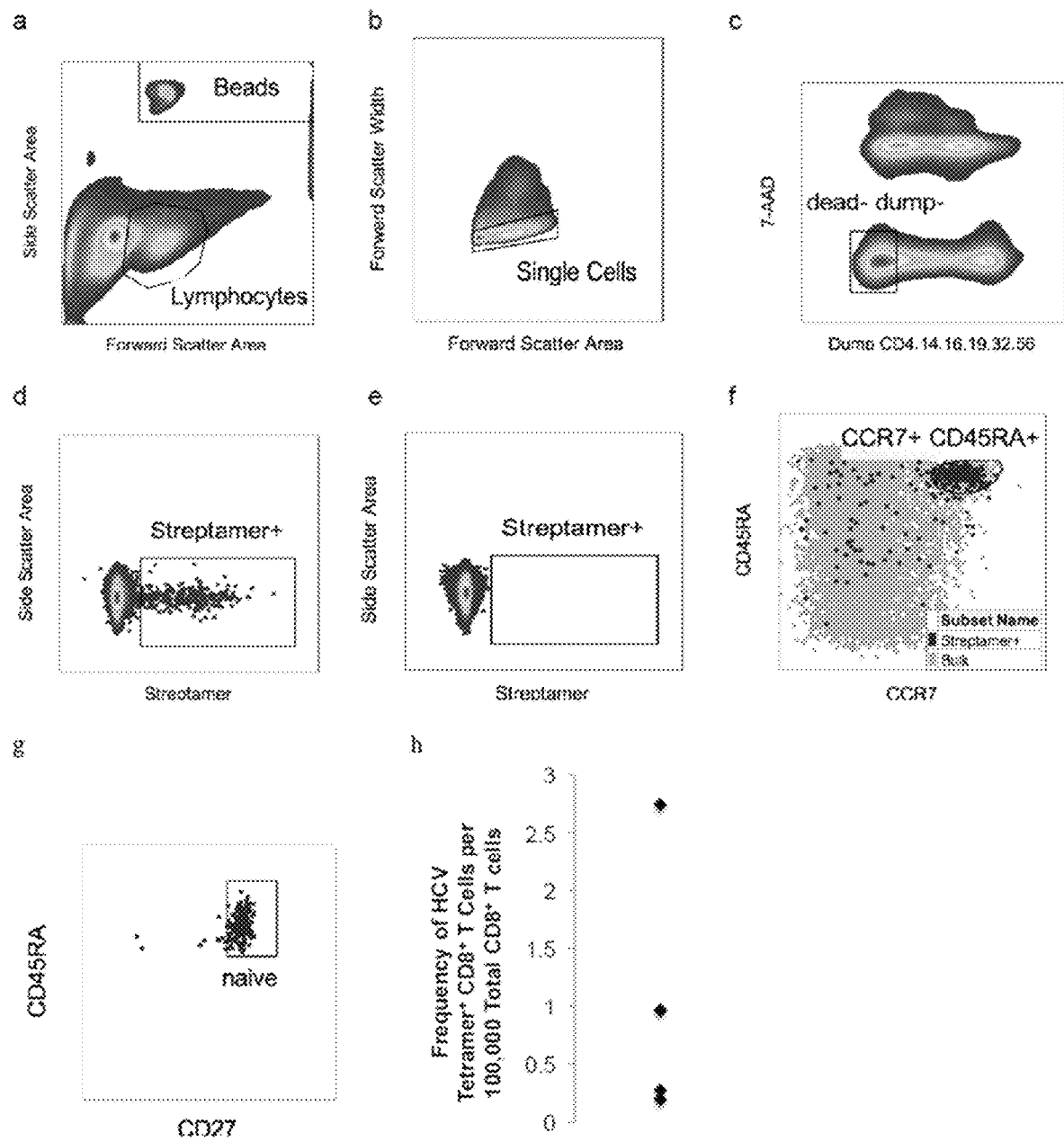

2D affinity measurement from single cells is subject to multiple variables that affect accuracy. To estimate the error, a variance analysis was performed of factors associated with the 2D affinity measurement, including variations in (i) TCR site density between T cells and (ii) around the surface of one T cell, and (iii) variations in pMHC site density between RBCs (FIG. 12). By adding all variances, it was estimated that the coefficient of variation of adhesion frequency on primary T cells is less than 0.5 by keeping the adhesion frequency above between 30% and 80%. To evaluate the accuracy of primary 2D affinities, affinity-tested primary CTLs were picked into culture medium for in vitro expansion. It was found that the 2D affinity of the primary CTL is similar to its clone and within the estimated variance (FIG. 2D).

Example 2—Validation of iTAST in HCV-Specific CTLs

Having validated the iTAST method, it was next applied to study the rare HCV-specific CTL population within healthy HCV seronegative blood donors. Antigen-specific T cells are a heterogeneous populations of cells that recognize the same pMHC ligand using different TCRs generated by VDJ recombination (Yu et al., 2015; Moon et al., 2007). In pathogen naïve individuals, HCV-specific cells are extremely rare and are present in 1 in $10^5$ to $10^6$ CD8$^+$ T cells, and are believed to be the safety net against infections and vaccination. However, the clonal lineage and affinity distribution of TCRs from this heterogeneous population of T cells have not been studied due to the lack of a proper technology. The common HCV epitope that binds to HLA-A2-ns3:1406-1415 (SEQ ID NO:1 KLVALGINAV) (Cerny et al., 1995) (hereafter referred to as HCV-specific T cells) was used. HCV-specific T cells from donors 1-3 with ages of 62, 49, and 33, respectively, were isolated and found to have frequencies between 2 to 27 in $10^6$ total CD8$^+$ T cells (FIG. 13H), which is consistent with a previous study (Yu et al., 2015). From one unit of leukapheresis, 65 to 1000 HCV-specific T cells were obtained.

Figure 5A:
Figure 5B:
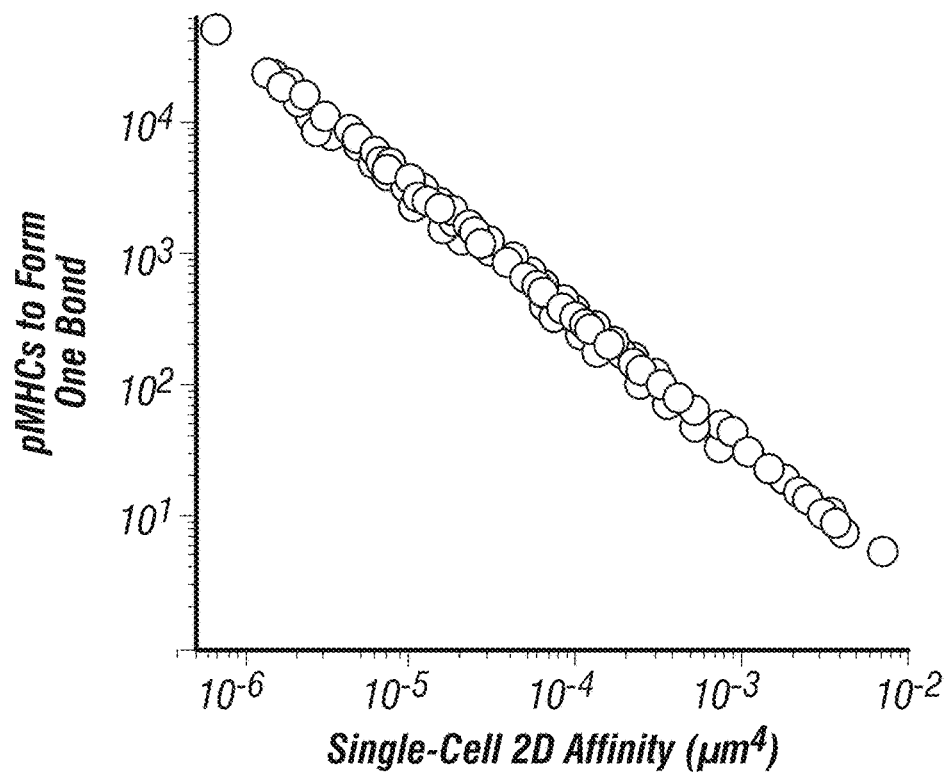

Among the 4 samples from 3 donors tested, a surprisingly large affinity range of over 1000-fold was found within this antigen-specific T cell repertoire (FIG. 5A). Samples 1A and 1B, which are two separate blood draws from donor 1, exhibited a similar distribution of T cell affinity, indicating the reproducibility of iTAST (FIG. 5A). To put this range into perspective, the affinity was transformed into the number of pMHCs required to form on average one bond with TCR at 4 second contact (FIG. 2B, Eq. 3). It should be noted that this value does not take into account bonds that were dissociated before 4 seconds nor does it take into account the lifetime of a bond, and so this calculation would be an overestimation of the actual required number of pMHCs. Given this, it was found that this affinity range translates to at most 5 required pMHCs for the highest affinity TCRs and 50,000 pMHCs for the lowest affinity TCRs, demonstrating the superb sensitivity that T cells have to antigens (Davis et al., 2007) (FIG. 5B).

Thus, the ability to correlate TCR sequence with 2D affinity provides a method of interrogating the molecular mechanism by which human TCRs bind this pMHC. Affinity-tested cells from donor A and B were picked for single-cell TCR sequencing and a success rate of 69% and 53% was achieved for paired TCRαβ, respectively. No RNA contamination was found between consecutive T cell transfers (FIG. 14). A substantial enrichment of the TRAV38-2 gene was found within all donors, but not in beta chain usage (FIG. 15). However, this enrichment was not reflected in the affinity, as TCRs bearing TRAV38-2 recapitulated the about 500 fold affinity range (FIG. 15). This result is in line with recent evidence that while one TCR hemichain can dictate specificity, the TCR counterchain can regulate the avidity over a broad range (Nakatsugawa et al., 2015).

Simultaneously measuring TCR affinity and TCR sequence also provides a way of tracking T cell clonality in the repertoire. From the 24 successfully paired TCR sequences from donor A, two TCRs were found with the same sequence. These two TCRs had a comparable level of affinity, which further demonstrates the accuracy of iTAST.

Since the naïve phenotype was not sorted exclusively, it is possible that two T cells derived from the same lineage may have been captured due to homeostatic proliferation with cross-reactivity with another epitope (Su et al., 2013). Indeed, donor A contained a large proportion of effector T cells that bound HCV-streptamer despite being HCV seronegative (FIG. 10G).

Example 3—iTAST 2D Affinity for Cell Function

Figure 5C:
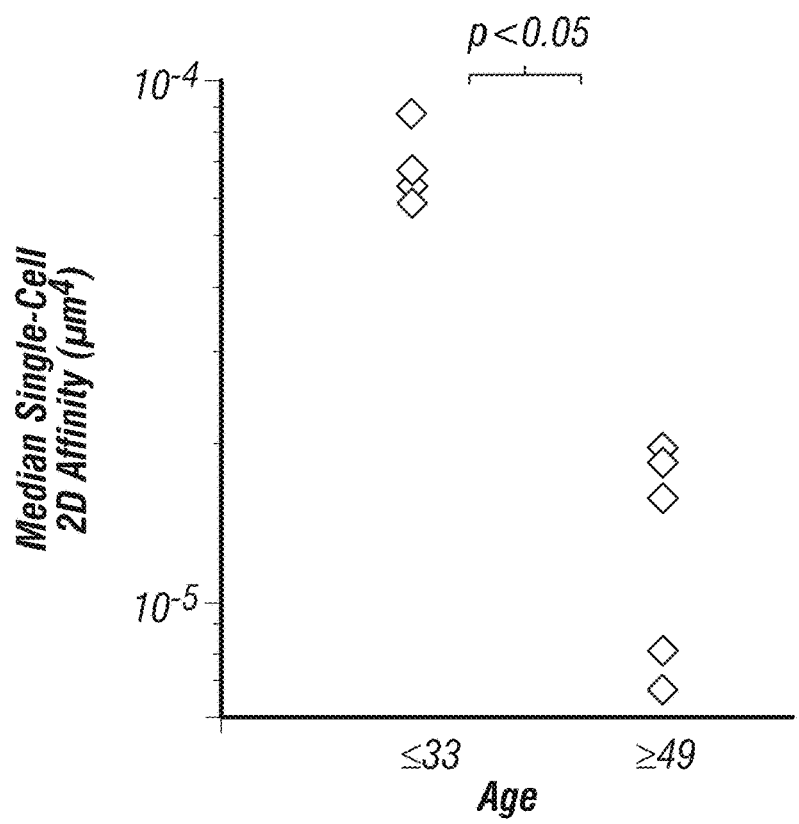

Given the potential of iTAST in immune monitoring and adoptive T cell transfer in cancer, it was next determined whether 2D affinity measured by iTAST is a predictor of cell function. 43 HCV-specific CTLs were in vitro expanded into clones and assessed for functionality by their capacity to kill JY target cells pulsed with HCV peptide. All clones bound specifically and above background adhesion levels to HCV peptide-loaded pMHC in the 2D affinity measurement. It was found that 2D affinity correlated significantly with lysis capacity, with the threshold of functionality beginning at a 2D affinity of about $2\times10^5$ um$^4$, which translates to a requirement of about 1200 pMHCs for T cell activation (FIG. 5B, 5C). It was interesting that donor 3, the youngest donor at 33 years of age, contained significantly more cells above this affinity threshold compared to cells from donors 1 and 2, who are older at 49 and 62 respectively, which contained more cells below this threshold (FIGS. 5A and 14). This sharp delineation between functional and non-functional cells on the basis of 2D affinity means that iTAST can predict the functional potential of a cell without inducing T cell activation that other assays require and can enable further study of T cell repertoire differences between individuals, such as those due to age.

Figure 4A:
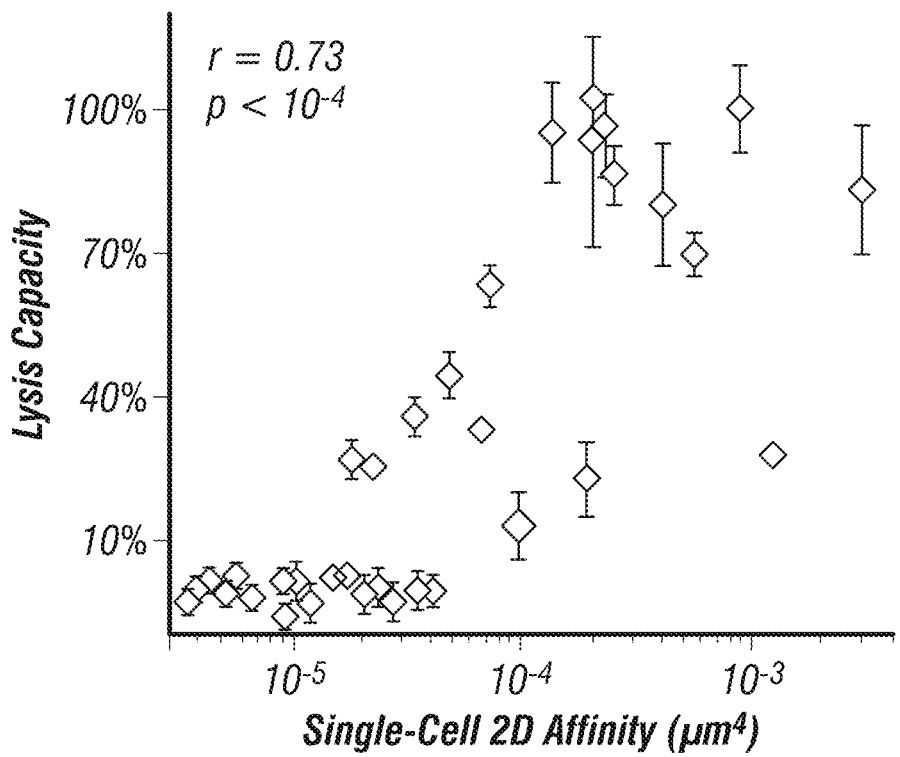
FIGS. 4A-4D: Correlation of Single-Cell 2D affinity with functional capacity. (A) Single-cell 2D affinity of HCV-specific CTLs versus their lysis capacity, defined as the percent specific lysis of HCV peptide-pulsed JY cells (N=43, Spearman two-tailed test). (B) Single-cell 2D affinity versus peptide potency, defined as the peptide concentration required to induce 10% cell lysis (N=15, line denotes log-log linear regression, two-tailed t-test on the slope). HLA-A2-CD8mut/HCV tetramer median fluorescence intensity (MFI) versus (C) lysis capacity (Spearman two-tailed test) and (D) peptide potency (log-log linear regression, two-tailed t-test on the slope). Dashed line denotes limit of detection in tetramer staining.
Figure 4B:
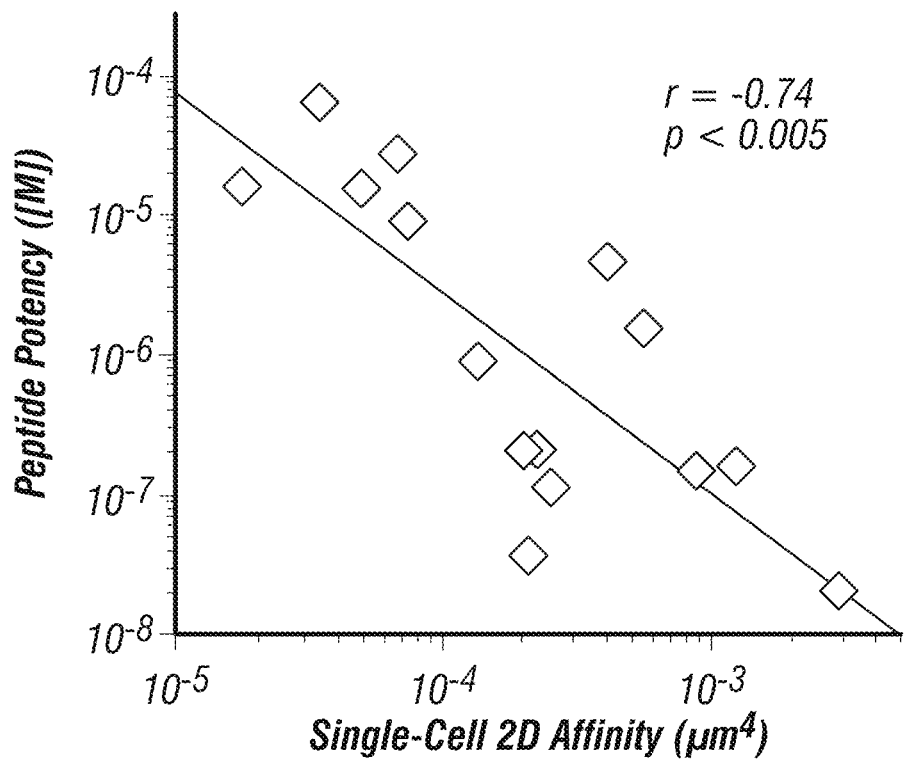
Figure 4C:
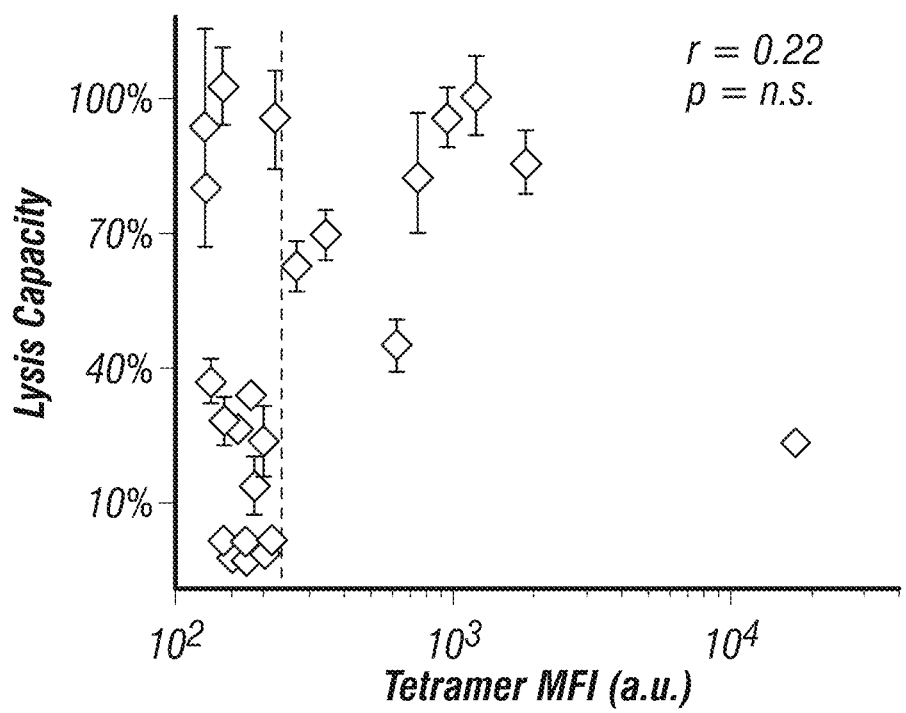
Figure 4D:
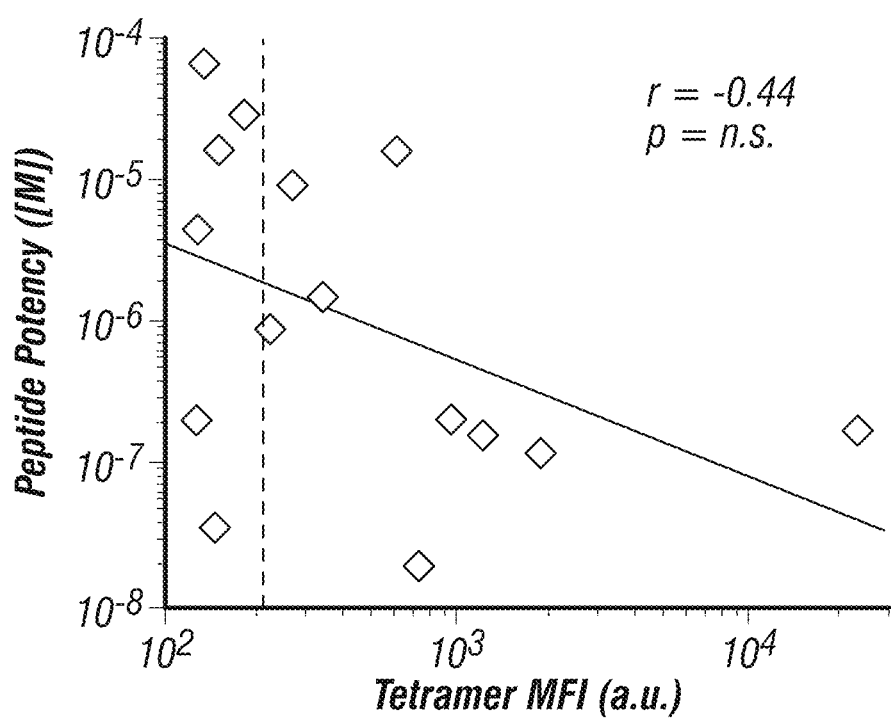

In addition to functional status, TCR-pMHC affinity also affects the peptide potency, which is defined as the minimum peptide concentration required for effector CTLs to induce 10% specific lysis of JY cells pulsed with HCV peptide. Peptide potency is a critical parameter for the in vivo efficacy of CTLs because it is related to the minimum antigenic load required to activate CTLs and elicit a functional response. From HCV-specific CTL clones, there was a significant correlation between single-cell 2D affinity and peptide potency (FIGS. 4B and 11). A competing and widely used in situ technique to identify highly potent CTLs is by staining intensity with HLA-A2-CD8mut tetramers. There was not a significant correlation in tetramer staining with either lysis capacity or peptide potency (FIGS. 4C and D). While all clones that stained tetramer above background levels were functional, in agreement with past studies, multiple clones did not stain despite having a lysis capacity and potency comparable to positively stained cells. This high false negative rate was not seen with single-cell 2D affinities, and thus offers higher predictive value than tetramer staining. In addition, all correlations made using single-cell 2D affinity were consistent with conventional 2D affinity made by averaging several measurements in each of the T cell clones (FIG. 12).

In addition to delineating cell functionality, a significant correlation was also found between the 2D affinity of functional clones and their functional avidity, defined by their sensitivity to peptide (FIG. 16). Another widely used technique to identify functional CTLs is tetramer staining with pMHCs bearing mutations to abrogate CD8 binding. It was found that this was not a strong predictor of cell functionality and missed multiple clones with high lysis capacity (FIG. 4). This demonstrates that iTAST offers a quick, reliable, and unbiased way to identify high affinity functional CTL clones for immunotherapy.

Figure 3B:
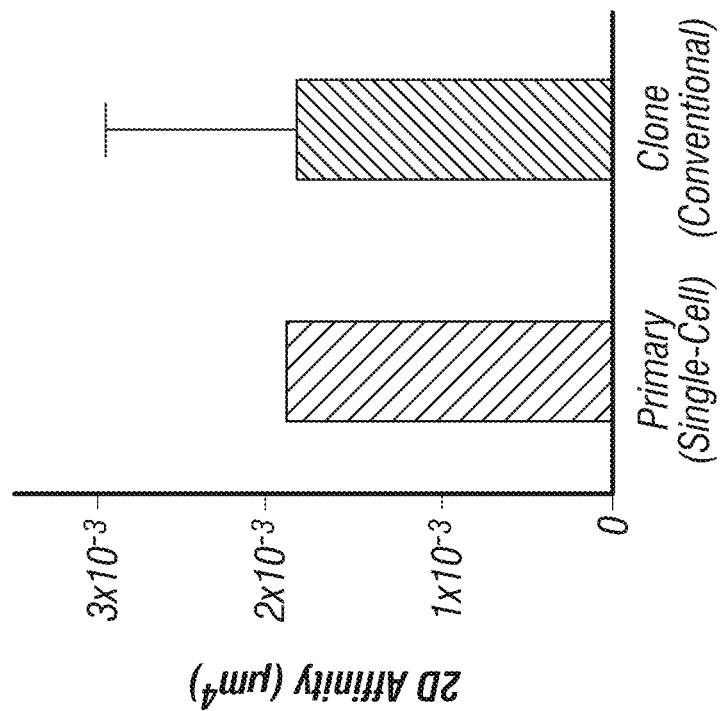
FIGS. 3A-3C. Comparison of single-cell 2D affinity by iTAST with conventional 2D affinity and SPR. (A) Correlation of single-cell 2D affinity and conventional 2D affinity from HCV-specific CTL clones (N=43, line denotes log-log linear regression, two-tailed t-test on the slope) (B) 2D affinity for a primary CTL and its clone after being picked into culture well for in vitro expansion. (C) Correlation of single-cell 2D affinity of the native NY-ESO-1:157-165 and 6 peptide variants on HLA-A2-CD8mut against the 1G4 TCR expressed on the Jurkat cell line, versus 3D affinity by a previously published SPR study (Aleksic et al., 2010) (N=7, line denotes log-log linear regression, two-tailed t-test on the slope).
Figure 3A:
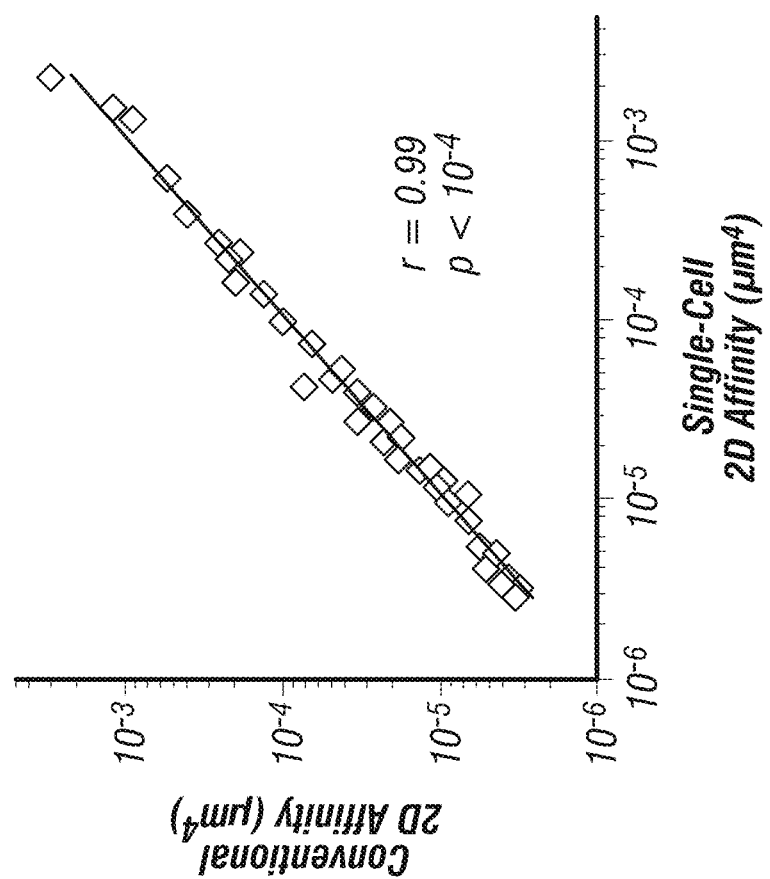
Figure 3C:
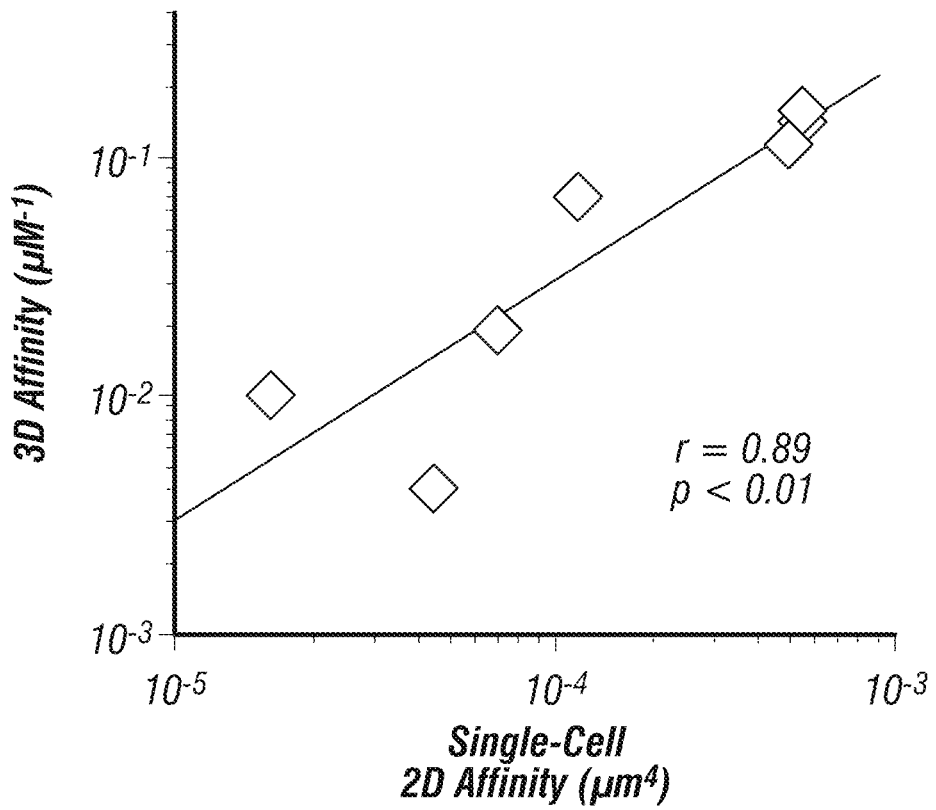

To further demonstrate the utility of iTAST and its consistency with SPR measurement, the 2D affinity of 1G4 TCRs specific for the human tumor antigen NY-ESO-1 that has been previously characterized were tested (Chen et al., 2005). Recently, adoptive transfer of engineered T cells bearing an affinity enhanced variant of 1G4, measured by SPR, has shown successful clinical responses in patients with multiple myeloma (Rapaport et al., 2015). A significant degree of correlation was found between 2D affinity measured by iTAST and the 3D affinity measured by SPR using a panel of NY-ESO-1 peptide variants to the 1G4 TCR (FIG. 3C) except that the iTAST measurements were obtained in a few hours.

iTAST was used to study the affinity distribution of antigen-specific CTL precursors in healthy individuals who have not been exposed to their cognate antigen. Antigen-specific CTLs are heterogeneous population that recognize the same pMHC using different TCRs generated by VDJ recombination. In unexposed individuals, these cells are extremely rare and exist at a frequency of 1 in $10^4$ to $10^6$ CTLs. As a model system, the naïve hepatitis C virus (HCV) specific CTL population was isolated within healthy HCV-seronegative blood donors that binds the HCVns3:1406-1415 (SEQ ID NO:1 KLVALGINAV) epitope complexed with HLA-A2.

HCV-specific CTLs isolated from 12 samples, derived from 9 unique donors, were found to have frequencies ranging from 2 to 18 in $10^6$ total CTLs (FIG. 13), consistent with a previous study. From one unit of leukapheresis, between 50 and 1000 HCV-specific T cells were obtained. A surprisingly large affinity range of over 1000-fold was found within this antigen-specific T cell repertoire (FIG. 5A). 2D affinities were also translated into the number of pMHCs required to form on average one bond with TCR at 4 seconds (Eq. 2 and FIG. 5B); it is noted that this value would be an overestimation of the actual number of pMHCs required because it does not take into account possible transient binding at earlier times. Given this, the 2D affinity range translates to a requirement of at most ~5 pMHCs to bind a CTL with the highest affinity, and ~50,000 pMHCs for the lowest affinity CTL (FIG. 5B).

There was a consistent heterogeneity in the affinity distributions of HCV-specific CTL populations between the donors (FIG. 5A). Samples 4A-B and 5A-C represent repeated blood draws from donor 4 and 5, respectively, collected within a 7 month time span. Samples from the same donor exhibited similar distributions in the T cell affinity while the distributions between donor 4 and 5 were significantly different, with the latter containing a lower median T cell affinity. To investigate whether this heterogeneity is associated with age, additional healthy HCV-seronegative donors 33 or younger and 49 or older were recruited for iTAST measurement. From 9 unique donors, it was found that the naïve HCV-specific CTL repertoire within young donors had a significantly higher median 2D affinity than older donors (FIG. 5C). From the 2D affinity threshold of $2 \times 10^{-5}$ $\mu m^4$ previously determined for in vitro functionality (FIG. 4A), it was also found that older donors contain a significantly lower fraction of functionally competent HCV-specific CTLs than younger donors.

Affinity-tested CTLs from sample 4B, 5A, 6, and 7 were picked for single-cell TCR amplification and sequencing. A success rate of 43-56% for TCRα and 44-75% for TCRβ was achieved, which is comparable to other single-cell TCR amplification methods, and no RNA contamination was found between consecutive T cell transfers (FIG. 17). There was a surprisingly narrow TCRα V-gene (TRAV) usage composed almost exclusively of TRAV38-2 while TCRβ V-gene (TRBV) usage was more diverse (FIG. 5D); this trend was consistent among all four donors. TCRs bearing TRAV38-2 recapitulated the entire affinity range and did not differ in 2D affinity from TCRs without TRAV38-2.

In addition, two pairs of CTLs were observed, each bearing an identical TCRα amino acid sequence but different TCRβ sequences that were isolated from separate donors. The first TCR pair also shared the same TCRβ V-gene, with differences only in the CDR3β region. Despite this similarity, their 2D affinity differed by 50-fold ($2.2 \times 10^4$ vs. $4.2 \times 10^{-6}$ $\mu m^4$). The higher affinity TCR contained a greater proportion of hydrophobic residues in the CDR3β region (SEQ ID NO:2 CASKMGAEAFF, 54% hydrophobic) than the lower affinity TCR (SEQ ID NO:3 CASGQGQETQYF, 17% hydrophobic). It is likely that hydrophobic residues in the CDR3β region interact with the largely hydrophobic HCV peptide (SEQ ID NO:1 KLVALGINAV, 70% hydrophobic) to increase TCR affinity. This observation is supported by the second TCR pair, where a smaller 2D affinity difference of 2.5 fold ($1.1 \times 10^{-5}$ vs. $4.4 \times 10^{-6}$ $\mu m^4$) was associated with a smaller difference in the proportion of CDRβ hydrophobic residues between the high (SEQ ID NO:4 CASSLEREGRGEQFF, 27% hydrophobic) and low (SEQ ID NO:5 CATSIDRGREKLFF, 36% hydrophobic) affinity TCRs. Thus, hydrophobic residues in the CDR3β chain are potential regulators of TCR affinity with the HCV peptide.

Thus, the present disclosure provides a technology for rapid in situ measurement of TCR affinity and sequences directly from primary CTLs isolated from human blood. Adoptive immunotherapy for cancer requires genetic engineering of a patient's T cells to express a high affinity TCR for the cancer antigen. Current approaches relying on directed evolution to improve binding of a TCR can cause reduced specificity and create dangerous cross-reactivity (Zehn et al., 2009). With iTAST, the ability to isolate TCRs native to humans with a given affinity will allow rapid selection of TCRs for cancer immunotherapy. In addition, it has been shown that naïve CMV-specific CTLs from CMV seronegative patients can provide additional protective immunity for adoptive immunotherapy (Hanley et al., 2015). The ability of iTAST to measure low sample size populations such as naïve cells would also be very useful in adoptive therapy for persistent viral infections. Overall, iTAST has broad applications in basic research into TCR affinity as well as clinical applications in profiling CTL response to cancer, infections, and immunization.

Example 4—Materials and Methods

Human CD8$^+$ T Cell Enrichment:

Human Leukocyte Reduction System (LRS) chambers are obtained from The Blood and Tissue Center of Central Texas with strict adherence to guidelines from the Institutional Review Board of University of Texas at Austin.

CD8$^+$ T cell enrichment was done following the protocol described previously (Knabel et al., 2002). Content in LRS chambers is first diluted in Phosphate Buffered Saline (PBS), then ROSETTESEP™ CD8$^+$ T cell Enrichment Cocktail (STEMCELL) is added for 20 minute incubation at room temperature. Cells are spun at 2000 rpm for 15 minutes with no break at room temperature with Ficollpaque (GE Healthcare) added. The enriched CD8$^+$ T cell fraction is collected and RBCs are lysed using ACK lysis buffer (Lonza). After washing in PBS with 10% FBS, the cell mixture is passed through a 70 um filter (Corning). For the remainder of the experiment, the cells are either kept on ice or at 4° C. in refrigerator.

Streptamer Sorting and Dissociation:

The entire procedure is performed either on ice or at 4° C. The enriched CD8+ cells are washed once with FACS buffer (PBS, 2 mM EDTA, 2% v/v FBS, sodium azide) and stained with 0.5 µg PE-conjugated streptamer for 1 hour. It is then washed twice in FACS buffer, and stained with anti-PE Microbeads (Miltenyi) for 20 minutes. After two washes with FACS buffer, cells are passed through a Miltenyi LS column. The flow-through is collected for background staining and frequency calculation.

The enriched fraction is eluted off column and washed once before antibody staining. The antibodies to non-CD8+ T cell markers, CD56, CD4, CD14, CD16, CD19, CD32, along with 7AAD viability marker are used to stain both enriched fraction and 100 µl of flow-through for 30 minutes. In some samples, CD45RA and CCR7 antibodies were also added for phenotypic analysis. The enriched fraction is washed twice and resuspended in FACS buffer with counting beads. Tetramer positive CD8+ T cells are sorted using BD FACS Arial system into 500 µL of dissociation buffer (40% v/v FACS Buffer, 40% v/v FBS, excess D-biotin). After 1.0 hour incubation, the sorted cells are washed twice in CTL media (RPMI+10% FBS+4% human serum+1% pen/strep) and stored at 4° C. until iTAST experiment.

HCV-Specific CTL Lines:

HCV-specific CTL lines are generated according to previously published protocol (Knabel et al., 2002). Briefly, conventional streptavidin-based tetramers are used to sort single cells into 100 uL CTL media in 96-well round-bottom plates using the same isolation procedure as streptamer. $7.5 \times 10^4$ allogeneic irradiated human PBMCs are added to each well, along with 150 U/ml IL-2 (Preprotech), 60 ng/ml anti-CD3 (OKT3), and 60 ng/ml anti-CD28 (CD28.2). Cultures are exchanged every 2-3 days with fresh CTL media in 150 U/ml IL-2. After 14-21 days, clones are transferred to 24-well plates and re-stimulated with 5 µl/ml PHA and $7.5 \times 10_4$/ml allogeneic irradiated human PBMCs. Functional status was analyzed 10-21 days after re-stimulation. JY cells, which are targets for functional studies, are exchanged with fresh media containing CTL every 3 days and kept below 5 million cells/ml.

Micropipette Adhesion Frequency Assay:

The TCR-pMHC affinity were measured using a micropipette adhesion frequency assay that was previously described (Davis et al., 2007). Briefly, a pMHC-coated red blood cell (RBC) and a T cell are aspirated by two opposing micropipettes in CTL media at room temperature. Both pipettes are controlled using highly-precise hydraulic micromanipulators. The RBC is first brought into controlled contact with the T cell using a linear-motion piezo actuator connected to the RBC-containing micropipette. When the RBC is retracted, a positive adhesion event corresponds to a stretching of the flexible RBC membrane at the area of contact. The ability to discern adhesion from no adhesion events is unambiguous. This cycle of approach, contact, and retraction was performed 50 times per cell to obtain the probability of adhesion.

For CTL clones, an adhesion curve can be determined by obtaining the adhesion probability at multiple contact times. This is fit with a known model for reversible bimolecular interactions at two-dimensional surfaces (Moon et al., 2007):

$$P_a = 1 - \exp\{-m_r m_l A_c K_a [-k_{off} t]\} \quad (Eq.\ 1)$$

Where $P_a$ is the adhesion frequency, $m_r$ is the TCR site density, $m_l$ is the pMHC site density, $A_c$ is the contact area between RBC and T cell, $K_a$ is the 2D affinity, $k_{off}$ is the 2D dissociation rate constant, and t is contact time. $A_c$ is kept constant for all measurements, and it is estimated it to be within several percent of 3 µm² based on the length-calibrated images from the microscope. However, since the actual contact area cannot be known, $A_c K_a$ is used as the effective 2D affinity in all 2D affinity publications, with a unit of µm⁴.

The site density of T cell receptor and pMHC is assessed by flow cytometry. For site density, ~10⁵ T cells or RBCs are incubated with 5 µl of PE labeled anti-human αβ TCR (Biolegend clone IP26) or 5 ul of PE labeled anti-HLA-A2 antibody (Biolegend BB7.2) for 1 hour at 4° C. in FACS Buffer, respectively. Measurements are performed in BD Accuri, and site density is quantified using BD quantibrite beads according to manufacturer instructions.

Measuring Primary T Cell Affinity and Transfer for Sequencing:

Streptamer dissociated antigen-specific T cells are added to the microscope chamber, along with 5 populations of RBCs carrying HCV-HLA-A2-CD8 mutant with different site densities. RBC site densities range from ~5 sites/µm² to 2000 sites/µm². In Eq. 1 as t goes to infinity, $P_a$ reaches an equilibrium value:

$$A_c K_a = -\ln(1 - P_{a,eq}) / m_r m_l \quad (Eq.\ 2)$$

For primary CTL affinities, the 2D affinity value was determined using Eq. 2 and by measuring the adhesion frequency at 4 seconds. If the adhesion frequency is lower than 30% after 10 contacts, then a new RBC with a higher site density is used and adhesion frequency is measured again until at least 30% is reached for 10 contacts. When 30 contacts are measured, the cell is aspirated with a transfer micropipette, brought out of the affinity test chamber, and then dipped into 4 uL lysis buffer in a PCR tube.

Another way to use the adhesion frequency $P_a$ is for calculating the average bond number <n>:

$$P_a = 1 - \exp(-<n>)$$

$$<n> = m_r m_l A_c K_a$$

The number of pMHCs required for an average bond number of 1 to form was then derived, using 3 µm² to approximate the contact area:

$$\#\ of\ pMHC\ to\ form\ 1\ bond = \frac{A_c m_{pMHC}}{<n>} = -\frac{A_c m_{pMHC}}{\ln(1 - P_a)} \quad (Eq.\ 3)$$

LDH Cytotoxicity Assay:

JY cells are suspended CTL media at $1 \times 10^6$/ml and cultured with 50 µM HCVns3:1406-1415 peptide overnight. HCV-specific CD8+ T cell clones and JY cells are washed 3 times with CTL media. For lysis capacity, 10⁴ JY cells and 10⁵ T Cells are suspended in 100 µl CTL media, spun for 200 g for 1 minute, and then cultured for 4 hours at 37° C. For peptide sensitivity, $6 \times 10^3$ JY cells and $6 \times 10^4$ T Cells are used. The Pierce LDH Cytotoxicity Assay Kit (Thermo Fisher Scientific) is used according to manufacturer instructions. Briefly, 50 µl of cell supernatant and 50 µl reaction mixture is incubated for 30 minutes at room temperature. 50 µl of stop solution is added, and absorbance is measured using standard plate readers. Percent specific lysis is calculated according to the following formula:

$$\% \text{ Specific Lysis} = \frac{\alpha_{specific} - \alpha_{control}}{\alpha_{max} - \alpha_{spontaneous}}$$

Where α is the difference in absorbance between 490 nm and 680 nm, performed in triplicates. $\alpha_{specific}$ refers to T cells incubated with HCV-pulsed JY cells. $\alpha_{control}$ refers to T cells incubated with non peptide-pulsed JY cells. $\alpha_{max}$ refers to JY cells lysed according to Pierce instructions. $\alpha_{spontaneous}$ refers to JY cells incubating by themselves.

Tetramer Preparation and Staining of CTL Clones:

UV-exchanged tetramer was prepared as previously described (Knabel et al., 2002). 10 µg of HLA-A2 UV cleavable monomer is added with 100 uM peptide and UV-exchanged for 40 minutes on ice, and then left to rest overnight at 4° C. PE-labeled Streptavidin (Biolegend) is then added to the UV-exchanged HLA-A2 in a 4:1 ratio.

For tetramer staining, CTL clones are incubated with 0.14 µg tetramerized-HLA-A2/cd8 mut and 2 ul of CD8 antibody (DK25) in 50 ul FACS buffer for 1 hour at 4° C. Measurements were performed using BD Fortessa.

Quantification of Affinity Measurement Error:

Deviations due to Bernoulli processes are a function of the adhesion frequency and the number of contacts made (n=50). To measure intercellular TCR expression variations, one RBC coated in anti-TCR antibody is used to measure its adhesion frequency with multiple CTLs. To measure pMHC variation, one CTL clone cell is used to measure its adhesion frequency against multiple RBCs. Lastly, to measure the spatial uniformity of TCR expression on one cell, the adhesion frequency of one T cell was measured at multiple locations via gentle tapping to rotate it.

Single Cell TCR Amplification:

Single cell TCR amplification and sequencing was done following a modified version of a published protocol (Han et al., 2014). Briefly, a single CD8$^+$ T cell was directly transferred into lysis buffer and reverse transcription was done either right away or after thawing the frozen lysate. After PCR, multiple cells were pooled, gel purified, and sequenced on Ilumina Mi-seq V2 kit.

TCR Sequence Analysis:

Raw reads were first filtered and separated into α and β chain groups based on constant sequences. For both α and β chain groups, reads were further separated according to cell barcodes. Within each cell, reads were further clustered based on sequence similarity. It is possible for individual T cells to have a second functional α chain and a non-functional β chain. The threshold for detecting a second chain is that the number of reads associated with the second chain be 10 times less abundant than the first chain or more abundant. From each cluster, one consensus sequence was generated based on the consensus of nucleotides weighted by the quality score at that position. Following this method, TCR α and β chain sequences for each single cells can be generated. MIGEC tool were used for V/J assignment and CDR3 annotation.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aleksic, M. et al. *Immunity* 32, 163-174 (2010).
Bennekov et al., *Mt. Sinai J. Med.* 71 (2): 86-93 (2004).
Bernard et al, *Anal. Biochem.*, 273: 221-228 (1999).
Boon et al., *Ann. Rev. Immunol.* 12:337-65 (1994).
Cerny, A. et al. *J Clin Invest* 95, 521-530 (1995).
Chen, J. L. et al. *J Exp Med* 201, 1243-1255 (2005).
Chen, J. L. et al. *J Immunol* 184, 1829-1839 (2010).
Chesla, S. E., Selvaraj, P. & Zhu, C. *Biophys J* 75, 1553-1572 (1998).
Davis, M. M. et al. *Annu Rev Immunol* 25, 681-695 (2007).
Driscoll et al. *J. Mol. Bio.* 232:342-350, (1993).
Frolet et al., *BMC Microbiol.* 10:190 (2010).
Frost, E. L., et al., *J Immunol* 1501521 (2015).
Han, A., et al. *Nat Biotechnol* 32, 684-692 (2014).
Hanley, P. J. et al. *Sci Transl Med* 7, 285ra263 (2015).
Hebeisen, M. et al. *Cancer Res* 75, 1983-1991 (2015).
Heemskerk et al. *Hum Gene Ther.* 19:496-510 (2008).
Heslop, H. E. et al. *Nat Med* 2, 551-555 (1996).
Huang, J. et al. *Nature* 464, 932-936 (2010).
Hubert et al., *Proc. Natl. Acad. Sci. USA* 96 14523-28, (1999).
International Patent Publication No. WO 00/04149
International Patent Publication No. WO 95/20600
International Patent Publication No. WO 98/12302
International Patent Publication No. WO 98/137418
International Patent Publication No. WO 98/20117
International Patent Publication No. WO 99/40188
Janeway et al., Immunobiology: The Immune System in Health and Disease, 3$^{rd}$ Ed., p. 4:33, (1997).
Jiang, N. et al. *Immunity* 34, 13-23 (2011).
Johnson et al. *Blood* 114:535-46 (2009).
King, C. G. et al. *Immunity* 37, 709-720 (2012).
Knabel, M. et al. *Nat Med* 8, 631-637 (2002).
Linnemann, C. et al. *Nat Med* 21, 81-85 (2015).
Lockey et al., *Front. Biosci.* 13:5916-27 (2008).
Loewendorf et al., *J. Intern. Med.* 267(5):483-501 (2010).
Marschall et al., *Future Microbiol.* 4:731-42 (2009)).
McGeoch et al., *Virus Res.* 117:90-104 (2006)
Mettenleiter et al., *Curr. Opin. Microbiol.* 9: 423-29 (2006)).
Miltenyi et al. *Cytometry* 11:231-238, (1990).
Moon, J. J. et al. *Immunity* 27, 203-213 (2007).
Nakatsugawa, M. et al. *J Immunol* 194, 3487-3500 (2015).
Nauerth, M. et al. *Sci Transl Med* 5, 192ra187 (2013).
Nelson, et al., *Proc. Natl. Acad. Sci. USA* 96:3114-19 (1999)
Rapoport, A. P. et al. *Nat Med* 21, 914-921 (2015).
Reiter et al., *Proc. Nat. Acad. Sci. USA* 95:1735-40, (1998).
Renkvist et al., *Cancer Immunol. Immunother.* 50:3-15 (2001).

Restifo, N. P., Dudley, M. E. & Rosenberg, S. A. *Nat Rev Immunol* 12, 269-281 (2012).
Rieder et al., *J. Interferon Cytokine Res.* (9):499-509 (2009).
Roberts et al., *Adv. Virus Res.* 53:301-19) (1999).
Rykman, et al., *J. Virol.* 80(2):710-22 (2006).
Snyder et al., *Nucleic Acids Res.* 35: 401-406 (2007).
Su, L. F., et al. *Immunity* 38, 373-383 (2013).
U.S. Pat. No. 5,019,384
U.S. Pat. No. 5,506,121
U.S. Pat. No. 5,786,148
U.S. Pat. No. 5,840,871
U.S. Pat. No. 5,955,306
U.S. Pat. No. 6,103,493
U.S. Pat. No. 6,544,518
U.S. Patent Publication No. US20150307585
U.S. Patent Publication No. US20150337369
Yu, W. et al. *Immunity* 42, 929-941 (2015).
Zehn, D., Lee, S. Y. & Bevan, M. J. *Nature* 458, 211-214 (2009).
Zysk et al., *Infect. Immun.* 68(6):3740-43 (2000).

What is claimed is:

1. A method for measuring T cell receptor (TCR) affinity and obtaining TCR sequence comprising:
   (a) obtaining a population of antigen-specific T cells from a starting population of T cells using pMHC-tagged streptamers;
   (b) individually performing a micropipette adhesion assay on each of said antigen-specific T cells, thereby measuring the two-dimensional (2D) TCR affinity to a peptide-major histocompatibility complex (pMHC); and
   (c) sequencing the TCR of each of said antigen-specific T cells by paired TCRα/TCRβ sequencing, thereby obtaining the sequence of said TCR.

2. The method of claim 1, wherein antigen-specific T cell isolation comprises:
   (a) staining the starting population of T cells with pMHC-tagged streptamers;
   (b) sorting for the streptamer-bound T cells; and
   (c) dissociating the streptamers from the T cells, thereby obtaining a population of antigen-specific T cells.

3. The method of claim 2, wherein dissociating comprises incubating the streptamer-bound T cells in a dissociation buffer comprising biotin and/or sodium azide.

4. The method of claim 3, wherein the streptamer-bound T cells are incubated for about 15 minutes to about 90 minutes.

5. The method of claim 2, wherein antigen-specific T cell isolation is at 3° C. to 5° C.

6. The method of claim 1, wherein step (a) comprises in vitro clonal expansion of an antigen-specific T cell by co-culturing a population of polyclonal T cells with antigen presenting cells loaded with antigen peptide and/or activating a population of polyclonal T cells with CD3 and CD28.

7. The method of claim 1, wherein the starting population of T cells is a peripheral blood sample comprising CD8$^+$ cytotoxic T Lymphocytes (CTLs) or CD4$^+$T cells obtained from a patient sample or healthy blood donor sample.

8. The method of claim 1, wherein the population of antigen-specific T cells comprises less than 200 T cells or less than 100 T cells.

9. The method of claim 1, wherein the antigen is a tumor associated self-antigen, tumor neo-antigen, or viral antigen.

10. The method of claim 9, wherein the viral antigen is HCV.

11. The method of claim 1, wherein step (b) comprises contacting the antigen-specific T cells with red blood cells coated with agonist pMHC and measuring adhesion frequency.

12. The method of claim 11, wherein the contacting is for 2 seconds to 6 seconds or 3 seconds to 5 seconds.

13. The method of claim 11, further comprising measuring the TCR and pMHC site density and calculating 2D affinity from adhesion probability and site density.

14. The method of claim 13, further comprising estimating that variance associated with the 2D TCR affinity measurement comprising:
   (a) measuring the standard deviation of TCR site density fluctuation between T cells by measuring the adhesion frequencies of one red blood cell (RBC) coated with anti-TCR antibody against multiple T cells;
   (b) measuring the standard deviation of pMHC site density fluctuation between RBCs by measuring the adhesion frequencies of one antigen-specific T cell against multiple RBCs coated with pMHC; and
   (c) measuring the standard deviation of TCR site density fluctuation on the surface of one T cell by measuring the adhesion frequencies of one RBC coated with anti-TCR antibody against multiple areas of one T cell.

15. The method of claim 11, wherein the adhesion frequency is between 30% and 80%.

16. The method of claim 1, wherein step (c) comprises transferring the antigen-specific T cells individually by micropipette into lysis buffer for reverse transcription, PCR amplification of TCRα/TCRβ, and next-generation sequencing.

17. The method of claim 1, wherein the paired TCRα/TCRβ sequencing is performed on single antigen-specific T cells.

18. The method of claim 16, further comprising separating reads according to cell barcodes and clustering reads based on sequence similarity.

19. The method of claim 1, wherein the TCR affinity is obtained and TCR sequence is amplified in 15 hours to 48 hours or 20 hours to 24 hours.

20. A method of monitoring the TCR repertoire of a subject comprising obtaining TCR affinity and sequence according to claim 1.

21. The method of claim 16, wherein the PCR amplification of TCRα/TCRβ comprises primers sequences selected from Table 1 and/or Table 2.

22. The method of claim 1, wherein the antigen is an antigen associated with a disease.

\* \* \* \* \*

UNITED STATES PATENT AND TRADEMARK OFFICE
CERTIFICATE OF CORRECTION

| | |
|---|---|
| PATENT NO. | : 11,162,945 B2 |
| APPLICATION NO. | : 16/092607 |
| DATED | : November 2, 2021 |
| INVENTOR(S) | : Jiang et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 247 days.

Signed and Sealed this
Thirty-first Day of January, 2023

Katherine Kelly Vidal
*Director of the United States Patent and Trademark Office*